United States Patent [19]
Teng et al.

[11] Patent Number: 5,989,885
[45] Date of Patent: Nov. 23, 1999

[54] SPECIFIC MUTATIONS OF MAP KINASE 4 (MKK4) IN HUMAN TUMOR CELL LINES IDENTIFY IT AS A TUMOR SUPPRESSOR IN VARIOUS TYPES OF CANCER

[75] Inventors: David H. -F. Teng; Sean V. Tavtigian; William L. Perry, III; Mark H. Skolnick, all of Salt Lake City, Utah

[73] Assignee: Myriad Genetics, Inc., Salt Lake City, Utah

[21] Appl. No.: 08/874,186

[22] Filed: Jun. 13, 1997

Related U.S. Application Data

[63] Continuation-in-part of application No. 08/782,482, Jan. 10, 1997, abandoned.

[51] Int. Cl.$^6$ .............................. C12N 9/12; C12N 15/52; C12N 15/00
[52] U.S. Cl. .................... 435/194; 435/320.1; 435/91.2; 435/69.1; 435/6; 536/23.1; 536/23.2; 536/24.3; 536/24.33
[58] Field of Search .................................. 435/194, 69.1, 435/6, 320.1, 91.2; 536/24.3, 24.33, 23.1, 23.2

[56] References Cited

U.S. PATENT DOCUMENTS

| | | |
|---|---|---|
| 5,534,426 | 7/1996 | Karin et al. . |
| 5,593,884 | 1/1997 | Karin et al. . |
| 5,605,808 | 2/1997 | Karin et al. . |

OTHER PUBLICATIONS

Collins, L.R. et al. (1996). "G$\alpha_{12}$ Stimulates c–Jun NH$_2$–terminal Kinase through the Small G Proteins Ras and Rac", *J. Biol. Chem.* 271:17349–17353.

Dai, T. et al. (1995). "Stress–activated protein kinases bind directly to the δ domain of c–Jun in resting cell: implications for repression of c–Jun function", *Oncogene* 10:849–855.

Deacon, K. and Blank, J.L. (1997). "Characterization of the Mitogenactivated Protein Kinase Kinase 4 (MKK4)/c–Jun NH$_2$–terminal kinase 1 and MKK3/p38 Pathways Regulated by MEK Kinases 2 and 3", *J. Biol. Chem.* 272:14489–14496.

Dérijard, B. et al. (1994). "JNK1: A Protein Kinase Stimulated by UV Light and Ha–Ras That Binds and Phosphorylates the c–Jun Activation Domain", *Cell* 76:1025–1037.

Dérijard, B. et al. (1995). "Independent Human MAP Kinase Signal Transduction Pathways Defined by MEK and MKK Isoforms", *Science* 267:682–685.

Hirai, S. et al. (1996). "Activation of the JNK pathway by distantly related protein kinases, MEKK and MUK", *Oncogene* 12:641–650.

Lin, A. et al. (1995). "Identification of a Dual Specifically Kinase That Activates the Jun Kinases and p38–Mpk2", *Science* 268:286–290.

Minden, A. et al. (1994). "Differential Activation of ERK and JNK Mitogen–Activated Protein Kinases by Raf–1 and MEKK", *Science* 266:1719–1723.

Nishina, H. et al. (1997). "Stress–signalling kinase Sek1 protects thymocytes from apoptosis mediated by CD95 and CD3", *Nature* 385:350–353.

Sánchez, I. et al. (1994). "Role of SAPK/ERK kinase–1 in the stress–activated pathway regulating transcription factor c–Jun", *Nature* 372:794–798.

Su, B. et al. (1994). "JNK Is Involved in Signal Integration during Costimulation of T Lymphocytes", *Cell* 77:727–736.

Yang, D. et al. (1997). "Targeted disruption of the MKK4 gene causes embryonic death, inhibition of c–Jun NH$_2$–terminal kinase activation, and defects in AP–1 transcriptional activity", *Proc. Natl. Acad. Sci. USA* 94:3004–3009.

*Primary Examiner*—Rebecca E. Prouty
*Assistant Examiner*—Richard Hutson
*Attorney, Agent, or Firm*—Rothwell, Figg, Ernst & Kurz, P.C.

[57] ABSTRACT

The present invention relates to mutations in the MKK4 gene in human cancers and their use in the diagnosis and prognosis of human cancer. Specific mutations in the MKK4 gene which are associated with breast, pancreatic, colorectal and testicular cancers have been identified. The invention also relates to the therapy of human cancers which have a mutation in the MKK4 gene, including gene therapy, protein replacement therapy and protein mimetics. Finally, the invention relates to the screening of drugs for cancer therapy.

9 Claims, 3 Drawing Sheets

FIG. 1

SPECIFIC MUTATIONS OF MAP KINASE 4 (MKK4) IN HUMAN TUMOR CELL LINES IDENTIFY IT AS A TUMOR SUPPRESSOR IN VARIOUS TYPES OF CANCER

CROSS REFERENCE TO RELATED APPLICATIONS

This application is a continuation-in-part of application Ser. No. 08/782,482 filed on Jan. 10, 1997 which is incorporated herein by reference, now abandoned.

BACKGROUND OF THE INVENTION

The present invention relates to somatic mutations in the MKK4 gene in human cancers and their use in the diagnosis and prognosis of human cancer. This gene has been previously reported in the literature (Dérijard et al., 1995; Lin et al., 1995) and has also been called JNKK. It is known to be a protein kinase, but it has not previously been associated with cancer nor was it recognized to be a tumor suppressor gene.

The publications and other materials used herein to illuminate the background of the invention, and in particular, cases to provide additional details respecting the practice, are incorporated herein by reference, and for convenience are referenced in the following text and respectively grouped in the appended List of References.

The genetics of cancer is complicated, involving multiple dominant, positive regulators of the transformed state (oncogenes) as well as multiple recessive, negative regulators (tumor suppressor genes). Over one hundred oncogenes have been characterized. Fewer than a dozen tumor suppressor genes have been identified, but the number is expected to increase beyond fifty (Knudson, 1993).

The involvement of so many genes underscores the complexity of the growth control mechanisms that operate in cells to maintain the integrity of normal tissue. This complexity is manifested in another way. So far, no single gene has been shown to participate in the development of all, or even the majority of human cancers. The most common oncogenic mutations are in the H-ras gene, found in 10–15% of all solid tumors (Anderson et al., 1992). The most frequently mutated tumor suppressor gene is the p53 gene, mutated in roughly 50% of all tumors. Without a target that is common to all transformed cells, the dream of a "magic bullet" that can destroy or revert cancer cells while leaving normal tissue unharmed is improbable. The hope for a new generation of specifically targeted antitumor drugs may rest on the ability to identify tumor suppressor genes or oncogenes that play general roles in control of cell division.

The tumor suppressor genes, which have been cloned and characterized, influence susceptibility to: 1) retinoblastoma (RB1); 2) Wilms' tumor (WT1); 3) Li-Fraumeni (TP53); 4) Familial adenomatous polyposis (APC); 5) Neurofibromatosis type 1 (NF1); 6) Neurofibromatosis type 2 (NF2); 7) von Hippel-Lindau syndrome (VHL); and 8) Multiple endocrine neoplasia type 2A (MEN2A).

Tumor suppressor loci that have been mapped genetically but not yet isolated include genes for: Multiple endocrine neoplasia type 1 (MEN1); Lynch cancer family syndrome 2 (LCFS2); Familial breast cancer (BRCA1); Neuroblastoma (NB); Basal cell nevus syndrome (BCNS); Beckwith-Wiedemann syndrome (BWS); Renal cell carcinoma (RCC); Tuberous sclerosis 1 (TSC1); and Tuberous sclerosis 2 (TSC2). The tumor suppressor genes that have been characterized to date encode products with similarities to a variety of protein types, including DNA binding proteins (WT1), ancillary transcription regulators (RB1), GTPase activating proteins or GAPs (NF1), cytoskeletal components (NF2), membrane bound receptor kinases (MEN2A), and others with no obvious similarity to known proteins (APC and VHL).

In many cases, the tumor suppressor gene originally identified through genetic studies has been shown in some sporadic tumors to be lost or mutated. This result suggests that regions of chromosomal aberration may signify the position of important tumor suppressor genes involved both in genetic predisposition to cancer and in sporadic cancer.

One of the hallmarks of several tumor suppressor genes characterized to date is that they are deleted at high frequency in certain tumor types. The deletions often involve loss of a single allele, a so-called loss of heterozygosity (LOH), but may also involve homozygous deletion of both alleles. For LOH, the remaining allele is presumed to be nonfunctional, either because of a preexisting inherited mutation, or because of a secondary sporadic mutation. Whereas LOH events commonly involve chromosomal deletions spanning many megabases of DNA, homozygous deletions are relatively small in size, probably due to the presence of essential genes in their proximity. Indeed, the identification of tumor suppressor genes has been facilitated by the discovery of homozygous deletions present within the genomes of cancer cell lines and xenografts; examples include p16 (Kamb et al., 1994), DPC4 (Hahn et al., 1996), BRCA2 (Wooster et al., 1995; Tavtigian et al., 1996) and MMAC1/PTEN(Steck et al., 1997; Li et al., 1997).

Melanoma is a common cancer afflicting one in every hundred Americans (American Cancer Society, 1992). Environmental influences, such as exposure to ultraviolet light, play a large role in melanoma incidence, but heredity is also a contributing factor. A gene for familial melanoma, MLM, has been mapped to chromosome 9p21 (Cannon-Albright et al., 1992; Nancarrow et al., 1993; Gruis et al., 1993; Goldstein et al., 1994). Possession of a single predisposing allele at the MLM locus increases the probability that an individual will develop melanoma by up to approximately 50-fold. MLM belongs to the growing family of suspected tumor suppressor genes. Predisposition to melanoma is inherited as a dominant Mendelian trait, yet predisposing mutations in MLM are thought to act as somatic recessive alleles in the manner originally proposed by Knudson (1971). In a predisposed individual who carries one wild-type and one mutant MLM allele, dividing cells undergo secondary mutational events that involve loss or inactivation of the wild-type copy of MLM, thereby uncovering the inherited mutant MLM allele. Conversely, a single wild-type copy of the gene prevents the onset of malignancy.

Chromosomal aberrations in the vicinity of MLM at 9p21 have been extensively characterized in several different tumor types, including glioma cell lines, non-small cell lung lines and acute lymphoblastic leukemia lines (Olopade et al., 1992; Olopade et al., 1993; Lukeis et al., 1990; Diaz et al., 1988; Middleton et al., 1991; Fountain et al., 1992; Cheng et al., 1993; James et al., 1993). Thus, based on the frequency of 9p21 chromosomal abnormalities in non-melanoma tumor cells, it is probable the MLM region contains a gene (or genes) that participates at least in the progression of several different tumor types. These events involve LOH as well as a high frequency of homozygous deletion.

Cells in tissues have only three serious options in life—they can grow and divide, not grow but stay alive, or die by apoptosis. Tumors may arise either by inappropriate growth and division or by cells failing to die when they should. One of the mechanisms for controlling tumor growth might involve direct regulation of the cell cycle. For example, genes that control the decision to initiate DNA replication are attractive candidates for oncogenes or tumor suppressor genes, depending on whether they have a stimulatory or inhibitory role in the process. Progression of eukaryotic cells through the cell cycle ($G_1$, S, $G_2$ and M phases) is governed by the sequential formation, activation and subsequent inactivation of a series of cyclin/cyclin-dependent kinase (Cdk) complexes. Cyclin D's/Cdk2,4,5, Cyclin E/Cdk2, Cyclin A/Cdk2 and Cyclin B/A/Cdk2 have been shown to be involved in this process. Cyclin D's and Cdk2, Cdk4 and Cdk5 have been implicated in the transition from $G_1$ to S; that is, when cells grow and decide whether to begin DNA replication. Additional cell cycle control elements have recently been discovered. These elements are inhibitors of Cdks (Cdk inhibitors, CkI), and include Far1, p21, p40, p20 and p16 (Marx, 1994; Nasmyth & Hunt, 1993).

Recently, several oncogenes and tumor suppressor genes have been found to participate directly in the cell cycle. For example, one of the cyclins (proteins that promote DNA replication) has been implicated as an oncogene (Motokura et al., 1991; Lammie et al., 1991; Withers et al., 1991; Rosenberg et al., 1991), and tumor suppressor Rb interacts with the primary cyclin-binding partners, the Cdks (Ewen et al., 1993). Identification of a melanoma susceptibility locus would open the way for genetic screening of individuals to assess, for example, the increased risk of cancer due to sunlight exposure. A family of multiple tumor suppressor (MTS) genes has also been found and studied (Kamb et al., 1994; Liu et al., 1995b; Jiang et al., 1995; Stone et al., 1995a; Stone et al., 1995b; Gruis et al., 1995; Liu et al., 1995a; Hannon and Beach, 1994; Serrano et al., 1993). The MTS may also predispose to a large number of other cancer sites, including but not limited to, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum. In addition, since MTS influences progression of several different tumor types, it should be useful for determining prognosis in cancer patients. Thus, MTS may serve as the basis for development of very important diagnostic tests, one capable of predicting the predisposition to cancer, such as melanoma, ocular melanoma, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum, and one capable of predicting the prognosis of cancer. Furthermore, since MTS is involved in the progression of multiple tumor types, MTS may provide the means, either directly or indirectly, for a general anti-cancer therapy by virtue of its ability to suppress tumor growth. For example, restoration of the normal MTS function to a tumor cell may transmute the cell into non-malignancy.

Mitogen-activated protein kinases (MAPKs) function in signal transduction pathways that are involved in controlling key cellular processes in many organisms. Several MAPKKK-MAPKK-MAPK pathways have been identified in mammals (Waskiewicz and Cooper, 1995; Kyriakis and Avruch, 1996). Stimulation of these MAPK pathways by different extracellular factors or environmental stresses results in the downstream regulation of transcription factors that elicit appropriate cellular responses. A mammalian member of this kinase family, MKK4/JNKK1/SEK1, has been reported to link upstream MEKK1 to downstream SAPK/JNK1 and p38 MAP kinase (Derijard et al., 1995; Lin et al., 1995; Yan et al., 1994). This MAPK pathway has been implicated in the signal transduction of cytokine- and stress-induced apoptosis in a variety of cell types (Xia et al., 1995; Chen et al., 1996; Johnson et al., 1996; Verheij et al., 1996; Cuvillier et al., 1996).

Just as the MTS genes appear to be involved in suppressing several types of tumors, the MKK4 gene of the present invention also is involved in suppressing a variety of tumors. Although the MKK4 gene was previously known (Lin et al., 1995; Dérijard et al., 1995), the association between MKK4 and tumor formation was unknown prior to the present work. It was recognized that MKK4 is a dual specific kinase that activates Jun kinases (JNKs) but not extracellular signal-regulated kinases (ERKs) which are a subgroup of mitogen-activated protein kinases (MAPKs). Besides activating JNKs it was known that MKK4 activates p38 which is another MAPK. The JNK and p38 MAPKs are activated by dual phosphorylation on threonine and tyrosine and are part of signal transduction pathways. The present work has uncovered mutations in MKK4 in breast tumor cell lines, pancreatic tumor cell lines, a colorectal tumor cell line and a testis tumor cell line.

SUMMARY OF THE INVENTION

The present invention relates to somatic mutations in the MKK4 gene in human cancers and their use in the diagnosis and prognosis of human cancer. The invention further relates to germline mutations in the MKK4 gene and their use in the diagnosis of predisposition to several cancers, such as breast, pancreatic, colorectal and testicular. The invention also relates to the therapy of human cancers which result from having a mutation in the MKK4 gene, including gene therapy, protein replacement therapy and protein mimetics. Finally, the invention relates to the screening of drugs for cancer therapy.

BRIEF DESCRIPTION OF THE DRAWINGS

Figure 1:
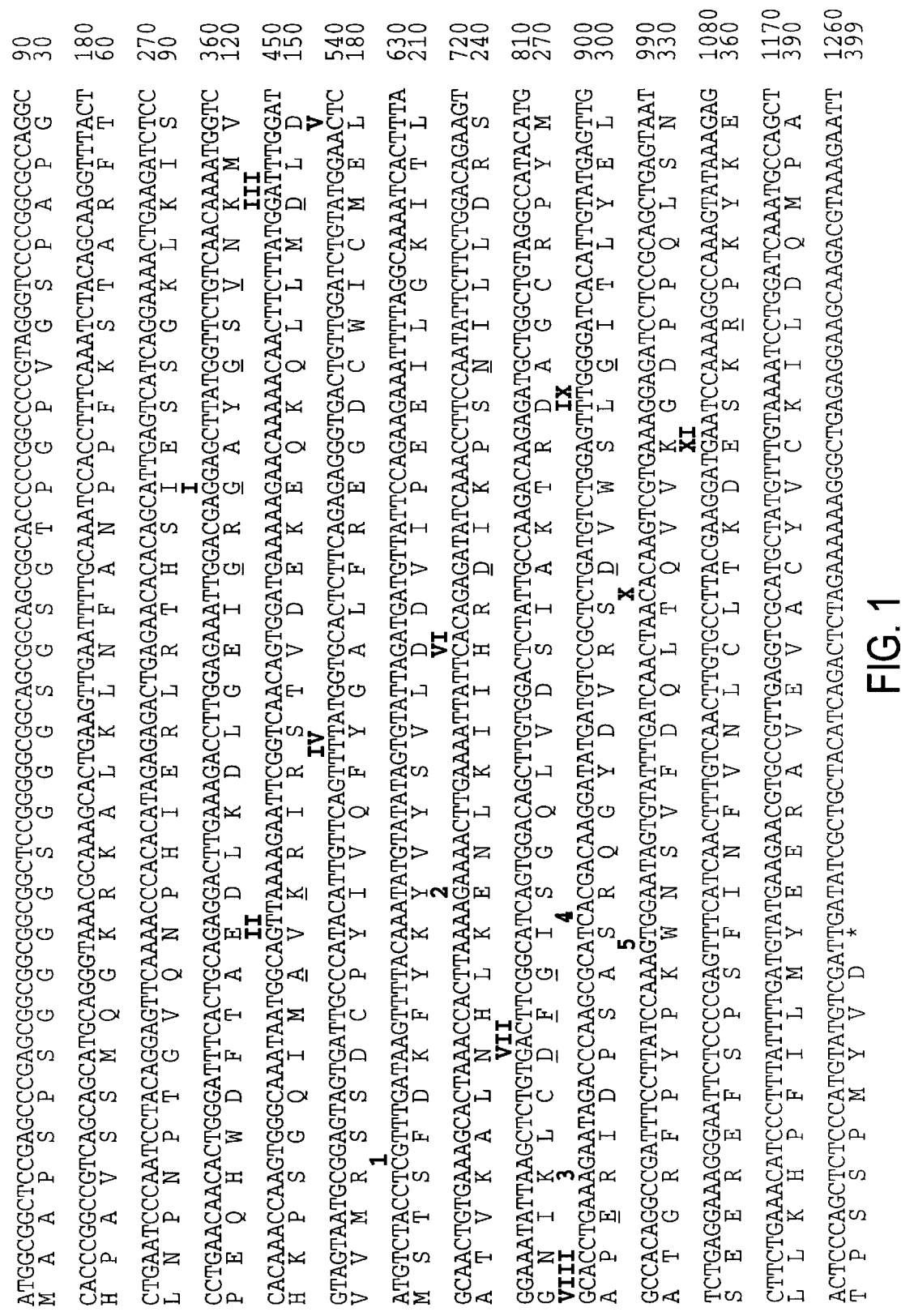

FIG. 1 shows the nucleotide sequence of the MKK4 cDNA and its predicted polypeptide product. The nucleotide sequence corresponds to bases 21–1280 of SEQ ID NO:91 and the amino acid sequence corresponds to SEQ ID NO:92, Subdomains I–XI conserved among protein kinases are indicated; underlined amino acids highlight critical residues that are invariantly or highly conserved among SER/THR and TYR protein kinases. Bold numbers mark the locations of the tumor cell line mutations: (1) C to T transition (SER→LEU) in the breast cell line, MDA-MB-134-VI; (2) G to T mutation (GLU→STOP) in the pancreatic cell line, CAPAN-1; (3) A→G transition (ARG→GLY) in the colon cell line, SW 1417; (4) C to A alteration (SER→STOP) in the breast cell line, MDA-MB-415; and (5) G to C transversion (LYS→ASN) in the testis cell line, NCCIT.

FIG. 3D is an autoradiograph of kinase inactive SAPK-β K55R (Sanchez et al., 1994) after phosphorylation by HA-MKK4 immunoprecipitates; these differentially expressed altered MKK4 products were normalized prior to assay. FIG. 3E shows the $^{32}$P-labeled SAPK-β K55R activity of bands which were excised and quantified by scintillation counting. The data shown are expressed as a percentage of WT-MKK4 (taken to be 100%) and reflect the average of two independent sets of kinase assays.

DETAILED DESCRIPTION OF THE INVENTION

Figure 2A:
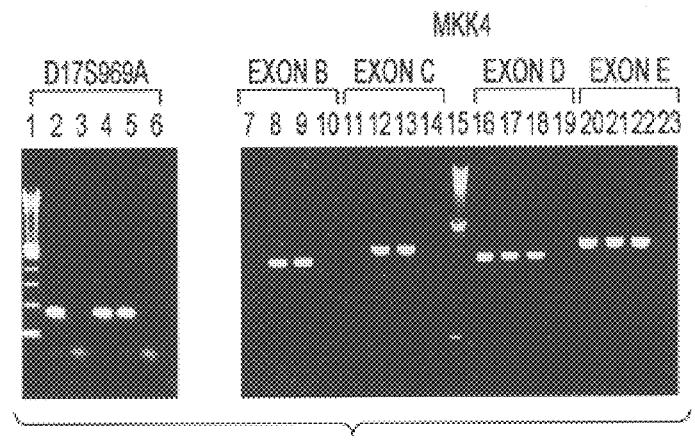
FIG. 2A shows evidence of a homozygous deletion in a pancreatic cancer cell line, ASPC-1. Shown is the D17S969A STS when it was used to examine genomic DNAs from the following: 2) control human (Promega); 3) ASPC-1; 4) COLO 587, a pancreatic cancer cell line; 5) HPAF-II, a pancreatic cancer cell line; 6) negative control (lacking template). In addition, mutation screening primers designed to amplify exons B, C, D and E, of the MKK4 gene (Table 4), were used to examine genomic DNA from ASPC-1 (lanes 7, 11, 16, 20), CAPAN-1 (lanes 8, 12, 17, 21), control human (Promega; lanes 9, 13, 18, 22) and a control without template (lanes 10, 14, 19, 23). Lanes 1 and 15 show a 100 basepair DNA ladder (Gibco BRL).

The present invention relates to somatic mutations in the MKK4 gene in human cancers and their use in the diagnosis and prognosis of human cancer. The invention further relates to germline mutations in the MKK4 gene and their use in the diagnosis of predisposition to various cancers, such as breast, pancreatic, colorectal and testicular. The invention also relates to the therapy of human cancers which have a mutation in the MKK4 gene, including gene therapy, protein replacement therapy and protein mimetics. Finally, the invention relates to the screening of drugs for cancer therapy.

The present invention provides an isolated polynucleotide comprising all, or a portion of the MKK4 locus or of a mutated MKK4 locus, preferably at least eight bases and not more than about 100 kb in length. Such polynucleotides may be antisense polynucleotides. The present invention also provides a recombinant construct comprising such an isolated polynucleotide, for example, a recombinant construct suitable for expression in a transformed host cell.

Also provided by the present invention are methods of detecting a polynucleotide comprising a portion of the MKK4 locus or its expression product in an analyte. Such methods may further comprise the step of amplifying the portion of the MKK4 locus, and may further include a step of providing a set of polynucleotides which are primers for amplification of said portion of the MKK4 locus. The method is useful for either diagnosis of the predisposition to cancer or the diagnosis or prognosis of cancer.

The present invention also provides isolated antibodies, preferably monoclonal antibodies, which specifically bind to an isolated polypeptide comprised of at least five amino acid residues encoded by the MKK4 locus.

The present invention also provides kits for detecting in an analyte a polynucleotide comprising a portion of the MKK4 locus, the kits comprising a polynucleotide complementary to the portion of the MKK4 locus packaged in a suitable container, and instructions for their use.

The present invention further provides methods of preparing a polynucleotide comprising polymerizing nucleotides to yield a sequence comprised of at least eight consecutive nucleotides of the MKK4 locus; and methods of preparing a polypeptide comprising polymerizing amino acids to yield a sequence comprising at least five amino acids encoded within the MKK4 locus.

In addition, the present invention provides methods of screening drugs for cancer therapy to identify suitable drugs for restoring MKK4 gene product function.

Finally, the present invention provides the means necessary for production of gene-based therapies directed at cancer cells. These therapeutic agents may take the form of polynucleotides comprising all or a portion of the MKK4 locus placed in appropriate vectors or delivered to target cells in more direct ways such that the function of the MKK4 protein is reconstituted. Therapeutic agents may also take the form of polypeptides based on either a portion of, or the entire protein sequence of MKK4. These may functionally replace the activity of MKK4 in vivo.

It is a discovery of the present invention that the MKK4 locus (referred to in the prior art as MKK4 or JNKK) predisposes individuals to breast, pancreatic, colorectal and testicular cancers. The MKK4 locus was first recognized as containing a tumor suppressor gene when it was noted to be part of a homozygous deletion in a pancreatic tumor cell line called ASPC-1. Subsequently, many tumor cell lines were screened for loss of heterozygosity (LOH) within the MKK4 locus and mutations within MKK4 were found in five cell lines which were hemizygous for this locus. Two nonsense and three missense sequence variants of MKK4 were found in lines derived from human pancreatic, breast, colon and testis cells. In vitro biochemical assays revealed that, when stimulated by MEKK1, four of the five altered MKK4 proteins lacked the ability to phosphorylate SAPK. Also, homozygous deletions that eliminated coding portions of the MKK4 locus at 17p, located approximately 10 cM centromeric of P53 were discovered in two human tumor cell lines derived from pancreatic carcinoma and lung carcinoma.

According to the diagnostic and prognostic method of the present invention, alteration of the wild-type MKK4 locus is detected. In addition, the method can be performed by detecting the wild-type MKK4 locus and confirming the lack of a predisposition or neoplasia. "Alteration of a wild-type gene" encompasses all forms of mutations including deletions, insertions and point mutations in the coding and noncoding regions. Deletions may be of the entire gene or only a portion of the gene. Point mutations may result in stop codons, frameshift mutations or amino acid substitutions. Somatic mutations are those which occur only in certain tissues, e.g., in the tumor tissue, and are not inherited in the germline. Germline mutations can be found in any of a body's tissues and are inherited. If only a single allele is somatically mutated, an early neoplastic state is indicated. However, if both alleles are mutated, then a late neoplastic state is indicated. The finding of MKK4 mutations thus provides both diagnostic and prognostic information. A MKK4 allele which is not deleted (e.g., that found on the sister chromosome to a chromosome carrying a MKK4 deletion) can be screened for other mutations, such as insertions, small deletions, and point mutations. It is believed that many mutations found in tumor tissues will be those leading to decreased expression of the MKK4 gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the MKK4 gene product, or a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below. Also useful is the recently developed technique of DNA microchip technology.

Predisposition to cancers, such as breast and the other cancers identified herein, can be ascertained by testing any tissue of a human for mutations of the MKK4 gene. For example, a person who has inherited a germline MKK4 mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells or amniotic fluid for mutations of the MKK4 gene. Alteration of a wild-type MKK4 allele, whether, for example, by point mutation or by deletion, can be detected by any of the means discussed herein.

In order to detect the alteration of the wild-type MKK4 gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These techniques, as well as other techniques for separating tumor cells from normal cells, are well known in the art. If the tumor tissue is highly contaminated with normal cells, detection of mutations is more difficult.

A rapid preliminary analysis to detect polymorphisms in DNA sequences can be performed by looking at a series of Southern blots of DNA cut with one or more restriction enzymes, preferably a large number of restriction enzymes. Each blot contains a series of normal individuals and a series of cancer cases, tumors, or both. Southern blots displaying hybridizing fragments (differing in length from control DNA when probed with sequences near or including the MKK4 locus) indicate a possible mutation. If restriction enzymes which produce very large restriction fragments are used, then pulsed field gel electrophoresis ("PFGE") is employed.

Detection of point mutations may be accomplished by molecular cloning of the MKK4 allele and sequencing that allele using techniques well known in the art. Alternatively, the gene sequences can be amplified, using known techniques, directly from a genomic DNA preparation from the tumor tissue. The DNA sequence of the amplified sequences can then be determined.

There are six well known methods for a more complete, yet still indirect, test for confirming the presence of a susceptibility allele: 1) single stranded conformation analysis ("SSCA") (Orita et al., 1989); 2) denaturing gradient gel electrophoresis ("DGGE") (Wartell et al., 1990; Sheffield et al., 1989); 3) RNase protection assays (Finkelstein et al., 1990; Kinszler et al., 1991); 4) allele-specific oligonucleotides ("ASOs") (Conner et al., 1983); 5) the use of proteins which recognize nucleotide mismatches, such as the E. coli mutS protein (Modrich, 1991); and 6) allele-specific PCR (Rano and Kidd, 1989). For allele-specific PCR, primers are used which hybridize at their 3' ends to a particular MKK4 mutation. If the particular MKK4 mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the MKK4 mutation found in that individual. Other techniques for detecting insertions and deletions as known in the art can be used.

In the first three methods (i.e., SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type MKK4 gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the MKK4 mRNA or gene but can be a segment of either. If the riboprobe comprises only a segment of the MKK4 mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the MKK4 gene can also be detected using Southern hybridization, especially if the changes are gross rearrangements, such as deletions and insertions.

DNA sequences of the MKK4 gene which have been amplified by use of PCR may also be screened using allele-specific probes. These probes are nucleic acid oligomers, each of which contains a region of the MKK4 gene sequence harboring a known mutation. For example, one oligomer may be about 30 nucleotides in length, corresponding to a portion of the MKK4 gene sequence. By use of a battery of such allele-specific probes, PCR amplification products can be screened to identify the presence of a previously identified mutation in the MKK4 gene. Hybridization of allele-specific probes with amplified MKK4 sequences can be performed, for example, on a nylon filter. Hybridization to a particular probe under stringent hybridization conditions indicates the presence of the same mutation in the tumor tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996).

The most definitive test for mutations in a candidate locus is to directly compare genomic MKK4 sequences from cancer patients with those from a control population. Alternatively, one could sequence messenger RNA after amplification, e.g., by PCR, thereby eliminating the necessity of determining the exon structure of the candidate gene.

Mutations from cancer patients falling outside the coding region of MKK4 can be detected by examining the non-coding regions, such as introns and regulatory sequences near or within the MKK4 gene. An early indication that mutations in noncoding regions are important may come from Northern blot experiments that reveal messenger RNA molecules of abnormal size or abundance in cancer patients as compared to control individuals.

Alteration of MKK4 mRNA expression can be detected by any techniques known in the art. These include Northern blot analysis, PCR amplification, RNase protection and the microchip method discussed above. Diminished mRNA expression indicates an alteration of the wild-type MKK4 gene. Alteration of wild-type MKK4 genes can also be detected by screening for alteration of wild-type MKK4 protein. For example, monoclonal antibodies immunoreactive with MKK4 can be used to screen a tissue. Lack of cognate antigen would indicate a MKK4 mutation. Antibodies specific for products of mutant alleles could also be used to detect mutant MKK4 gene product. Such immunological assays can be done in any convenient formats known in the art. These include Western blots, immunohistochemical assays and ELISA assays. Any means for detecting an altered MKK4 protein can be used to detect alteration of wild-type MKK4 genes. Functional assays can be used. For example, it is known that MKK4 protein is a kinase which is reactive with p38 and JNK (Dérijard et al., 1995). Thus, an assay for the ability to phosphorylate these proteins can be employed. Finding a mutant MKK4 gene product indicates alteration of a wild-type MKK4 gene.

Mutant MKK4 genes or gene products can also be detected in other human body samples, such as serum, stool, urine and sputum. The same techniques discussed above for detection of mutant MKK4 genes or gene products in tissues can be applied to other body samples. Cancer cells are sloughed off from tumors and appear in such body samples. In addition, the MKK4 gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant MKK4 genes or gene products.

The methods of diagnosis of the present invention are applicable to any tumor in which MKK4 has a role in tumorigenesis. The diagnostic method of the present invention is useful for clinicians, so they can decide upon an appropriate course of treatment.

The primer pairs of the present invention are useful for determination of the nucleotide sequence of a particular MKK4 allele using the PCR. The pairs of single-stranded DNA primers can be annealed to sequences within or surrounding the MKK4 gene in order to prime amplifying DNA synthesis of the MKK4 gene itself. A complete set of these primers allows synthesis of all of the nucleotides of the MKK4 gene coding sequences, i.e., the exons. The set of primers preferably allows synthesis of both intron and exon sequences. Allele-specific primers can also be used. Such primers anneal only to particular MKK4 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from MKK4 sequences or sequences adjacent to MKK4, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of MKK4 shown in SEQ ID NOs:36–46 (genomic) and SEQ ID NO:91 (cDNA) design of particular primers is well within the skill of the art.

The nucleic acid probes provided by the present invention are useful for a number of purposes. They can be used in Southern hybridization to genomic DNA and in the RNase protection method for detecting point mutations. The probes can be used to detect PCR amplification products. They may also be used to detect mismatches with the MKK4 gene or mRNA using other techniques.

Definitions

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis et al., 1990 (for PCR); and Wu et al., 1989a (for LCR). Reagents and hardware for conducting PCR are commercially available. Primers useful to amplify sequences from the MKK4 region are preferably complementary to, and hybridize specifically to, sequences in the MKK4 region or in regions that flank a target region therein. MKK4 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the MKK4 polypeptides and fragments thereof or to polynucleotide sequences from the MKK4 region, particularly from the MKK4 locus or a portion thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the MKK4 polypeptide or fragment. Monoclonal antibodies may be made by injecting mice with the protein polypeptides, fusion proteins or fragments thereof. Monoclonal antibodies will be screened by ELISA and tested for specific immunoreactivity with MKK4 polypeptide or fragments thereof. See, Harlow & Lane, 1988, These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art.

For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. The polynucleotides may be composed of DNA, RNA, or synthetic nucleotide analogs.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

As used herein, the terms "diagnosing" or "prognosing," as used in the context of neoplasia, are used to indicate 1) the classification of lesions as neoplasia, 2) the determination of the severity of the neoplasia, or 3) the monitoring of the disease progression, prior to, during and after treatment.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"MKK4 Allele" refers to normal alleles of the MKK4 locus as well as alleles carrying variations that predispose individuals to develop cancer of many sites including, for example, breast, pancreatic, colorectal and testicular cancers. Such predisposing alleles are also called "MKK4 susceptibility alleles".

"MKK4 Locus," "MKK4 gene," "MKK4 Nucleic Acids" or "MKK4 Polynucleotide" refers to polynucleotides, all of which are in the MKK4 region, that are likely to be expressed in normal tissue, certain alleles of which predispose an individual to develop breast, pancreatic, colorectal or testicular cancer. The MKK4 locus is used interchangeably herein with the prior art designation MKK4 or JNKK locus. Mutations at the MKK4 locus may be involved in the initiation and/or progression of other types of tumors. The locus is indicated in part by mutations that predispose individuals to develop cancer. These mutations fall within the MKK4 region described infra. The MKK4 locus is intended to include coding sequences, intervening sequences and regulatory elements controlling transcription and/or translation. The MKK4 locus is intended to include all allelic variations of the DNA sequence.

These terms, when applied to a nucleic acid, refer to a nucleic acid which encodes a MKK4 polypeptide, fragment, homolog or variant, including, e.g., protein fusions or deletions. The nucleic acids of the present invention will possess a sequence which is either derived from, or substantially similar to, a natural MKK4-encoding gene or one having substantial homology with a natural MKK4-encoding gene or a portion thereof. The cDNA for MKK4 is shown in SEQ ID NO:91 and the encoded polypeptide sequence is given as SEQ ID NO:92.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the MKK4 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered, e.g., by deletion, substitution or insertion.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a MKK4-encoding sequence.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega Biotech, U. S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, the terms "MKK4 locus," "MKK4 allele" and "MKK4 region" all refer to the double-stranded DNA comprising the locus, allele, or region, as well as either of the single-stranded DNAs comprising the locus, allele or region.

As used herein, a "portion" of the MKK4 locus or region or allele is defined as having a minimal size of at least about eight nucleotides, or preferably about 15 nucleotides, or more preferably at least about 25 nucleotides, and may have a minimal size of at least about 40 nucleotides.

"MKK4 protein" or "MKK4 polypeptide" refers to a protein or polypeptide encoded by the MKK4 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native MKK4 sequence, preferably in excess of about 90%, and more preferably at least about 95% homologous. Also included are proteins encoded by DNA which hybridize under high or low stringency conditions, to MKK4-encoding nucleic acids and closely related polypeptides or proteins retrieved by antisera to the MKK4 protein.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

"Probes". Polynucleotide polymorphisms associated with MKK4 alleles which predispose to certain cancers or are associated with most cancers are detected by hybridization with a polynucleotide probe which forms a stable hybrid with that of the target sequence, under stringent to moderately stringent hybridization and wash conditions. If it is expected that the probes will be perfectly complementary to the target sequence, stringent conditions will be used. Hybridization stringency may be lessened if some mismatching is expected, for example, if variants are expected with the result that the probe will not be completely complementary. Conditions are chosen which rule out nonspecific/ adventitious bindings, that is, which minimize noise. Since such indications identify neutral DNA polymorphisms as well as mutations, these indications need further analysis to demonstrate detection of a MKK4 susceptibility allele.

Probes for MKK4 alleles may be derived from the sequences of the MKK4 region or its cDNAs. The probes may be of any suitable length, which span all or a portion of the MKK4 region, and which allow specific hybridization to the MKK4 region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 Kb, usually fewer than about 1.0 Kb, from a polynucleotide sequence encoding MKK4 are preferred as probes. The probes may also be used to determine whether mRNA encoding MKK4 is present in a cell or tissue.

"Protein modifications or fragments" are provided by the present invention for MKK4 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands, which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See, e.g., Sambrook et al., 1989 or Ausubel et al., 1992.

Besides substantially full-length polypeptides, the present invention provides for biologically active fragments of the polypeptides. Significant biological activities include kinase activity, immunological activity and other biological activities characteristic of MKK4 polypeptides. Immunological activities include both immunogenic function in a target immune system, as well as sharing of immunological epitopes for binding, serving as either a competitor or substitute antigen for an epitope of the MKK4 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for MKK4 polypeptides or fragments thereof is described below.

The present invention also provides for fusion polypeptides, comprising MKK4 polypeptides and fragments. Homologous polypeptides may be fusions between two or more MKK4 polypeptide sequences or between the sequences of MKK4 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See, e.g., Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the MKK4 polypeptides from other biological material, such as from cells transformed with recombinant nucleic acids encoding MKK4, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis or a protein sample, followed by visualizing a single polypeptide band upon staining the gel. For certain purposes, higher resolution may be provided by using HPLC or other means well known in the art for purification utilized.

A MKK4 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 10 Kb of the coding region of a locus which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. See, e.g., Wetmur & Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, and preferably at least about 95% identity.

"Substantially similar function" refers to the function of a modified nucleic acid or a modified protein, with reference to the wild-type MKK4 nucleic acid or wild-type MKK4 polypeptide. The modified polypeptide will be substantially homologous to the wild-type MKK4 polypeptide and will have substantially the same function, i.e., the phosphorylation of JNK and p38. The modified polypeptide may have an altered amino acid sequence and/or may contain modified amino acids. In addition to the function of phosphorylating JNK and p38, the modified polypeptide may have other useful properties, such as a longer half-life. The kinase activity of the modified polypeptide may be substantially the same as the activity of the wild-type MKK4 polypeptide. Alternatively, the kinase activity of the modified polypeptide may be higher or lower than the activity of the wild-type MKK4 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type MKK4 gene function produces the modified protein described above.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measure of homology assigned to various substitutions, deletions, substitutions, and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping is provided, e.g., in White and Lalouel, 1988.

Preparation of Recombinant or Chemically Synthesized Nucleic Acids; Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage & Carruthers, 1981 or the triester method according to Matteucci et al., 1981, and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate which allow the protein to cross and/or lodge in cell membranes or be secreted from the cell. Such vectors may be prepared by means of standard recombinant techniques well known in the art and discussed, for example, in Sambrook et al., 1989 or Ausubel et al. 1992.

The selection of an appropriate promoter and other necessary vector sequences will be selected so as to be functional in the host, and may include, when appropriate, those naturally associated with MKK4 genes. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine molony leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983).

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, T. Kubo et al., 1988), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the MKK4 nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), 1979. Examples of commonly used mammalian host cell lines are VERO and HeLa cells, Chinese hamster ovary (CHO) cells, and W138, BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of MKK4 polypeptides.

Antisense polynucleotide sequences are useful in preventing or diminishing the expression of the MKK4 locus, as will be appreciated by those skilled in the art. For example, polynucleotide vectors containing all or a portion of the MKK4 locus or other sequences from the MKK4 region (particularly those flanking the MKK4 locus) may be placed under the control of a promoter in an antisense orientation and introduced into a cell. Expression of such an antisense construct within a cell will interfere with MKK4 transcription and/or translation and/or replication.

Methods of Use: Nucleic Acid Diagnosis and Diagnostic Kits

In order to detect the presence of a MKK4 allele predisposing an individual to cancer, a biological sample such as blood is prepared and analyzed for the presence or absence of susceptibility alleles of MKK4. In order to detect the presence of neoplasia, the progression toward malignancy of a precursor lesion, or as a prognostic indicator, a biological sample of the lesion is prepared and analyzed for the presence or absence of neoplastic alleles of MKK4. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant MKK4 sequences, e.g., by PCR, followed by DNA sequence analysis. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mittlin, 1989; U.S. Pat. No. 4,868,105; and in EPO Publication No. 225,807.

Non-PCR based screening assays are also contemplated in this invention. An exemplary non-PCR based procedure is provided in Example 7. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al., 1986.

Two-step label amplification methodologies are known in the art. These assays work on the principle that a small ligand (such as digoxigenin, biotin, or the like) is attached to a nucleic acid probe capable of specifically binding MKK4. Allele specific probes are also contemplated within the scope of this example and exemplary allele specific probes include probes encompassing the mutations summarized in Table 5.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby, et al., 1977 and Nguyen, et al. (1992).

It is also contemplated within the scope of this invention that the nucleic acid probe assays will employ a cocktail of nucleic acid probes capable of detecting MKK4 genes. Thus, in one example to detect the presence of MKK4 in a cell sample, more than one probe complementary to MKK4 is employed and in particular the number of different probes is alternatively 2, 3, or 5 different nucleic acid probe sequences. In another example, to detect the presence of mutations in the MKK4 gene sequence in a patient, more than one probe complementary to MKK4 is employed where the cocktail includes probes capable of binding to the allele-specific mutations identified in populations of patients with alterations in MKK4. In this embodiment, any number of probes can be used. Some candidate probes contemplated within the scope of the invention include probes that include the allele-specific mutations identified in Table 5.

It is further contemplated within the scope of this invention that the nucleic acid probe assays of this invention will employ the recently developed nucleic acid microchip technology which utilizes an array of many thousands of probes bound to a chip to analyze a sample. This method thus analyzes the sample simultaneously using all of the probes which are bound to the microchip. For published examples of this technology see Hacia et al., 1996; Shoemaker et al., 1996; Chee et al., 1996; Lockhart et al., 1996; DeRisi et al., 1996; Lipshutz et al., 1995.

Methods of Use: Peptide Diagnosis and Diagnostic Kits

The neoplastic condition of lesions can also be detected on the basis of the alteration of wild-type MKK4 polypeptide. Such alterations can be determined by sequence analysis in accordance with conventional techniques. More preferably, antibodies (polyclonal or monoclonal) are used to detect differences in or the absence of MKK4 peptides. In a preferred embodiment of the invention, antibodies will immunoprecipitate MKK4 proteins from solution as well as react with MKK4 protein on Western or immunoblots of polyacrylamide gels. In another preferred embodiment, antibodies will detect MKK4 proteins in paraffin or frozen tissue sections, using immunocytochemical techniques. Techniques for raising and purifying antibodies are well known in the art, and any such techniques may be chosen to achieve the preparation of the invention.

Preferred embodiments relating to methods for detecting MKK4 or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference, and exemplified in Example 10.

Methods of Use: Drug Screening

The present invention is particularly useful for screening compounds by using the p38 or JNK polypeptides or fragments thereof in any of a variety of drug screening techniques. Preferably, p38 is utilized. The p38 or JNK polypeptide or fragment employed in such a test may either be free in solution, affixed to a solid support, or borne on a cell surface. One method of drug screening measures the phosphorylation of p38 or JNK by MKK4. One may measure, for example, to what extent the kinase activity of MKK4 is enhanced, or possibly inhibited, by the agent being tested.

Methods of Use: Rational Drug Design

The goal of rational drug design is to produce structural analogs of biologically active polypeptides of interest or of small molecules with which they interact (e.g., agonists, antagonists, inhibitors or enhancers) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., MKK4) or, for example, of MKK4-p38 complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., MKK4) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved MKK4 activity or stability or which act as enhancers, inhibitors, agonists, antagonists, etc. of MKK4 activity. By virtue of the availability of cloned MKK4 sequences, sufficient amounts of the MKK4 polypeptide may be made available to perform such analytical studies as x-ray crystallography. In addition, the knowledge of the MKK4 protein sequence provided herein will guide those employing computer modeling techniques in place of, or in addition to x-ray crystallography.

Methods of Use: Gene Therapy

According to the present invention, a method is also provided of supplying wild-type MKK4 function to a cell which carries mutant MKK4 alleles. Supplying such a function should suppress neoplastic growth of the recipient cells. The wild-type MKK4 gene or a part of the gene may be introduced into the cell in a vector such that the gene remains extrachromosomal. In such a situation, the gene will be expressed by the cell from the extrachromosomal location. If a gene portion is introduced and expressed in a cell carrying a mutant MKK4 allele, the gene portion should encode a part of the MKK4 protein which is required for non-neoplastic growth of the cell. More preferred is the situation where the wild-type MKK4 gene or a part thereof is introduced into the mutant cell in such a way that it recombines with the endogenous mutant MKK4 gene present in the cell. Such recombination requires a double recombination event which results in the correction of the MKK4 gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the routineer. Cells transformed with the wild-type MKK4 gene can be used as model systems to study cancer remission and drug treatments which promote such remission.

As generally discussed above, the MKK4 gene or fragment, where applicable, may be employed in gene therapy methods in order to increase the amount of the expression products of such genes in cancer cells. Such gene therapy is particularly appropriate for use in both cancerous and pre-cancerous cells, in which the level of MKK4 polypeptide is absent or diminished compared to normal cells. It may also be useful to increase the level of expression of a given MKK4 gene even in those tumor cells in which the mutant gene is expressed at a "normal" level, but the gene product is not fully functional.

Gene therapy would be carried out according to generally accepted methods, for example, as described by Friedman in *Therapy for Genetic Disease*, T. Friedman, ed., Oxford University Press (1991), pp. 105–121, Cells from a patient's tumor would be first analyzed by the diagnostic methods described above, to ascertain the production of MKK4 polypeptide in the tumor cells. A virus or plasmid vector, containing a copy of the MKK4 gene linked to expression control elements and capable of replicating inside the tumor cells, is prepared. Suitable vectors are known, such as disclosed in U.S. Pat. No. 5,252,479 and PCT published application WO 93/07282. The vector is then injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990), herpesviruses including HSV and EBV (Margolskee, 1992; Johnson et al., 1992; Fink et al., 1992; Breakfield and Geller, 1987; Freese et al., 1990), and retroviruses of avian (Brandyopadhyay and Temin, 1984; Petropoulos et al., 1992), murine (Miller, 1992; Miller et al., 1985; Sorge et al., 1984; Mann and Baltimore, 1985; Miller et al., 1988), and human (Shimada et al., 1991; Helseth et al., 1990; Page et al., 1990; Buchschacher and Panganiban, 1992) origin. Most human gene therapy protocols have been based on disabled murine retroviruses.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Constantini and Lacy, 1981); membrane fusion-mediated transfer via liposomes (Felgner et al., 1987; Wang and Huang, 1989; Kaneda et al, 1989; Stewart et al., 1992; Nabel et al., 1990; Lim et al., 1992); and direct DNA uptake and receptor-mediated DNA transfer (Wolff et al., 1990; Wu et al., 1991; Zenke et al., 1990; Wu et al., 1989b; Wolff et al., 1991; Wagner et al., 1990; Wagner et al., 1991; Cotten et al., 1990; Curiel et al., 1991a; Curiel et al., 1991b). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Methods of Use: Peptide Therapy

Peptides which have MKK4 activity can be supplied to cells which carry mutant or missing MKK4 alleles. The sequence of the MKK4 protein is disclosed (SEQ ID NO:92). Protein can be produced by expression of the cDNA sequence in bacteria, for example, using known expression vectors. Alternatively, MKK4 polypeptide can be extracted from MKK4-producing mammalian cells. In addition, the techniques of synthetic chemistry can be employed to synthesize MKK4 protein. Any of such techniques can provide the preparation of the present invention which comprises the MKK4 protein. The preparation is substantially free of other human proteins. This is most readily accomplished by synthesis in a microorganism or in vitro.

Active MKK4 molecules can be introduced into cells by microinjection or by use of liposomes, for example. Alternatively, some active molecules may be taken up by cells, actively or by diffusion. Extracellular application of the MKK4 gene product may be sufficient to affect tumor growth. Supply of molecules with MKK4 activity should lead to partial reversal of the neoplastic state. Other molecules with MKK4 activity (for example, peptides, drugs or organic compounds) may also be used to effect such a reversal. Modified polypeptides having substantially similar function are also used for peptide therapy.

Methods of Use: Transformed Hosts

Similarly, cells and animals which carry a mutant MKK4 allele can be used as model systems to study and test for substances which have potential as therapeutic agents. The cells are typically cultured epithelial cells. These may be isolated from individuals with MKK4 mutations, either somatic or germline. Alternatively, the cell line can be engineered to carry the mutation in the MKK4 allele, as described above. After a test substance is applied to the cells, the neoplastically transformed phenotype of the cell is determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant MKK4 alleles, usually from a second animal species, as well as insertion of disrupted homologous genes. Alternatively, the endogenous MKK4 gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the growth of tumors must be assessed. If the test substance prevents or suppresses the growth of tumors, then the test substance is a candidate therapeutic agent for the treatment of the cancers identified herein.

The present invention is described by reference to the following Examples, which are offered by way of illustration and are not intended to limit the invention in any manner. Standard techniques well known in the art or the techniques specifically described below were utilized.

EXAMPLE 1

Identification of a Homozygous Deletion in a Pancreatic Tumor Cell Line

The human pancreatic tumor cell line ASPC-1 was screened with a number of sequence tagged site (STS) probes for homozygous deletions (see Green and Olson (1990) for the use of STSs in genome mapping and see Vollrath et al. (1992) for a method of deletion mapping using STSs). Homozygous deletion searches were performed as follows: Total genomic DNA was purified from cancer cell lines using the Easy-DNA kit (Invitrogen). Using the cell line DNAs as templates, 20 µL PCR amplifications were performed with either TaqPlus (Stratagene) or AmpliTaq Gold (Perkin Elmer) and subsequently fractionated on 2–3% Nu Sieve (FMC Bioproducts) agarose gels. In general, the PCR conditions used were an initial denaturation step at 95° C. for 1 minute (TaqPlus) or 10 minutes (AmpliTaq Gold), followed by 35 cycles of denaturation at 96° C. for 12 seconds, annealing at 55° C. for 15 seconds and extension at 72° C. for 45 seconds. The homozygous deletion of ASPC-1 observed with D17S969 was confirmed by PCR amplifications using several flanking STSs, one of which was D17S969A shown in FIG. 2A. The sequences of the primer pair of the D17S969A STS (173 bp amplicon) are 5'-GAGCCTCAATTCCAGTTTTCC-3' (SEQ ID NO:93) and 5'-TATGATGCAGCACTGCAGTT-3' (SEQ ID NO:94).

Figure 2B:
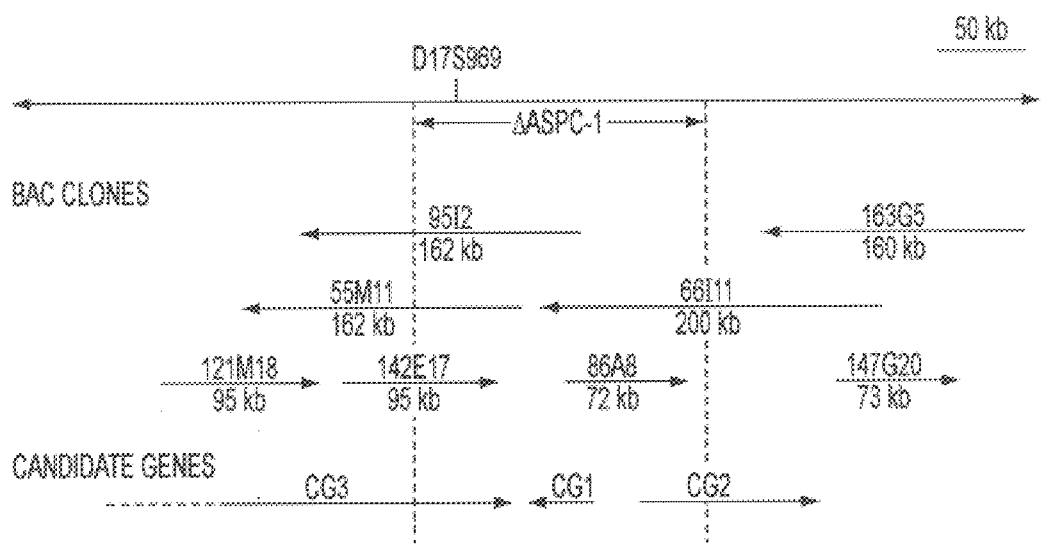
FIG. 2B shows a physical map of the D17S969 genomic region. Shown are the BAC clones and candidate genes isolated for this region. Sizes of the BAC clones, as well as their corresponding T7 (arrowhead) and SP6 ends, are indicated. The three candidate genes were localized on BACs and their directions of transcription were determined by STS mapping and DNA sequencing. The dashed line in the 5' portion of CG3 indicates that the gene extends upstream into a genomic area not characterized in this study. The extent of the homozygous deletion in the ASPC-1 pancreatic carcinoma cell line is shown.
Figure 3A:
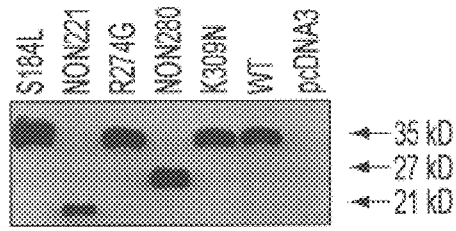
FIGS. 3A–3E show expression and activity of the MKK4 variants. Human kidney 293 cells were cotransfected with pcDNA3-Flag-MEKK1Δ and pcDNA3-HA-MKK4 (wild type or altered), or pcDNA3-Flag-MEKK1Δ and pcDNA3 vector as a control. The variant forms investigated are S184L-MKK4 of breast MDA-MB-134-VI, NON221-MKK4 of pancreatic CAPAN-1, R274G-MKK4 of colon SW1417, NON280-MKK4 of breast MDA-MB-415, and K309N-MKK4 of testis NCCIT. Shown are Western blots of the pellet (insoluble) (FIG. 3A) and supernatant (soluble) (FIG. 3B) fractions of the transfected cell lysates probed with anti-HA antibodies; a non-specific immunoreactive band is observed at ~37 kDa. For FIG. 3C, the supernatant fractions were also probed with anti-Flag antibodies to confirm equivalent expression of MEKK1Δ among the different transfected cells.
Figure 3B:
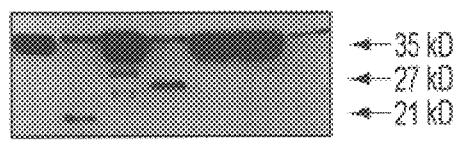
Figure 3C:
Figure 3D:
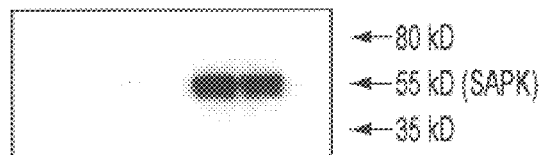
Figure 3E:
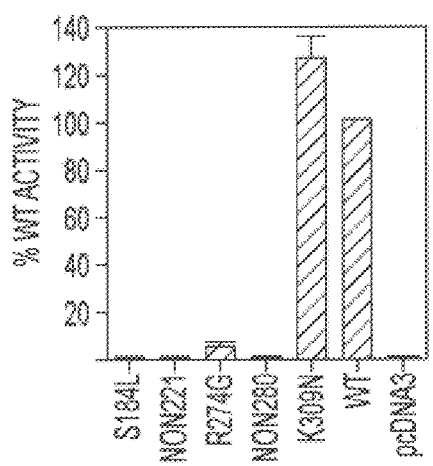

Such a homozygous deletion was first identified by the present work in the ASPC-1 cell line by an STS named D17S969 (see Table 1 and FIGS. 2A–B). The deletion was in a region reported to exhibit a high frequency of LOH in colorectal cancers (Vogelstein et al., 1989). Bacterial artificial chromosomes (BACs) containing human genomic DNA were screened and a BAC genomic contig across the deleted region was assembled which centers on two BACs—66I11 and 95I2.

BAC DNA was purified and directly sequenced as described (Rommens et al., 1995; Couch et al., 1996). DNA sequences at the SP6 and T7 ends of isolated BAC clones were used to develop STSs that were employed for mapping. To obtain greater than 90% sequence coverage of BACs 95I2 and 66I11, plasmid sub-libraries generated from these clones were sequenced using ABI377 machines. The sequence data obtained were assembled into contiguous segments using Acembly Version 4.3 (U. Sauvage, D. Thierry-Mieg and J. Thierry-Mieg; CNRS, France). The generation of cDNAs and hybrid selection were done as previously described (Rommens et al., 1995; Couch et al., 1996). Hybrid selection was performed on a pool of cDNAs from normal human lymphocytes, pancreas, prostate, thymus and fetal brain tissues.

TABLE 1

LOH Analyses of Cancer Cell Lines

| Type of Cell Line | Number LOH/Screened | Number Sequenced |
| --- | --- | --- |
| Astrocytoma | 2/3 | 2 |
| Bladder | 5/10 | 3 |
| Breast | 18/22 (82%) | 17 |
| Cecum | 2/7 | 2 |
| Colon | 13/25 (52%) | 12 |
| Duodenum | 0/1 | 0 |
| Glioma | 12/22 (55%) | 10 |
| Lung | 10/26 (38%) | 7 |
| Leukemia/Lymphoma | 9/28 (32%) | 8 |
| Melanoma | 7/24 (29%) | 4 |
| Neuroblastoma | 2/9 | 2 |
| Ovarian | 4/8 | 4 |
| Pancreatic | 12/13 (92%) | 11 |
| Prostate | 2/4 | 2 |
| Renal | 0/3 | 0 |
| Submaxillary | 0/1 | 0 |
| Testis | 3/5 | 3 |
| Thyroid | 1/2 | 1 |
| TOTAL | 102/213 (48%) | 88 |

The polymorphic markers used to examine LOH were D17S786, D17S952, D17S969 and D17S520. These markers had heterozygosity indices of 0.78, 0.69, 0.71 and 0.79, respectively. LOH was assessed from the combined apparent hemizygosities of these four short tandem repeat markers. The probability that a tumor cell line does not have LOH in this region and is homozygous for all four markers is approximately 0.0042. The percentage of LOH was only calculated for cancer types with a sample size greater than 10. The number of cell lines of each cancer type screened for candidate gene mutations by sequencing is shown. The two cell lines, ASPC-1 and NCI-H774, with homozygous deletions affecting MKK4 were not sequenced.

The inserts in the BACs were sequenced (greater than 95%) and numerous STSs were generated. These STSs were ordered within the BACs and used to delineate the boundaries of the deletion in ASPC-1. The STS mapping revealed that the homozygous deletion minimally extended from the T7 STS of BAC 86A8 to D17S969. Table 2 lists STSs which were deleted and their corresponding primers (the forward and reverse directionality of these primers are arbitrary). Also shown in Table 2 are five STSs which are not deleted in ASPC-1. The estimated size of the deletion in the ASPC-1 cell line is 150–250 kb.

EXAMPLE 2

Identification of Genes within the Genomic Region around D17S969

To identify genes that were located within the genomic region around D17S969, DNA from BACs 95I2 and 66I11 were used to hybrid select from a pool of cDNAs prepared from multiple normal tissues. Genomic sequences generated from BACs 95I2 and 66I11 were used to identify hybrid selected clones that represented multi-exon cDNAs, as well as to screen sequence databases for homologous genes. Three candidate genes spanned the deleted region of ASPC-1: CG1, which encodes a novel zinc-finger protein (unpublished data); CG2, which encodes MKK4 (Derijard et al., 1995; Lin et al., 1995) (Genbank L36870, U17743); and CG3, which codes for a protein homologous to sea urchin axonemal dynein heavy chain subunit (Genbank X59603, X99947). Using STSs developed from intron sequences of these candidate genes, it was determined that CG1 was completely deleted in ASPC-1, whereas only the 5' region of CG2 and 3' region of CG3 were absent in that cell line. Specifically, it was found that the three exons on the 5' end of the MKK4 gene, designated Exons A, B and C, were homozygously deleted in ASPC-1 (FIG. 2A). Comparison of the cDNA sequence of MKK4 with genomic sequences from BACs 95I2 and 66I11 revealed that the coding sequence of MKK4 was entirely within 66I11, and that the gene was comprised of at least 11 exons; exon A was located in a CpG island.

EXAMPLE 3

Sequencing of MKK4 Genomic DNA

The MKK4 genomic DNA was sequenced by sequencing the inserts in BACs 66I11 and 95I2. The sequence data was aligned with the Genbank sequences for MKK4 (JNKK) cDNA (Genbank accession numbers U17743 and L36870). In this manner it was established that MKK4 consists of 11 coding exons. The genomic sequence which extends beyond the combined sequence data from Genbank accession numbers U17743 and L36870 has not been classified as being intron

TABLE 2

| Primers | | | |
|---|---|---|---|
| Deleted STS | | | |
| (1) A1.1a | F = TTCTGTGGCATCCTGATTC | (SEQ ID NO:1) | |
|  | R = AAATGTAGCGGGGTAAAGC | (SEQ ID NO:2) | |
| (2) A1.1z | F = CCTTATTGCGAAAAAGTTC | (SEQ ID NO:3) | |
|  | R = GATACCTGGGCATTGAG | (SEQ ID NO:4) | |
| (3) 86a8.T7 | F = GATTATCCCAAACACAGCATCA | (SEQ ID NO:5) | |
|  | R = AATGTATCTTTCTCCACCCTTC | (SEQ ID NO:6) | |
| (4) A1.47 | F = TTGAGAAATTCCTCATGGCC | (SEQ ID NO:7) | |
|  | R = GGGATTCAGAGTAAACCTTGCT | (SEQ ID NO:8) | |
| (5) 95I2.S6 | F = CTGCTCAGTGCTGATGGGATT | (SEQ ID NO:9) | |
|  | R = CTTCGGTCCTCCTAAATGTCT | (SEQ ID NO:10) | |
| (6) 66I11.T7 | F = TTTAGTAGAGATGGGGTTTCAC | (SEQ ID NO:11) | |
|  | R = GACTATCAGACTCTTCCTCC | (SEQ ID NO:12) | |
| (7) 142e17.T7 | F = TTACTCATGTAATGTGGACCTG | (SEQ ID NO:13) | |
|  | R = GCAGAACATTTCTCGGGACTA | (SEQ ID NO:14) | |
| (8) D17S969 | F = ATCTAATCTGTCATTCATCTATCCA | (SEQ ID NO:15) | |
|  | R1 = AACTGCAGTGCTGCATCATA | (SEQ ID NO:16) | |
|  | R2 = AACTGCAGTGTTGCATCATA | (SEQ ID NO:17) | |
| STSs not deleted | | | |
| (1) 66I11.S6 | F = TTCGACAATAGGCATAGCTG | (SEQ ID NO:18) | |
|  | R = AGCTCATTCTTCAGAACTAAA | (SEQ ID NO:19) | |
| (2) 147g20.S6 | F = AAGCTTTCCAAACCTCATCA | (SEQ ID NO:20) | |
|  | R = CCAACTACAGGCTGAAGCA | (SEQ ID NO:21) | |

TABLE 2-continued

Primers

| | | | |
|---|---|---|---|
| (3) | 163g5.T7 | F = TTCCCATGGTTTTGTTATCA | (SEQ ID NO:22) |
| | | R = ACCAAATCCCGAAGATTAC | (SEQ ID NO:23) |
| (4) | 142e17.S6 | F = AGGTAAAAGCTGTATTCCAGAT | (SEQ ID NO:24) |
| | | R = TCCAAAAGTGTTTAGGATGAGT | (SEQ ID NO:25) |
| (5) | 95I2.T7 | F = GATCACAAAATACCATAAACAAAC | (SEQ ID NO:26) |
| | | R = TGATGTGGCTTCAAAGGAAATG | (SEQ ID NO:27) | or exon. The complete genomic sequence has not been determined. The regions around each of the exons has been determined and the known sequence is presented as 11 separate fragments (A–K) with each fragment including a single exon surrounded by intronic sequence. These 11 fragments are presented as SEQ ID NOs:36–46 in the Sequence Listing.

The 5'-end of the MKK4 gene has not been completely defined because it is GC rich. The two published reports (Dérijard et al., 1995; Lin et al., 1995) both propose the same open reading frame and initiation methionine. This proposed translation start site is at base number 21 of the Lin et al. (1995) sequence (Genbank accession number U17743) and base number 10 of the Dérijard et al. (1995) sequence (Genbank accession number L36870). It is therefore uncertain from the two published reports whether the proposed translation start site is the correct site. Efforts here have not yet further extended the 5'-end of the cDNA. The genomic sequence generated here includes the 5'-Genbank submissions. There is a polymorphism about 30 codons upstream of the proposed initiation ATG that creates an in-frame stop in more than half of the samples screened. If this sequence is part of the MKK4 cDNA then the proposed start codon is correct.

EXAMPLE 4

Loss of Heterozygosity (LOH) Studies

The initial observation of a homozygous deletion in one pancreatic cancer cell line suggested two possibilities: (i) inactivation of a gene by the ASPC-1 lesion caused tumor progression; or (ii) the homozygous deletion was a random event irrelevant to the transformed state of the cells. To distinguish between these possibilities, a set of human cancer cell lines was identified that exhibited LOH within this region. These cell lines were examined for mutations in the three candidate genes. If the ASPC-1 lesion were causal, one would expect to find mutations of the responsible gene in the remaining allele of some of the tumor cell lines with LOH.

LOH analysis was performed using fluorescently tagged STRs as previously described (Cory et al., 1994). By radiation hybrid mapping (Cox et al., 1990), it was determined that D17S786, D17S952, D17S520 and D17S969 were 74, 81, 89 and 94 cR, respectively, from the p-telomere of chromosome 17. Two of the cancer cell lines examined, breast BT-474 and thyroid SW579, were heterozygous for D17S786 and appeared to be hemizygous for D17S952, D17S969 and D17S520, suggesting that they had a LOH breakpoint between P53 and the MKK4 locus. To test this inference, four additional polymorphic STRs (D17S503, D17S945, D17S1159 and D17S947) were used to examine the two cell lines. Based on the radiation hybrid mapping, the markers were placed along 17p in the following order: telomere-p53-D17S503-D17S786-D17S952-D17S945-D17S520-D17S1159-D17S969-D17S947-centromere. Both BT-474 and SW579 appeared to be heterozygous from D17S503 to D17S945, and hemizygous from D17S520 to centromere, consistent with an LOH breakpoint occurring between the P53 and MKK4 loci.

Tumor cell lines were screened for loss of heterozygosity (LOH) within the deleted region seen in the ASPC-1 cell line. Four polymorphic markers (D17S786, D17S952, D17S969 and D17S520) were used to screen 213 different cell lines from various types of cancer for LOH (see Table 1). The primers for these markers are shown in Table 3. Of the 213 cell lines which were screened, 102 exhibited LOH. This overall LOH frequency of 48% is not unexpected given that P53 is located roughly 10 cM from D17S969.

TABLE 3

| Marker | Primers | | |
|---|---|---|---|
| S786 | D17S786.F = CTGTAACCTTGGGCATCTTC | (SEQ ID NO:28) |
| | D17S786.R = AGGATTTGGGCTCTTTTGTAA | (SEQ ID NO:29) |
| S952 | D17S952.F = TGCACACAGTTGGCATTCAG | (SEQ ID NO:30) |
| | D17S952.R = CCCAGGAGACAGCAGAAGA | (SEQ ID NO:31) |
| S969 | D17S969.F = ATCTAATCTGTCATTCATCTATCCA | (SEQ ID NO:32) |
| | D17S969.R = AACTGCAGTGCTGCATCATA | (SEQ ID NO:33) |
| S520 | D17S520.F = GGAGAAAGTGATACAAGGGA | (SEQ ID NO:34) |
| | D17S520.R = TAGTTAGATTAATACCCACC | (SEQ ID NO:35) |

Using PCR and DNA sequencing methodologies, 89 of the tumor cell lines that displayed LOH were screened for sequence variations in the exon and flanking splice-consensus regions of the candidate genes. Using genomic DNAs of cell lines as templates, nested PCR amplifications were performed to generate amplicons of the candidate genes that were screened for mutations. The primers listed in Table 4 were used to produce the amplicons of MKK4. Using the outer FA-RP primer pair, 1–10 ng of genomic DNA were subjected to a 25 cycle primary amplification, after which the PCR products were diluted 60-fold and reamplified using nested M13-tailed FB-RQ primers for another 22–25 cycles; either TaqPlus or AmpliTaq Gold was used in the reactions. DNA sequencing and mutation screening were performed as previously described (Teng et al., 1996) with the following modification: M13 forward or reverse fluorescent energy transfer (FET)

TABLE 4

Exon A

Primary Amplicon

| | | |
|---|---|---|
| CG2exA.FA = GCTGTCTGCTTCACAGGTCGC | | (SEQ ID NO:47) |
| CG2exA.RP = CGGGGAGGGAGAGAGGGAGA | | (SEQ ID NO:48) |

Secondary Amplicon

| | | |
|---|---|---|
| CG2exA.FB = GTTTTCCCAGTCACGACGCGGTTCTGCAGCTCAGCATCT | | (SEQ ID NO:49) |
| CG2exA.RQ = AGGAAACAGCTATGACCATCGGCTGCCGTGGCTTCCTCA | | (SEQ ID NO:50) |

Exon B

Primary Amplicon

| | | |
|---|---|---|
| CG2exB.FA = TTGAGAAATTCCTCATTGCC | | (SEQ ID NO:51) |
| CG2exB.RP = CAATATTCCCAGAGAGTTTA | | (SEQ ID NO:52) |

Secondary Amplicon

| | | |
|---|---|---|
| CG2exB.FB = GTTTTCCCAGTCACGACGTTGCCTTTTGGTGTGACTTT | | (SEQ ID NO:53) |
| CG2exB.RQ = AGGAAACAGCTATGACCATACTGACATCTCATAATTGGA | | (SEQ ID NO:54) |

Exon C

Primary Amplicon

| | | |
|---|---|---|
| CG2exC.FA = CCTGGAGGTCAGACTATTTT | | (SEQ ID NO:55) |
| CG2exC.RP = AAAGGAGTTGGAGAAACAAT | | (SEQ ID NO:56) |

Secondary Amplicon

| | | |
|---|---|---|
| CG2exC.FB = GTTTTCCCAGTCACGACGAACATTTTTCCCACACATTA | | (SEQ ID NO:57) |
| CG2exC.RQ = AGGAAACAGCTATGACCATAGGAACACAACAACAGTGGT | | (SEQ ID NO:58) |

Exon D

Primary Amplicon

| | | |
|---|---|---|
| CG2exD.FA = CTTGTGAAGTATAAGGAAAGATG | | (SEQ ID NO:59) |
| CG2exD.RP = TGGTTAAACACTAAGATACTGAG | | (SEQ ID NO:60) |

Secondary Amplicon

| | | |
|---|---|---|
| CG2exD.FB = GTTTTCCCAGTCACGACGTCGTAACGGTTTTTCTCTACCA | | (SEQ ID NO:61) |
| CG2exD.RQ = AGGAAACAGCTATGACCATAAGAATAGAATCGAATCCTGCC | | (SEQ ID NO:62) |

Exon E

Primary Amplicon

| | | |
|---|---|---|
| CG2exE.FA = TGGGGAAAATTGGCTTTAACTAC | | (SEQ ID NO:63) |
| CG2exE.RP = CGAGACCATTATGACCTATTGTG | | (SEQ ID NO:64) |

Secondary Amplicon

| | | |
|---|---|---|
| CG2exE.FB = GTTTTCCCAGTCACGACGCTAGTTTGACATTTGAAATAAGCA | | (SEQ ID NO:65) |
| CG2exE.RQ = AGGAAACAGCTATGACCATCAGAAGTGACTTTGTCTCTGGT | | (SEQ ID NO:66) |

Exon F

Primary Amplicon

| | | |
|---|---|---|
| CG2exF.FA = GCTTAAAATGTATGCAGAGG | | (SEQ ID NO:67) |
| CG2exF.RP = CCAGAGAGAAAAATAGCAGT | | (SEQ ID NO:68) |

TABLE 4-continued

```
Secondary Amplicon

CG2exF.FB = GTTTTCCCAGTCACGACGCTTGTGATAAACTGTTGTGC      (SEQ ID NO:69)
CG2exF.RQ = AGGAAACAGCTATGACCATCACTGTAATTTTCAATAACC      (SEQ ID NO:70)

Exon G

Primary Amplicon

CG2exG.FA = TCTGAATTTAAGGACTTGAC                         (SEQ ID NO:71)
CG2exG.RP = AGCAAAGTTTCATGGAGAGG                         (SEQ ID NO:72)

Secondary Amplicon

CG2exG.FB = GTTTTCCCAGTCACGACGCTTAAAGTGAAGCCTTATGT       (SEQ ID NO:73)
CG2exG.RQ = AGGAAACAGCTATGACCATGGTAAAACCGTATGACTAATG     (SEQ ID NO:74)

Exon H

Primary Amplicon

CG2exH.FA = AGGAATATACTGGCATTTTGG                        (SEQ ID NO:75)
CG2exH.RP = AGCAACTTAAAACCATAGTG                         (SEQ ID NO:.76)

Secondary Amplicon

CG2exH.FB = GTTTTCCCAGTCACGACGGTTGCTTCCATTTGCCTATT       (SEQ ID NO:77)
CG2exH.RQ = AGGAAACAGCTATGACCATCGAACGGGGAAGTCTGATTA      (SEQ ID NO:78)

Exon I

Primary Amplicon

CG2exI.FA = ACTTAGCCTTTATGATTCTG                         (SEQ ID NO:79)
CG2exI.RP = GCTTGAAAAGTAGGGTGATG                         (SEQ ID NO:80)

Secondary Amplicon

CG2exI.FB = GTTTTCCCAGTCACGACGTTTTGCTTGTAGTTTAGATTT      (SEQ ID NO:81)
CG2exI.RQ = AGGAAACAGCTATGACCATTCCTCCATGTAAAGTACCAA      (SEQ ID NO:82)

Exon J

Primary Amplicon

CG2exJ.FA = GGCTGTCTGCGTTGTTACTT                         (SEQ ID NO:83)
CG2exJ.RP = TAACAAAAACACTCAATAAA                         (SEQ ID NO:84)

Secondary Amplicon

CG2exJ.FB = GTTTTCCCAGTCACGACGTGTGAAAAGAAAAATACTTAGG     (SEQ ID NO:85)
CG2exJ.RQ = AGGAAACAGCTATGACCATGTTTGTTTATGACAGAGAGG      (SEQ ID NO:86)

Exon K

Primary amplicon

CG2exK.FA = TGGGAGCCTGGAGTTCTATG                         (SEQ ID NO:87)
CG2exK.RP = GGGAAGGGAAAGAGATTCGG                         (SEQ ID NO:88)

Secondary Amplicon

CG2exK.FB = GTTTTCCCAGTCACGACGTTGGAAAATGTTCAGTTTGG       (SEQ ID NO:89)
CG2exK.RQ = AGGAAACAGCTATGACCATCGTTCTAGGTGACAGGAGTA      (SEQ ID NO:90)
```

Eleven exons, shown as Exons A–K, were defined for this gene. Exon A contains the 5'-end of the MKK4 cDNAs reported by Derijard et al. (1995) and Lin et al. (1995). Amplicon K covers the 5' splice-junction, coding sequence and translational stop codon of the last exon of the gene. dye-labeled primers were used in the sequencing reactions. Greater than 90% coverage of the coding sequence of MKK4 was obtained for every tumor cell line screened. All detected mutations were confirmed by sequencing a newly amplified product. The data which was generated was screened for sequence variants using an in-house Unix program or Sequencher. Such screening may be analyzed by other computer programs and screening methods as well as methods of analysis are well-known within the art. The primers used for amplifying the mutation screening amplicons are shown in Table 4. For each of the 89 tumor cell lines, greater than 95% of the coding region for MKK4 was screened.

In the course of mutation screening, a second homozygous deletion event in a lung carcinoma cell line, NCI-H774, was detected. In these lung cells, exons 3–11 of MKK4 were deleted; therefore one breakpoint of the homozygous deletion was located between exons 2 and 3 of this gene (data not shown). By comparing the wild-type sequences of candidate genes to the corresponding DNA sequences of tumor cell lines, two nonsense and three missense variants of MKK4 were detected in the cell lines examined (Table 5). No sequence variants were observed in the other candidate genes. The nonsense mutations found in the CAPAN-1 pancreatic carcinoma cell line and MDA-MB-415 breast carcinoma cell line were located at codon positions 221 and 280 of MKK4, respectively (mutations at positions 681 and 859 of the cDNA (SEQ ID NO:91)). These lesions result in the expression of truncated polypeptide products that lack 179 and 120 amino acid residues from their respective carboxy-termini. The nonsense mutations of CAPAN-1 eliminates subdomains VI–XI of MKK4 which are essential for catalytic activity (Hanks et al., 1988), whereas the truncated MKK4 product of MDA-MB-415 lacks subdomains IX–XI which contain three residues at positions that are almost invariant in both SER/THR and TYR protein kinases (Hanks et al., 1988). The three missense sequence variants of MKK4 were observed in cancer cell lines derived from breast (MDA-MB-134-VI; S184L), colon (SW 1417; R274G) and testis (NCCIT; K309N); none of these three missense changes results in a conservative substitution (Table 5). The S184L and R274G alterations occurred at residues that are strictly conserved among the six known members of the MAP kinase kinase family.

to confirm presence of the desired alteration in MKK4 and absence of any other sequence artifacts.

Using the calcium phosphate precipitation method, $5 \times 10^6$ human kidney 293 cells were cotransfected with 3 μg of pcDNA3-Flag-MEKK1Δ (Yan et al., 1994; Minden et al., 1994) and 15 μg of pcDNA-HA-MKK4 construct or pcDNA3 vector (Invitrogen), and then cultured in a 10 cm² plate. After 8 hours, the media was removed and replaced with fresh DMEM containing 10% FCS. After an additional 24 hours, the media was removed, the cells were resuspended in ice-cold phosphate-buffered saline (PBS), pooled and centrifuged at 1000×g for 5 minutes at 4° C. The pelleted cells were lysed in 1.5 ml of ice cold Buffer I (50 mM TrisHCl, pH 7.4, 150 mM NaCl, 10% glycerol, 1% Triton X-100, 5 mM EDTA, 1 mM DTT, 50 mM β-glycerophosphate, 1 mM EGTA, and Complete™ protease inhibitors (Boehringer-Mannheim)) per six 10 cm² plates, and then centrifuged at 15,000×g for 10 minutes. The supernatant was transferred to a new tube and the pellet resuspended in 1.5 ml of Buffer I. A 15 μL aliquot of each fraction was mixed with 15 μL of Laemmli SDS sample buffer, run on a 15% polyacrylamide gel, and transferred onto Immobilon-P membrane (Millipore). These filters were blocked in PBS-MT (PBS containing 3% skim milk powder and 0.1% Tween 20) for 1 hour incubated with a 1:2000 dilution of anti-HA antibodies (Boehringer-Mannheim) in PBS-MT for 1 hour, washed, followed by immersion in a

TABLE 5

Sequence Variants Found in MKK4 in Human Tumor Cell Lines

| Cell Line | Type | Alteration | Exon | Codon | Predicted Effect |
|---|---|---|---|---|---|
| ASPC-1 | pancreas | homozygous deletion | A-C | — | no expression |
| NCI-H774 | lung | homozygous deletion | C-K | — | protein truncation |
| MDA-MB-134-VI | breast | TCG → TTG at nuc 551 (285 of SEQ ID NO:40) | E (base 38) | 184 | Ser → Leu |
| CAPAN-1 | pancreas | GAA → TAA at nuc 661 (421 of SEQ ID NO:41) | F (base 28) | 221 | Glu → Stop (protein truncation) |
| SW 1417 | colon | AGA → GGA at nuc 820 (117 of SEQ ID NO:43) | H (base 7) | 274 | Arg → Gly |
| MDA-MB-415 | breast | TCA → TAA at nuc 839 (136 of SEQ ID NO:43) | H (base 26) | 280 | Ser → Stop (protein truncation) |
| NCCIT | testis | AAG → AAC at nuc 927 (1066 of SEQ ID NO:44) | I (base 36) | 309 | Lys → Asn |

EXAMPLE 5

Biochemical Activity of MKK4 Variants

The five variants of MKK4 were generated by a PCR based mutagenesis strategy using reverse transcribed cDNA from normal pancreatic tissue as template. The hemagglutinin (HA) epitope was designed into the following PCR primer (HA-MKK4.F1), with HindIII and SacII sites at the 5' end, such that the tag would be fused in-frame to the N-terminus of the MKK4 polypeptide: 5'-AAGCTTCCGCGGGCCACCATGTATCCATACGAT-GTTCCAGATTACGCA GCGGCTCCGAGCCCGA-3' (SEQ ID NO:95). The downstream primer (MKK4.R50) used in combination with HA-MKK4.F1 to amplify the entire coding region of MKK4, along with an XbaI site present in cDNA sequence 3' of the translational stop codon, was 5'-TTCTTTACGTCTTGCTTCCTCTC-3' (SEQ ID NO:96). The amplified mutated coding fragment of MKK4 was digested with HindIII and XbaI, cloned into pcDNA3 (Invitrogen) and transformed into DH5α cells. These plasmid constructs in these cells were isolated using the Maxi-DNA preparation protocols from Qiagen and then sequenced 1:20,000 dilution of peroxidase labeled goat anti-mouse IgG antibodies (Amersham) in PBS-MT for 1 hour. After extensive washing, the blots were developed using enhanced chemiluminescence (ECL kit, Amersham). Western blots for detecting Flag-tagged MEKK1Δ were done in a similar fashion except that a 1:1000 dilution of anti-Flag antibodies (Kodak) was used instead.

For the kinase assays, soluble cell extracts were normalized to within a 3-fold range for MKK4 content prior to immunoprecipitation. One mL of normalized lysate was incubated with 5 μL of anti-HA ascites and 20 μL of protein A/G Sepharose for 2 hours at 4° C. Beads were subsequently washed once in Buffer I, once in Buffer I with 0.5 M NaCl, twice in Buffer I with 1 M NaCl, and finally twice in Buffer II (25 mM TrisHCl, pH 7.4, 0.1 mM EDTA, 10 mM MgCl₂, 1 mM DTT). Twenty μg of kinase dead SAPK-β K55R was then added to each aliquot of beads and the final volume was made to 100 μL with Buffer II containing 100 μM ATP (~2000 cpm ³²P per pmole ATP). Tubes were incubated at 30° C. for 30 minutes and stopped with 100 μL of Laemmli SDS sample buffer. Thirty μL of each reaction was fractionated on a 15% SDS-polyacrylamide gel, transferred onto Immobilon-P membrane, and autoradiographed. The SAPK bands were subsequently excised and $^{32}P$ incorporation was quantified by scintillation counting.

To ascertain if the five MKK4 variants identified were biochemically active, the variants were expressed in cultured mammalian cells and then kinase assays were performed in vitro on the altered proteins. Human kidney 293 cells were transfected with Flag-tagged MEKK1Δ, a truncated form of MEKK1 that constitutively activates wild-type (WT) MKK4 (Hirai et al., 1996), in combination with hemagglutinin (HA)-tagged wild-type or mutant MKK4; both constructs were placed under the control of the CMV promoter in pcDNA3 expression vector. Fractionation of transfected cell lysates revealed that while S184L-MKK4, R274G-MKK4 and K309N-MKK4 behaved similarly to WT-MKK4, the soluble quantities of the two variants (NON221-MKK4 and NON280-MKK4), truncated as a result of the nonsense mutations, were severely reduced (FIGS. 3A–3E).

Using anti-HA antibodies, the soluble epitope-tagged proteins were immunoprecipitated and then examined for MKK4 activity by assaying the phosphorylation of SAPK-β K55R, a catalytically inactive form of SAPK (Sanchez et al., 1994). In these assays, whereas the activity of K309N-MKK4 was comparable to that of WT-MKK4, each of the other four variant MKK4 proteins exhibited less than 5% of wild-type activity (FIGS. 3A–3E). The relative activities of these MKK4 variants correlate well with the degree of conservation of the residues at these altered sites. As predicted, the truncated NON221-MKK4 and NON280-MKK4 proteins were catalytically inactive. The S184L-MKK4 and R274G-MKK4 variants, which failed to exhibit kinase activity in these assays, had point mutations at residues strictly conserved among the six known members of the MAPKK family (Derijard et al., 1995; Lin et al., 1995; Zheng and Guan, 1993; English et al., 1995; Moriguchi et al., 1996). In contrast, the K309N-MKK4 variant, which appears to have wild-type activity, has a missense alteration at a site that is divergent among the MAPKKs. The absence of a substantial effect caused by the K309N change in these assays, however, does not preclude a functional defect in vivo that is masked by coexpression with MEKK1Δ, or is not reflected by in vitro phosphorylation of SAPK-β K55R.

EXAMPLE 6

MKK4 Mutations in Primary and Metastatic Tumors

Given the discovery of MKK4 mutations in cancer cell lines, it is important to determine if MKK4 lesions occur in primary or metastatic tumors. Forty-five human primary breast tumor specimens, prescreened for LOH, were examined for coding alterations in MKK4. No sequence variants were detected in these tumor DNAs. Previous studies on P16 (Spruck et al., 1994) and MMAC1(Steck et al., 1997) have shown that a significantly higher incidence (35%–40%) of mutation have been observed in tumor cell lines compared to primary tumors. Since MKK4 is mutated at ~7% frequency in our set of cell lines, it was not expected that MKK4 lesions would be observed in our set of 45 primary breast tumor specimens. Moreover, homozygous deletion is a mechanism used to inactivate this gene; it is highly improbable that such deletion events would have been detected in primary tumors by our screen because these specimens are heterogeneous and invariably contaminated with normal cells. Overall, the observation of a low incidence of MKK4 mutation in cancer cell lines suggests at least one of the following possibilities: (i) MKK4 can function as a tumor or metastatic suppressor in certain cell types but is not commonly targeted for mutation during cellular transformation in vivo; (ii) the signaling pathway that MKK4 is involved in may be inactivated by mutagenesis of one of its other components (e.g., MEKK1); or (iii) the MKK4 mutations in these lines were generated while these cells were cultured in vitro.

Accumulated evidence implicates the MAPK pathway involving MEKK1, MKK4 and SAPK, in signaling apoptosis induced by inflammatory cytokines and environmental stresses in a variety of mammalian cell types (Xia et al., 1995; Chen et al., 1996; Johnson et al., 1996; Verheij et al., 1996; Cuvillier et al., 1996). This apoptotic signaling pathway appears to be mediated by the second messenger ceramide and attenuated by sphingosine-1-phosphate (Verheij et al., 1996; Cuvillier et al., 1996); however, the identity of the upstream regulator(s) of MEKK1 has not been elucidated. Johnson and colleagues demonstrate that although MEKK1 activation facilitates programmed cell death in Swiss 3T3 cells, stimulation of SAPK is apparently not required for the process (Johnson et al., 1996). Work by Liu et al. also supports the notion that SAPK activation is not required for inducing apoptosis in MCF-7 cells, leading them to propose that MEKK-MKK4-SAPK is not involved in programmed cell death (Liu et al., 1996). The complexity of mammalian MAPK signal transduction cascades is further reflected by the recent discovery of ASK-1, a human MAPKKK that induces apoptosis when overexpressed in Mv1Lu cells and phosphorylates MKK4, MKK3 and MKK6 in vitro (Ichijo et al., 1997). Thus, definition of the pathways by which mitogen-activated protein kinases signal apoptosis remains unclear.

Out of 90 cancer cell lines with LOH in the MKK4 region, six lines derived from pancreatic, breast, lung and colon carcinomas, do not express functional MKK4 protein; the NCCIT testis line had a missense change that did not perturb kinase activity in the in vitro assays. Of interest, mutations in P53 have been reported in the two pancreatic carcinoma cell lines, ASPC-1 and CAPAN-1 (Ruggeri et al., 1992; Redston et al., 1994) which have deleterious MKK4 lesions. In addition, CAPAN-1* was previously determined to carry the 6174delT mutation in BRCA2 (Teng et al., 1996). These correlations suggest that inactivation of independent pathways defined by these tumor suppressor genes contributed to the transformation process of these pancreatic cells. The frequency of MKK4 mutations in cancer cell lines is low (6/90 tumor cell lines with LOH, about 7%), due in part to the high incidence of LOH caused by proximity of the P53 locus. However, the lack of detection of additional sequence variants by our screen for cancer cell line mutations in genes within this 17p region, as well as of BRCA2 previously (Teng et al., 1996), suggests that intragenic alterations that cause clonal selection are extremely rare. These findings suggest that the MKK4 lesions conferred a growth advantage in these cells that resulted in selection; this is consistent with the notion that inactivation of MKK4 can contribute to cellular transformation by preventing apoptotic signaling mediated by this MAPKK. Alternatively, it is possible that mutagenesis of MKK4 promotes tumor progression by a yet undefined mechanism.

The tumorigenic state of a cell is affected by mechanisms that control proliferation and apoptosis. Several well characterized cancer genes regulate programmed cell death, including BCL2, P53 and C-MYC (Cory et al., 1994; White et al., 1994; Chiarugi and Ruggiero, 1996). Studies on these genes reveal that inactivation of biochemical pathways that normally stimulated apoptosis can result in an increase in the tumorigenic potential of a cell. Current evidence linking MKK4 to programmed cell death signaling is based on correlations of kinase activation with the apoptotic induction of mammalian cells cultured in vitro (Xia et al., 1995; Chen et al., 1996; Johnson et al., 1996; Verheij et al., 1996; Cuvillier et al., 1996; Ichijo et al., 1997). Mouse knockout experiments have recently demonstrated that MKK4 plays an essential role in vivo, as homozygous knockout mice die prior to day 14 of embryonic development (Yang et al., 1997). The cancer cell lines characterized here should be useful for investigating the specific role(s) of MKK4 in cellular growth and differentiation, stress response, apoptosis and tumorigenesis. Confirmation of MKK4 involvement in signaling cellular growth or apoptosis would be another step taken toward defining the pathways that transduce and integrate signals that culminate in the decision by a cell to proliferate or suicide. Definition of these regulatory pathways should lead to the identification of significant targets for antitumor therapeutic development.

EXAMPLE 7

Two Step Assay to Detect the Presence of MKK4 in a Sample

Patient sample is processed according to the method disclosed by Antonarakis et al. (1985), separated through a 1% agarose gel and transferred to nylon membrane for Southern blot analysis. Membranes are UV cross linked at 150 mJ using a GS Gene Linker (Bio-Rad). An MKK4 probe is subcloned into pTZ18U. The phagemids are transformed into *E. coli* MV1190 infected with M13KO7 helper phage (Bio-Rad, Richmond, Calif.). Single stranded DNA is isolated according to standard procedures (see Sambrook et al., 1989).

Blots are prehybridized for 15–30 min at 65° C. in 7% sodium dodecyl sulfate (SDS) in 0.5 M $NaPO_4$. The methods follow those described by Nguyen, et al., 1992. The blots are hybridized overnight at 65° C. in 7% SDS, 0.5 M $NaPO_4$ with 25–50 ng/ml single stranded probe DNA. Post-hybridization washes consist of two 30 min washes in 5% SDS, 40 mM $NaPO_4$ at 65° C., followed by two 30-min washes in 1% SDS, 40 mM $NaPO_4$ at 65° C.

Next the blots are rinsed with phosphate buffered saline (pH 6.8) for 5 min at room temperature and incubated with 0.2% casein in PBS for 30–60 min. at room temperature and rinsed in PBS for 5 min. The blots are then preincubated for 5–10 minutes in a shaking water bath at 45° C. with hybridization buffer consisting of 6 M urea, 0.3 M NaCl, and 5X Denhardt's solution (see Sambrook, et al., 1989). The buffer is removed and replaced with 50–75 $\mu l/cm^2$ fresh hybridization buffer plus 2.5 nM of the covalently cross-linked oligonucleotide-alkaline phosphatase conjugate with the nucleotide sequence complementary to the universal primer site (UP-AP, Bio-Rad). The blots are hybridized for 20–30 min at 45° C. and post hybridization washes are incubated at 45° C. as two 10 min washes in 6 M urea, 1× standard saline citrate (SSC), 0.1% SDS and one 10 min wash in 1× SSC, 0.1% Triton® X-100. The blots are rinsed for 10 min at room temp. with 1× SSC.

Blots are incubated for 10 min at room temperature with shaking in the substrate buffer consisting of 0.1 M diethanolamine, 1 mM $MgCl_2$, 0.02% sodium azide, pH 10.0. Individual blots are placed in heat sealable bags with substrate buffer and 0.2 mM AMPPD (3-(2'-spiroadamantane)-4-methoxy-4-(3'-phosphoryloxy)phenyl-1,2-dioxetane, disodium salt, Bio-Rad). After a 20 min incubation at room temperature with shaking, the excess AMPPD solution is removed. The blot is exposed to X-ray film overnight. Positive bands indicate the presence of MKK4.

EXAMPLE 8

Generation of Polyclonal Antibody against MKK4

Segments of MKK4 coding sequence are expressed as fusion protein in *E. coli*. The overexpressed protein is purified by gel elution and used to immunize rabbits and mice using a procedure similar to the one described by Harlow and Lane, 1988. This procedure has been shown to generate Abs against various other proteins (for example, see Kraemer, et al., 1993).

Briefly, a stretch of MKK4 coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. The identification of the protein as the MKK4 fusion product is verified by protein sequencing at the N-terminus. Next, the purified protein is used as immunogen in rabbits. Rabbits are immunized with 100 $\mu g$ of the protein in complete Freund's adjuvant and boosted twice in 3 week intervals, first with 100 $\mu g$ of immunogen in incomplete Freund's adjuvant followed by 100 $\mu g$ of immunogen in PBS. Antibody containing serum is collected two weeks thereafter.

This procedure is repeated to generate antibodies against the mutant forms of the MKK4 gene. These antibodies, in conjunction with antibodies to wild type MKK4, are used to detect the presence and the relative level of the mutant forms in various tissues and biological fluids.

EXAMPLE 9

Generation of Monoclonal Antibodies Specific for MKK4

Monoclonal antibodies are generated according to the following protocol. Mice are immunized with immunogen comprising intact MKK4 or MKK4 peptides (wild type or mutant) conjugated to keyhole limpet hemocyanin using glutaraldehyde or EDC as is well known.

The immunogen is mixed with an adjuvant. Each mouse receives four injections of 10 to 100 $\mu g$ of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of MKK4 specific antibodies by ELISA or RIA using wild type or mutant MKK4 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

EXAMPLE 10

Sandwich Assay for MKK4

Monoclonal antibody is attached to a solid surface such as a plate, tube, bead, or particle. Preferably, the antibody is attached to the well surface of a 96-well ELISA plate. 100 μl sample (e.g., serum, urine, tissue cytosol) containing the MKK4 peptide/protein (wild-type or mutants) is added to the solid phase antibody. The sample is incubated for 2 hrs at room temperature. Next the sample fluid is decanted, and the solid phase is washed with buffer to remove unbound material. 100 μl of a second monoclonal antibody (to a different determinant on the MKK4 peptide/protein) is added to the solid phase. This antibody is labeled with a detector molecule (e.g., 125-I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of MKK4 peptide/protein present in the sample, is quantified. Separate assays are performed using monoclonal antibodies which are specific for the wild-type MKK4 as well as monoclonal antibodies specific for each of the mutations identified in MKK4.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

American Cancer Society (1992). In *Cancer Facts and Figures*—1992.
Anand, R. (1992). *Techniques for the Analysis of Complex Genomes*, (Academic Press).
Anderson, et al. (1980). *Proc. Natl. Acad. Sci. USA* 77:5399–5403.
Anderson, J. A., et al. (1992). *J. Otolaryngology* 21:321.
Antonarakis, S. E., et al. (1985). *New Engl. J. Med.* 313:842–848.
Ausubel, F. M., et al. (1992). *Current Protocols in Molecular Biology*, (John Wiley and Sons, New York, N.Y.).
Beaucage and Carruthers (1981). *Tetra. Letts.* 22:1859–1862.
Berkner (1992). *Curr. Top. Microbiol. Immunol.* 158:39–61.
Berkner, et al. (1988). *BioTechniques* 6:616–629.
Borman, S. (1996). *Chemical & Engineering News*, December 9 issue, pp. 42–43.
Brandyopadhyay and Temin (1984), *Mol. Cell. Biol.* 4:749–754.
Breakfield and Geller (1987). *Mol. Neurobiol* 1:337–371.
Brinster, et al. (1981). *Cell* 27:223–231.
Buchschacher and Panganiban (1992). *J. Virol.* 66:2731–2739.
Cannon-Albright, L. A., et al. (1992). *Science* 258:1148–1152.
Capecchi, M. R. (1989). *Science* 244:1288.
Cariello (1988). *Human Genetics* 42:726.
Chee, M., et al. (1996). *Science* 274:610–614.
Chen, Y.-R. et al. (1996). *J. Biol. Chem.* 271:631–634.
Cheng, J. Q., et al. (1993). *Cancer Res.* 53:4761.
Chiarugi, V. and Ruggiero, M. (1996). *Tumori* 82:205–209.
Conner, B. J., et al. (1983). *Proc. Nat. Acad. Sci. USA* 80:278–282.
Constantini and Lacy (1981). *Nature* 294:92–94.
Cory, S. et al. (1994). In *The Molecular Genetics of Cancer*, Cold Spring Harbor Symposia on Quantitative Biology, Vol. LIX, 365–375 (Cold Spring Harbor Laboratory Press, New York).
Cotten, et al. (1990). *Proc. Natl. Acad. Sci. USA* 87:4033–4037.
Cotton, et al. (1988). *Proc. Nat. Acad. Sci. USA* 85:4397.
Couch, F. J. et al. (1996). *Genomics* 36:86–99.
Cox, D. R. et al. (1990). *Science* 250:245–250.
Culver, et al. (1992). *Science* 256:1550–1552.
Curiel, et al. (1991a). *Proc. Natl. Acad Sci. USA* 88:8850–8854.
Curiel, et al. (1991b). *Hum. Gene Ther.* 3:147–154.
Cuvillier, O. et al. (1996). *Nature* 381:800–803.
Dérijard, B., et al. (1995). *Science* 267:682–685.
Deutscher, M. (1990). *Meth. Enzymology* 182:83–89 (Academic Press, San Diego).
DeRisi, J., et al. (1996). *Nature Genetics* 14:457–460.
Diaz, M. O., et al. (1988). *Proc. Natl. Acad. Sci. USA* 85: 5259–5263.
Donehower, L. A., et al. (1992). *Nature* 356:215.
Editorial (1996). *Nature Genetics* 14:367–370.
English, J. M. et al. (1995). *J. Biol. Chem.* 270:28897–28902.
*Enhancers and Eukaryotic Gene Expression*, Cold Spring Harbor Press, Cold Spring Harbor, N.Y. (1983).
Erickson, J. et al. (1990). *Science* 249:527–533.
Ewen, M. E., et al. (1993). *Cell* 73:47.
Felgner, et al. (1987). *Proc. Natl. Acad. Sci. USA* 84:7413–7417.
Fiers, et al. (1978). *Nature* 273:113.
Fink, et al. (1992). *Hum. Gene Ther.* 3:11–19.
Finkelstein, J., et al. (1990). *Genomics* 7:167–172.
Fountain, J. W., et al. (1992). *Proc. Natl. Acad. Sci. USA* 89:10557–10561.
Freese, et al. (1990). *Biochem. Pharmacol.* 40:2189–2199.
Friedman, T. (1991). In *Therapy for Genetic Diseases*, T. Friedman, ed., Oxford University Press, pp. 105–121.
Glover, D. (1985). *DNA Cloning*, I and II (Oxford Press).
Goding (1986). *Monoclonal Antibodies: Principles and Practice*, 2d ed. (Academic Press, New York).
Godowski, et al. (1988). *Science* 241:812–816.
Goldstein, A. M., et al. (1994). *Am. J. Hum. Genet.* 54:489.
Gordon, et al. (1980). *Proc. Natl. Acad. Sci. USA* 77:7380–7384.
Gorziglia and Kapikian (1992). *J. Virol.* 66:4407–4412.
Graham and van der Eb (1973). *Virology* 52:456–467.
Green, E. D. and Olson, M. V. (1990). *Science* 250:94–98.
Gruis, N. A., et al. (1993). *Melanoma Res.* 3:271.
Gruis, N. A., et al. (1995). *Am. J. Pathol.* 146:1–8.
Guthrie, G. and Fink, G. R. (1991). *Guide to Yeast Genetics and Molecular Biology*, (Academic Press).
Hacia, J. G., et al. (1996). *Nature Genetics* 14:441–447.
Hahn, S. A. et al. (1996). *Science* 271:350–353.
Hanks, S. K. et al. (1988). *Science* 241:42–52.
Hannon, G. J. and Beach, D. (1994). *Nature* 371:257–261.
Harlow and Lane (1988). *Antibodies: A Laboratory Manual*, (Cold Spring Harbor Laboratory, Cold Spring Harbor, N.Y.).
Hasty, P., K., et al. (1991). *Nature* 350:243.
Helseth, et al. (1990). *J. Virol.* 64:2416–2420.
Hirai, S. et al. (1996). *Oncogene* 12:641–650.

Hodgson, J. (1991). *Bio/Technology* 9:19–21.
Huse, et al. (1989). *Science* 246:1275–1281.
Ichijo, H. et al. (1997). *Science* 275:90–94.
Innis et al. (1990). *PCR Protocols: A Guide to Methods and Applications*, (Academic Press, San Diego).
Jablonski, E., et al. (1986). *Nucl. Acids Res.* 14:6115–6128.
Jakoby, W. B. and Pastan, I. H. (eds.) (1979). Cell Culture. Methods in Enzymology, volume 58 (Academic Press, Inc., Harcourt Brace Jovanovich (New York)).
James, C. D., et al. (1993). *Cancer Res.* 53:3674.
Jiang, P., et al. (1995). *J. Mol. Evol.* 41:795–802.
Johnson, et al. (1992). *J. Virol.* 66:2952–2965.
Johnson, N. L. et al. (1996). *J. Biol. Chem.* 271:3229–3237.
Kamb, A. et al. (1994). *Science* 264:436–440.
Kaneda, et al. (1989). *J. Biol. Chem.* 264:12126–12129.
Kanehisa (1984). *Nuc. Acids Res.* 12:203–213.
Kinszler, K. W., et al. (1991). *Science* 251:1366–1370.
Knudson, A. G. (1971). *Proc. Natl. Acad. Sci. USA* 68:820.
Knudson, A. G. (1993). *Nature Genet.* 5:103.
Kohler, G. and Milstein, C. (1975). *Nature* 256:495–497.
Kraemer, F. B., et al. (1993). *J. Lipid Res.* 34:663–672.
Kubo, T., et al. (1988). *FEBS Lett.* 241:119.
Kyriakis, J. M. and Avruch, J. (1996). *J. Biol. Chem.* 271:24313–24316.
Lammie, G. A., et al. (1991). *Oncogene,* 6:439.
Landegren, et al. (1988). *Science* 242:229.
Li, J. et al. (1997). *Science* 275:1943–1947.
Lim, et al. (1992). *Circulation* 83:2007–2011.
Lin, A., et al. (1995). *Science* 268:286–290.
Lipshutz, R. J., et al. (1995). *Biotechniques* 19:442–447.
Liu, Q., et al. (1995a). *Oncogene* 10:619–622.
Liu, Q., et al. (1995b). *Oncogene* 10:1061–1067.
Liu, Z.-G. et al. (1996). *Cell* 87:565–576.
Lockhart, D. J., et al. (1996). *Nature Biotechnology* 14:1675–1680.
Lukeis, R., et al. (1990). *Genes, Chromo. Cancer* 2:116–124.
Madzak, et al. (1992). *J. Gen. Virol.* 73:1533–1536.
Maniatis. T., et al. (1982). *Molecular cloning: A laboratory manual* (Cold Spring Harbor Laboratory, Cold Spring Harbor, N.Y.).
Mann and Baltimore (1985). *J. Virol.* 54:401–407.
Margolskee (1992). *Curr. Top. Microbiol. Immunol.* 158:67–90.
Martin, R., et al. (1990). *BioTechniques* 9:762–768.
Marx, J. (1994). *Science* 263:319–321.
Matteucci, et al. (1981). *J. Am. Chem. Soc.* 103:3185.
Matthews and Kricka (1988). *Anal. Biochem.* 169:1.
Merrifield (1963). *J. Am. Chem. Soc.* 85:2149–2156.
Metzger, et al. (1988). *Nature* 334:31–36.
Middleton, P. G., et al. (1991). *Leukemia* 5:680–682.
Miller (1992). *Curr. Top. Microbiol. Immunol.* 158:1–24.
Miller, et al. (1985). *Mol. Cell. Biol.* 5:431–437.
Miller, et al. (1988). *J. Virol.* 62:4337–4345.
Minden, A. et al. (1994). *Science* 266:1719–1723.
Mittlin (1989). *Clinical Chem.* 35:1819.
Modrich, P. (1991). *Ann. Rev. Genet.* 25:229–253.
Mombaerts, P., et al. (1992). *Cell* 68:869.
Moriguchi, T. et al. (1996). *J. Biol. Chem.* 271:13675–13679.
Moss (1992). *Curr. Top. Microbiol. Immunol.* 158:25–38.
Motokura, T., et al. (1991). *Nature* 350:512.
Muzyczka (1992). *Curr. Top. Microbiol. Immunol.* 158:97–123.
Nabel, et al. (1990). *Science* 249:1285–1288.
Nabel (1992). *Hum. Gene Ther.* 3:399–410.
Nancarrow, D. J., et al. (1993). *Am. J. Hum. Genet.* 53:936.
Nasmyth, K. and Hunt, T. (1993). *Nature* 366:634–635.
Newton, C. R., et al. (1989). *Nucl. Acids Res.* 17:2503–2516.
Nguyen, Q., et al. (1992). *BioTechniques* 13:116–123.
Novack, et al. (1986). *Proc. Nat. Acad. Sci. USA* 83:586.
Ohi, et al. (1990). *Gene* 89:279–282.
Olopade, O. I., et al. (1992). *Cancer Res.* 52:2523–2529.
Olopade, O. I., et al. (1993). *Cancer Res.* 53:2410–2415.
Orita, et al. (1989). *Proc. Nat. Acad. Sci. USA* 86:2776–2770.
Page, et al. (1990). *J. Virol.* 64:5370–5276.
Pellicer, et al. (1980). *Science* 209:1414–1422.
Petropoulos, et al. (1992). *J. Virol.* 66:3391–3397.
Philpott, K. L., et al. (1992). *Science* 256:1448.
Quantin, et al. (1992). *Proc. Natl. Acad. Sci. USA* 89:2581–2584.
Rano and Kidd (1989). *Nucl. Acids Res.* 17:8392.
Redston, M. S. et al. (1994). *Cancer Res.* 54:3025–3033.
Rigby, P. W. J., et al. (1977). *J. Mol. Biol.* 113:237–251.
Rommens, J. et al. (1995). *Genomics* 28:530–542.
Rosenberg, C. L., et al. (1991). *Proc. Natl. Acad. Sci. USA* 88:9638.
Rosenfeld, et al. (1992). *Cell* 68:143–155.
Ruggeri, B. et al. (1992). *Oncogene* 7:1503–1511.
Sambrook, J., et al. (1989). *Molecular cloning: A laboratory manual,* 2nd Ed. (Cold Spring Harbor Laboratory, Cold Spring Harbor, N.Y.).
Sanchez, I. et al. (1994). *Nature* 372:794–798.
Scharf (1986). *Science* 233:1076.
Scopes, R. (1982). *Protein Purification: Principles and Practice,* (Springer-Verlag, New York).
Serrano, M., et al. (1993). *Nature* 366:704.
Sheffield, V. C., et al. (1989). *Proc. Natl. Acad. Sci. USA* 86:232–236.
Shenk, et al. (1975). *Proc. Natl. Acad. Sci. USA* 72:989.
Shimada, et al. (1991). *J. Clin. Invest.* 88:1043–1047.
Shinkai, Y., et al. (1992). *Cell* 68:855.
Shoemaker, D. D., et al. (1996). *Nature Genetics* 14:450–456.
Snouwaert, J. N., et al. (1992). *Science* 257:1083.
Sorge, et al. (1984). *Mol. Cell. Biol.* 4:1730—1737.
Spruck III, C. H. et al. (1994). *Nature* 370:183–184.
Steck, P. A. et al. (1997). *Nature Genet.* 15:356–362.
Stewart, et al. (1992). *Hum. Gene Ther.* 3:267–275.
Stone, S., et al. (1995a). *Cancer Res.* 55:2988–2994.
Stone, S., et al. (1995b). *Oncogene* 11:987–991.
Stratford-Perricaudet, et al. (1990). *Hum. Gene Ther.* 1:241–256.
Tavtigian, S. V. et al. (1996). *Nature Genet.* 12:333–337.
Teng, D. H.-F. et al. (1996). *Nature Genet.* 13:241–244.
Valancius, V. and Smithies, O. (1991). *Mol. Cell Biol.* 11:1402.
Verheij, M. et al. (1996). *Nature* 380:75–79.
Vogelstein, B. et al. (1989). *Science* 244:207–211.
Vollrath, D., et al. (1992). *Science* 258:52–59.
Wagner, et al. (1990). *Proc. Natl. Acad. Sci. USA* 87:3410–3414.
Wagner, et al. (1991). *Proc. Natl. Acad. Sci. USA* 88:4255–4259.
Wang and Huang (1989). *Biochemistry* 28:9508–9514.
Wartell, R. M., et al. (1990). *Nucl. Acids Res.* 18:2699–2705.
Waskiewicz, A. J. and Cooper, J. (1995). *Curr. Opin. Cell Biol.* 7:798–805.
Wells, J. A. (1991). *Methods Enzymol.* 202:390–411.
Wetmur and Davidson (1968). *J. Mol. Biol.* 31:349–370.
White and Lalouel (1988). *Ann. Rev. Genet.* 22:259–279.
White, E. et al. (1994). In *The Molecular Genetics of Cancer,* Cold Spring Harbor Symposia on Quantitative Biology, Vol. LIX, 403–409 (Cold Spring Harbor Laboratory Press, New York).
Wilkinson, et al. (1992). *Nucleic Acids Res.* 20:2233–2239.
Withers, D. A., et al. (1991). *Mol. Cell. Biol.* 11:4846.
Wolff, et al. (1990). *Science* 247:1465–1468.
Wolff, et al. (1991). *BioTechniques* 11:474–485.
Wooster, R. et al. (1995). *Nature* 378:789–792.
Wu, et al. (1989a). *Genomics* 4:560–569.
Wu, et al. (1989b). *J. Biol. Chem.* 264:16985–16987.
Wu, et al. (1991). *J. Biol. Chem.* 266:14338–14342.
Xia, Z. et al. (1995). *Science* 270:1326–1331.
Yan, M. et al. (1994). *Nature* 372:798–800.
Yang, D. et al. (1997). *Proc. Natl. Acad. Sci. USA* 94:3004–3009.
Zenke, et al. (1990). *Proc. Natl. Acad. Sci. USA* 87:3655–3659.
Zheng, C. F. and Guan, K. L. (1993). *J. Biol. Chem.* 268:11435–11439.

List of Patents and Patent Applications

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,376,110
U.S. Pat. No. 4,486,530
U.S. Pat. No. 4,683,195
U.S. Pat. No. 4,683,202
U.S. Pat. No. 4,816,567
U.S. Pat. No. 4,868,105
U.S. Pat. No. 5,252,479
EPO Publication No. 225,807
European Patent Application Publication No. 0332435
Hitzeman et al., EP 73,675A
PCT published application WO 93/07282

What is claimed is:

1. An isolated DNA consisting any one of the DNAs having a sequence in the group consisting of SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45 and SEQ ID NO:46.

2. An isolated DNA comprising 13 nucleotides selected from the group consisting of:

(a) DNA defined by SEQ ID NO:40 having a T at nucleotide 285 wherein said isolated DNA consists of a fragment of SEQ ID NO:40 and includes the T at nucleotide 285;

(b) DNA defined by SEQ ID NO:41 having a T at nucleotide 421 wherein said isolated DNA consists of a fragment of SEQ ID NO:41 and includes the T at nucleotide 421;

(c) DNA defined by SEQ ID NO:43 having a G at nucleotide 117 wherein said isolated DNA consists of a fragment of SEQ ID NO:43 and includes the G at nucleotide 117;

(d) DNA defined by SEQ ID NO:43 having a A at nucleotide 136 wherein said isolated DNA consists of a fragment of SEQ ID NO:43 and includes the A at nucleotide 136;

(e) DNA defined by SEQ ID NO:44 having a C at nucleotide 1066 wherein said isolated DNA consists of a fragment of SEQ ID NO:44 and includes the C at nucleotide 1066.

3. A replicative cloning vector which comprises the isolated DNA of claim 2 and a replicon operative in a host cell.

4. An expression system which comprises the isolated DNA of claim 2 operably linked to suitable control sequences.

5. Recombinant host cells transformed with the replicative cloning vector of claim 3.

6. Recombinant host cells transformed with the expression system of claim 4.

7. A nucleic acid probe complementary to human altered MKK4 gene sequences wherein said nucleic acid probe hybridizes to a mutant MKK4 gene under hybridization conditions which prevent hybridizing of said nucleic acid probe to a wild-type MKK4 gene wherein said mutant MKK4 gene is selected from the group consisting of:

(a) a mutant MKK4 gene having a T at the nucleotide corresponding to base number 285 of SEQ ID NO:40;

(b) a mutant MKK4 gene having a T at the nucleotide corresponding to base number 421 of SEQ ID NO:41;

(c) a mutant MKK4 gene having a G at the nucleotide corresponding to base number 117 of SEQ ID NO:43;

(d) a mutant MKK4 gene having an A at the nucleotide corresponding to base number 136 of SEQ ID NO:43; and (e) a mutant MKK4 gene having a C at the nucleotide corresponding to base number 1066 of SEQ ID NO:44.

8. A pair of single-stranded DNA primers wherein use of said primers in a polymerase chain reaction results in amplication of a MKK4 gene fragment, wherein the sequence of said primers is derived from the intron regions of any one of the DNAs defined by SEQ ID NO: 36–46.

9. An isolated DNA comprising bases 21–1217 of SEQ ID NO:91 wherein said DNA contains a mutation selected from the group consisting of:

(a) a T at nucleotide 571;

(b) a T at nucleotide 681;

(c) a G at nucleotide 840;

(d) an A at nucleotide 859; and (e) a C at nucleotide 947.

* * * * *

UNITED STATES PATENT AND TRADEMARK OFFICE
CERTIFICATE OF CORRECTION

PATENT NO. : 5,989,885

DATED : 23 November 1999

INVENTOR(S) : David H.-F. TENG et al.

It is certified that error appears in the above-identified patent and that said Letters Patent is hereby corrected as shown below:

The correct title of the patent should read as follows:

[54] SPECIFIC MUTATIONS OF MAP KINASE KINASE 4 (MKK4) IN HUMAN TUMOR CELL LINES IDENTIFY IT AS A TUMOR SUPPRESSOR IN VARIOUS TYPES OF CANCER

Signed and Sealed this

Seventeenth Day of April, 2001

*Attest:*

NICHOLAS P. GODICI

*Attesting Officer*  *Acting Director of the United States Patent and Trademark Office*

SEQUENCE LISTING

```
(1) GENERAL INFORMATION:

(iii) NUMBER OF SEQUENCES: 96

(2) INFORMATION FOR SEQ ID NO:1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:1:

TTCTGTGGCA TCCTGATTC                                                19

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:2:

AAATGTAGCG GGGTAAAGC                                                19

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:3:

CCTTATTGCG AAAAAGTTC                                                19

(2) INFORMATION FOR SEQ ID NO:4:
```

```
    (i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:4:

GATACCTGGG CATTGAG                                                          17

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:5:

GATTATCCCA AACACAGCAT CA                                                    22

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:6:

AATGTATCTT TCTCCACCCT TC                                                    22

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:7:

TTGAGAAATT CCTCATGGCC                                                       20

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:8:

GGGATTCAGA GTAAACCTTG CT                                                    22

(2) INFORMATION FOR SEQ ID NO:9:
```

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Primer for STS."

(xi) SEQUENCE DESCRIPTION: SEQ ID NO:9:

CTGCTCAGTG CTGATGGGAT T                                              21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:10:

CTTCGGTCCT CCTAAATGTC T                                              21

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:11:

TTTAGTAGAG ATGGGGTTTC AC                                             22

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:12:

GACTATCAGA CTCTTCCTCC                                                20

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:13:

TTACTCATGT AATGTGGACC TG                                             22

(2) INFORMATION FOR SEQ ID NO:14:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:14:

GCAGAACATT TCTCGGGACT A                                              21

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:15:

ATCTAATCTG TCATTCATCT ATCCA                                          25

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:16:

AACTGCAGTG CTGCATCATA                                                20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:17:

AACTGCAGTG TTGCATCATA                                                20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:18:

TTCGACAATA GGCATAGCTG                                                20

(2) INFORMATION FOR SEQ ID NO:19:
```

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Primer for STS."

(xi) SEQUENCE DESCRIPTION: SEQ ID NO:19:

AGCTCATTCT TCAGAACTAA A                                        21

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:20:

AAGCTTTCCA AACCTCATCA                                          20

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:21:

CCAACTACAG GCTGAAGCA                                           19

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:22:

TTCCCATGGT TTTGTTATCA                                          20

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:23:

ACCAAATCCC GAAGATTAC                                           19

(2) INFORMATION FOR SEQ ID NO:24:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Primer for STS."

(xi) SEQUENCE DESCRIPTION: SEQ ID NO:24:

AGGTAAAAGC TGTATTCCAG AT                                              22

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:25:

TCCAAAAGTG TTTAGGATGA GT                                              22

(2) INFORMATION FOR SEQ ID NO:26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:26:

GATCACAAAA TACCATAAAC AAAC                                            24

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer for STS."

(xi) SEQUENCE DESCRIPTION: SEQ ID NO:27:

TGATGTGGCT TCAAAGGAAA TG                                              22

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:28:

CTGTAACCTT GGGCATCTTC                                                 20

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:29:

AGGATTTGGG CTCTTTTGTA A                                              21

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:30:

TGCACACAGT TGGCATTCAG                                                20

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:31:

CCCAGGAGAC AGCAGAAGA                                                 19

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:32:

ATCTAATCTG TCATTCATCT ATCCA                                          25

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:33:

AACTGCAGTG CTGCATCATA                                                20

(2) INFORMATION FOR SEQ ID NO:34:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Primer."

(xi) SEQUENCE DESCRIPTION: SEQ ID NO:34:

GGAGAAAGTG ATACAAGGGA                                           20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:35:

TAGTTAGATT AATACCCACC                                           20

(2) INFORMATION FOR SEQ ID NO:36:

(i) SEQUENCE CHARACTERISTICS:
        (A) LENGTH: 1078 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: exon
        (B) LOCATION: 593..727

(ix) FEATURE:
        (A) NAME/KEY: intron
        (B) LOCATION: 728..1078

(ix) FEATURE:
        (A) NAME/KEY: misc_feature
        (B) LOCATION: 613..615
        (D) OTHER INFORMATION: /note= "Putative translation start
            site."

(xi) SEQUENCE DESCRIPTION: SEQ ID NO:36:

AATGTAACTT TTAATTCAGT AGTTTTGGGA TGGTCCATGG ACAGCACTTT GGTTAGTTCC    60

CCTTGGGAYT CCCCTTTCCC YTCAGAGAAG TGTAGAGGGT TGGGGTATTG GGCTTAAGAG   120

GAGTTCCAGA CTGTAACCAT AGCTCTAGGT AACTCCCTTC TGGAAGTGAT GTGTTAGCGA   180

CTGGAGGAGA AAGGGATCCC TGGGATCCTT TTCAGCTTTA CTATTCTGAT TTGGGGTTCT   240

GAGATTCCAA CAAAGTGGAC TTTTGGGAGT CACAGACCTC CATGGGAATG ATGAAAGCTG   300

CGTACCTTCT TTCCGCACAA ATGCAGGCCC ACCTTTAATT CTGCAAACCA CTTTAGGCCC   360

CGCGGGCCCG CAGCCCTGGT CCAAGACAGC TGTCTGCTTC ACAGGTCGCG CACCCAGAGC   420

CGGGCGGTTC TGCAGCTCAG CATCTGGCCC GGGCTGCGCG TCGGGCTCTG GCGGGGGCGT   480

GTCAGGAGGC GTGTCCGGGG CGTGTCGGAG GCGGGGCCAA GGCGGGGGCA AGCCTCGCCC   540

CTCGGCCGTG CGAGAGGCCG AGCTTGCTGC ATTGCAGCCG CCGCGGCGCC GCTGGGCTCT   600

```
TCACTCCCAA CAATGGCGGC TCCGAGCCCG AGCGGCGGCG GCGGCTCCGG GGGCGGCAGC      660

GGCAGCGGCA CCCCCGGCCC CGTAGGGTCC CCGGCGCCAG GCCACCCGGC CGTCAGCAGC      720

ATGCAGGGTA AGGAACGCGG CCGCGCCGAG ATCCCAGCCC CCTAGCGCGG CAACCCGCGT      780

CGTCGCGGCC TGCCCCAGCG GACGCCCCCG GACCCGGCTG AGGAAGCCAC GGCAGCCGCC      840

GGCTTCTCCC TCTCTCCCTC CCCGGCTTCC CGCCCCGCTT CCGGCCGCCT CCGGCCCGGC      900

TTGGATCCGG GCTCCGGCCC GCATAGGCCC CGGCCGCGGC CTCTGCCTGC GCTTGGCCCC      960

TGGGCCCTAC CGGGCTCTCA GCCGGCCCGC ARGGCCCACC TGGTCCGGGA CCGCCCCCGC     1020

GGGCGTCCCC ATCGCCCCGC CGCTTAMCTG GCGCCCGCCC GGCCCCGTTT CCGGGAAC      1078

(2) INFORMATION FOR SEQ ID NO:37:

(i) SEQUENCE CHARACTERISTICS:
        (A) LENGTH: 1620 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: intron
        (B) LOCATION: 1..1325

(ix) FEATURE:
        (A) NAME/KEY: exon
        (B) LOCATION: 1326..1428

(ix) FEATURE:
        (A) NAME/KEY: intron
        (B) LOCATION: 1429..1620

(xi) SEQUENCE DESCRIPTION: SEQ ID NO:37:

TCGGATCTGC TATGTTTCCT AGTGTACCCT TTGCACATGT TGTTTGAATG TCCTTCCTCT       60

ACATTATGTG GAAAAGTCAT ACTGTACTAA CCTTATTTCT GAAAATGGAT GTGTTTGGTC      120

TTCGTGGGAA TTCACATGAT CTGGTAGAAA NGGAGGCTTA TCTTTGAAAG CAGATCTAGG      180

GGCCGTGGCA AGGAGCTCTG TGCTCTTGTC TCTTTGCCAT CTTCTCCATC CAGTGTGGCT      240

CCGTCAGATT TTCAGATCTC ACATTTACAG TTTGAACCCT CTATTAAATC CTCATCCACT      300

GAGGTCAGAA AGTGTTTGGA TTGCAGAGAT ATTTTTTGAG TAGTTAATTG TATAATAAAC      360

TCTAGAGAGT GAGTTCAGGA AAAAGTGTCT CTAAGGTGAA TGTGAAACCA AGATATGCTG      420

CAAATGCTTA AAAAATTCAG TTCTGTTACA AGGTATCCTT TTAAGTCCTA AAGAAATGAT      480

TCTGTAAGAC TTATTGATAT AGAAAGAAAT GTTAGTGAAT AAAGCATTTT ACAAAGCATT      540

TTCATGGTCT GATTTCCAAT TGTAGTGAAA AAATACATGT CCCTATCTAT GTATAGAAAA      600

AAGTCTGCAG TAGTTAGTAA ACTGATTATT TTGAGATACT TGGATTGATA AGTTTATGTA      660

AAATTTTAAC CCTATGTATT GTATAGGTGT ATATGTAACA TTTTTAATAT ATTTGATCTT      720

TTTTTGCATT TTCTGCCCTT CTACCATGGT GGTTTTACTT GGGTAATAAA AACATTGGT       780

ATCTCTTCCC TTCCTACCCT AAAGAAACAG CTTCATGGAA ATAATTATTT AGAATACTTG      840

TATTACTAAC TTGAAGTTTA CTCTACCGTA ATGTTTTTAG CAAATTTTTC AGATTCTTCA      900

CCTGTTGTTT ATATTCATTA AAATGAGGGA AAACGATATT TATTAAACTG AGGGCATTAA      960

GTATAACACT GAACAGATGG TAATATTTTT AGAATTTTTC AGTATATCTA CTGAGATAAT     1020
```

```
TGATTTTTAT AATAGTATTT TCACTTGCAA AAGTATTAAC TTCCCTGAAT AATGGAAACT      1080

TGAAGTGATN GCATTCCTAT CTATGGTATC ATAGCCTAGT GAATGATTTG TACTTAGTAA      1140

CAACTTTAGA TTATTTTATT TTTTCTTAGT TTGAGAAATT CCTCATTGCC TTTCAAAATA      1200

TTGTCCTATA TTAACTGTTT GTTAAAGCAA GTTCTCTTGC CTTTTGGTGT GACTTTCTTA      1260

TGCCCTCAGA ATAGTACCTG TTTTGTAGTA CTTGAAACTT TTACTTTTTA TTTGTTATTT      1320

CTCAGGTAAA CGCAAAGCAC TGAAGTTGAA TTTTGCAAAT CCACCTTTCA AATCTACAGC      1380

AAGGTTTACT CTGAATCCCA ATCCTACAGG AGTTCAAAAC CCACACATGT GAGTATTCTT      1440

GGTAATCAAA GGCTCAACTC AAGCAAAGAT TTTAAAGTTA CTGTATTTTA TGAATTTTTC      1500

CAATTATGAG ATGTCAGTAT AATTTCTCTG ACTAAACTCT CTGGGAATAT TGTTTATTCT      1560

TTTCCTTCTG GAGTTCCAGT TAAATTGCAA GTTGCATTTA GGAAATTTGA CTGTCTTCTG      1620

(2) INFORMATION FOR SEQ ID NO:38:

(i) SEQUENCE CHARACTERISTICS:
        (A) LENGTH: 4619 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: intron
        (B) LOCATION: 1..620

(ix) FEATURE:
        (A) NAME/KEY: exon
        (B) LOCATION: 621..795

(ix) FEATURE:
        (A) NAME/KEY: intron
        (B) LOCATION: 796..4619

(xi) SEQUENCE DESCRIPTION: SEQ ID NO:38:

AGTTCCCAAA CATTACTNGA ATCATCTGGG GGNCTTTAAA ANTACTGTNT CCTGNCTCCT       60

GTCCCTGGAT AATTCAGATG TAATTGCTAT GGGACGATAC CTGGGCATTG AGATTTTTAA      120

AATCTCCCCC AGGTGATTGT AAGGTACAGC AAACCTTGGG AATAGTTGTA CTAACTGAAG      180

ATTGAGGCAC TGGAATAACT AATGTTGGGT AAGATAGGGT AAGAACTTTT TCGCAATAAG      240

GTTTGCAGCT CTTGGGATTC TCACTTGATA ATGCTGTTTG GATAAACCAT CATCCAAGTT      300

TGAATAAGAT CTTATATTTA GAAATGAAAA CTGATCTGCA GAATTAGTTT AATCAATAAA      360

TGGGAATTTT TAAAAATCTT CTTGGCAATT TGTTTTTATG AATCCCGTTG AAGCTGTGTC      420

TATTGACTAC CTAAATCTAG ATCATTCTTA ATCCAGTGTG TAAAAAACCA GGATGACACA      480

AATGAAAAAC TTCAAAAACC TGGAGGTCAG ACTATTTTAG TAATTTAGAA AACATTTTTC      540

CCACACATTA ATCAGTACTA AAAGAAAAAA GTTAAAACCT ATTTAAAATG TGGAAAAATT      600

GCTTCCCAAT ATTTTAACAG AGAGAGACTG AGAACACACA GCATTGAGTC ATCAGGAAAA      660

CTGAAGATCT CCCCTGAACA ACACTGGGAT TTCACTGCAG AGGACTTGAA AGACCTTGGA      720

GAAATTGGAC GAGGAGCTTA TGGTTCTGTC AACAAAATGG TCCACAAACC AAGTGGGCAA      780

ATAATGGCAG TTAAAGTAGG TGATGCCATG ATTATTTTTG GTACTTTAAT CCATTAGGTG      840

AAATTTCATG GTGCAGTAAT ACCACTGTTG TTGTGTTCCT ACTTTTGTGG TAAATGTGGG      900

TGTTTAAAAA ATTGTTTCTC CAACTCCTTT GAGGGTGTTC TGTGTAGAGG TTTCTTATTG      960
```

```
GTGGCACATT TTCTATCTCT TTGGAAACAT GAGTGTATGA AGTGTGCATG TTGATTGCAT    1020

TTTTGGCATG ATGCATTAAC ATGTTTTAAA CTTCAGGCCC TTCTACTGCC AAGGTGAGTT    1080

CAGGCTGGGC GGCTGCACCC CTGGGAGCAG GGCAGTGCTG CACTGAGCCA GGCGGGAGCT    1140

GGAAGAAGAC GCAGCACACT GGGTTGGGCA AGGTGCGGGG CTAGGGCTAA CAGCAGTCTT    1200

ACTGAAGGTT TCCTGGAAAC CACGCACATG CTGTTGCCAC TAACCTCAAC CTTACTCGGT    1260

CCTGACCGGC TCGGCTTCTG TTTGTTTATT TCATCTCTAC TCAGTACTGC CCTGTTCCCT    1320

GGTTTTAAAG TTGTACTGAA ATGCATACCT TGTGATAATG TTGTCACATT TTGTCCNTAT    1380

TGGGTCGGGC CACTTAATAT GTNCCTTAAA AAAAAAAAAT GGCCAGAAAC AGAGATTTGA    1440

TCCATAGACA ACACCTGGCA AGCTTATGCT GGGTACCTGT AAAGAACTGG TGGTTTCCAT    1500

CTGACTCCTA GTTTCATGTA ATTGTAATTT ATTCATTTGT TTGTTTAGAT GTTAACAAA     1560

TCTTTGCTGT ATGTAAGATA TTTCAGGAAA ATCAGCAACA GGGGGAACAA CTTGCAAAAA    1620

CAAAGGAAAA AAAGCTAGCT GTGGCCATAC CCTCTCTGAG CTTAAAATTC CTATGGGAAC    1680

AAAAATGTTT CAGTTTACAA GAATTCAGAA TGGATTTGCA TATAGTCCAA GCTAATCATC    1740

TTCCTATTAG TGTCCTATTT TGAGAGTTTG TCAGAGTGGT TGATAAGAGT CCTTAGTTTT    1800

TTCTTGACAT TTGAGAATGA ATTTAAATTA AAATAAAATG CTTTCTGTGT AGAAGTCTGT    1860

TGTGAGCCAA ACCTTACTGT AACTATTTTA GTATCCTTCA CTGTTGAGCA TTTCTTTTTG    1920

CTGGGTCATA TGAAAGTAAT GTTAAATTAG TGGTAGGGAA AATTTTTATG ATTCTCTCTA    1980

TGGGTTCCTA ACATTGTTTT TGGCTGTATT TTTAAAATGT GGTGAGAACT ATAGACTTTT    2040

CATAGGCAGG TGTATATACA CAACATTTTG TATACAAACC GTAGACCTCT AAAGATGCAC    2100

AGGTGAAGAA CTCTGCATTA TGTGTTAAAA TAAAATGTTT TATTGGAATG TGAAATGATT    2160

TCTGTATTCC TATTTTGTGC CACTGCAGTG TAAGTGGAAA GAGTCATTTT ATTTAGACTC    2220

CTGGATGAAT GTTGTGTTGT CCCTTTGTGC TACCTGTGTG TGACATCCAG TTTTAGTTGG    2280

CTGGATCTTA AGGGAAAGGT TTCCTATATA GTTAAAGTTG TAAACTTTTC TTTCAGGTAC    2340

TAGGGAAAGT AATTTTAAAA AATTATTTCC TGCTTTTTAC AGTTTGTGTT ATGTGTGCTT    2400

CAACTTTGTT GATGAACATT ATTAAACATT TTAGTAATAT GGATTGATTT TAGCCATTGT    2460

TAAAAAGGTC ATAAAGGTAA AGAGGGTACT TCCTTTTGAC ACTTAAAAGT TTTTCTCACT    2520

GATTAATTTG ATAATATTTT GGGTTGTATA ATGCTTACTC AAGTTTTGTA GGAATTCAAG    2580

AATGAAAATA GGAAATTGTT GTCCATCATT TGTAATGTTA CATTATCAGT GGCTACTGGC    2640

TACTGTGACA GTTCCAGTTG GGATGCTATT AAAAATCCCA GCTGTACTTG AAGAACTTTC    2700

AAGGCAGTCA TGAGACCTAC AAACTGGTTG CTGTCACATG TATACCCACC ACATGGTACT    2760

ACCTAGCTTC GTTACCATC  TCGAATTCTT GAACAAGCAT AGCAGTTGGG GATGGGAGAG    2820

GATGGCAGTA CAACACATCA ATTAACATAT AGTTGAGGAG TACCTTTGGA TTCCATGACT    2880

TCATTAATAC TGGAAGAATA AGTGTTTTTG CATTAATATG CATTAAAATT TGATACCAAT    2940

TGATGACAGA TGTATGCCAT CTCTGAATTA AAGAATGCAT TTATTATTGG TTTCTTCAAA    3000

GAAGAATAGT CTTTCATCAC ACTTGAGAGA GTTCATTCAT TCCTCATTTA GGTACATTGA    3060

CTGGATTGAC AGGCACAAAT ATACAGAATC AATGTATGAT TAAGGAGGTG TTTGATTTGA    3120

GACTTTACGG TTTTAAAGGA ACCATGAGAC GGTGGTTCAC ACAGCTGAGA GCTTTCCATT    3180

GCTGTTGGTG AAATGAGAAA CACGCTTGAA GTAACTCTGT GCTAACATCT TAATACACAC    3240

TTTGAGAATA AAGAAGGATT GCATTATTAG ATGTTAAGCT GGAAATGATC CTTAAGATTT    3300

ACTTGCAATA TCTGTAGAAA AGTGAACTGT GATATTAGCT TGATTTTTTT CTTTGTATTA    3360
```

```
TTCCTCATTT TTAGTTCTGA GGAATTCCTT CCCCAAATTT ATTTTGCCAT ATATAAGAAA      3420

TATTTGAAAA AGGTGACTTC TTAGTAACCA GAGTTAATTA CCCCAAAGAC TTAATCTAAA      3480

AATCAGTTTT GATATAATCA GATTTAGTGA GGTAACATTG TAAGAGTTAT ACTTAAAACA      3540

ATTTTTTGAT GTTTGGTTTG AGGACAGTCT CCCAAGCTAT CGGTGAGTTT CTGCATTAGG      3600

ACCTAAGATG TGAACATGGT TTACCCTTTA GTTTTAATTG CACGTGCTTG GGAAAAGGGT      3660

CTTGCTCTCC TGTGAGTGGG AGTAATTTGT ATACTTGTGC CTGAATGACT AGTCTTAGGG      3720

CTGCCTAGGG CAAAGCCAGT GTTGCCTCTG GGGTTTCTTA AAGCTCAGGG AGAACAACCT      3780

TCAACTCTTA CCAGGGATTT ACTTCTAACT GTGATCAGTA TCCTTTACAA ATAACATTTA      3840

TTTAGTGTCC TGTTTTGCAT GGTGGTGGGG TAACCACTGA ATGAAAACAT TAGACATGAA      3900

CAGTCACTGT CCTCTACATA AAGTAGGTGC CTGCTCAGCT CTCTGGCAGG TGGAAATGGG      3960

AGAGGATGGC AATACAACAC ATCAATTAAC ATATAGATGA GGAGTACCTC ATCTATATGT      4020

TAACCAGCTC TCTGGTTAAA TGTAGCGGGG TAAAGCCCAG AGTTCAGACC AAATGTTTGA      4080

AGAGGCAGTT AGGATTAGGT TTCTGAGCTA GGGTAATTCA GATCTGGGAG AAACACCTAG      4140

CATCATCAGT CAGAATCAGG ATGCCACAGA AAATCTAGGG ACACAGGAGA AAAGAGAGTA      4200

AATGAAATGT CACAGCTTAG ACCATGGGCT TACAAGCTCA GATGGCTGAC AGAGGGAAGA      4260

ATGACTGTAA GCCTCTGATG CCTGACAGTA TATTCTCCAC CTGACTCTGC CTGCAGTGTA      4320

AAAAATCCTG CATGCCTAGA GTACCAGCTT CCCTGTTGTT TTCTAGCAGA CTCATGTCCA      4380

GATTGACTTC TTGAAGGTAT GCATGCCCTT TTCATGTTTG TAGAATATGT GCGAAAAACC      4440

AAAGAAACGT GAAAAAGTAA GAATGAAAAT GAGAGGGAGT ATAAGGACTG AAGTACCTGT      4500

CACTAAAGAT GATGGCAGGC AGTGGAATCT GAATTGTTGT GTGAAGGGTT AATACTGTAA      4560

TAAAGCTGTC ATCTCATTGA AGAACTGAAT AATATTGAGC AGGTAGGTGG GAATAAGAA      4619
```

(2) INFORMATION FOR SEQ ID NO:39:

(i) SEQUENCE CHARACTERISTICS:
        (A) LENGTH: 1240 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: intron
        (B) LOCATION: 1..937

(ix) FEATURE:
        (A) NAME/KEY: exon
        (B) LOCATION: 938..1057

(ix) FEATURE:
        (A) NAME/KEY: intron
        (B) LOCATION: 1058..1240

(xi) SEQUENCE DESCRIPTION: SEQ ID NO:39:

```
TATTTTTTTA TAATTTCTGA ACATGATTCT TTCCTATATT GTCCCTCCCA ACACCTCTGT        60

GTTCTATACT GTTCCTGAAT AAGAGGTGGG AGGAGGTGGG GAACTTAATG TTTTCTGGCA       120

GTCTCTTAGA AATGTGCAAA GAATTGTTG TACAGCTTGG TTAGGAATAT ATCCCTGGTC       180

TGCAGTATAT GGAGGAGCGC TTTAGCACCT TAGGAATAGA CAAAAAGAGC CCTCTGTTTC       240
```

```
CTCAGTTTTA GGTTTTCTTC CACAGGTTTA TGCTGCCCTA CATGCTGACT CATGGGTTGG      300

AGAGTCAGGT AGAACTTTTT GTTTTTAATG TATAGAAAGT GCAGTTAAAG GACAGAGTCC      360

CAATCTAGGA TTTTGGAGAC CTGGATTCTT GCCTGGTGCA CTGCTCCTAT ACTAGTATTC      420

ACTTTATCCG GTTCTGGACT ATTTCCCGTC TTTATGAATG AGGACACTGT GGTATGAGTG      480

TCCTCATGAG TGAATGAGTG AAGAGGGATG TTCTTGCATT GAATGCCTAG ATTGCATACA      540

ATTTTGAAAC GGTGATTAAA AGTATGTATA CAGCTACCTA TAATTATTCA TATGAAACTG      600

TTAAAACTCA TTATCATTTT CTTTATATTT GCATGTGGGG GTTAATTTTT ACTGCCTAAG      660

AACTTTGTTG CATAACTCCC AACATTATTA GTAAATGCTC ATGGTTAAAT TGCCCTGTCT      720

CCTTTAAAGG ATTTCTAAGT GCTGTTTGTT AAACTTTCTG TGATTAAAGT AATTCTTGTG      780

AAGTATAAGG AAAGATGATA ATTTTCATAT CTGGTATTTG TGAAGTTTGG TAATTTTTAG      840

TCTCGTAACG GTTTTCTCT ACCATGAGAC TAAAAATTAT TGGTGTTTTT GACAAAATTA      900

TTGTGTTTTT TTGACATCTT TTGTCATTCT TTTCCAGAGA ATTCGGTCAA CAGTGGATGA      960

AAAAGAACAA AAACAACTTC TTATGGATTT GGATGTAGTA ATGCGGAGTA GTGATTGCCC     1020

ATACATTGTT CAGTTTTATG GTGCACTCTT CAGAGAGGTA GGAATAAACT GGGTTTTAGC     1080

TGACTAATGA ATATCTAATT GGGACAAATG AAGATGGCAG GATTCGATTC TATTCTTAAA     1140

TGCCATACAT TAGTAATAAG TTAATATCTC AGTATCTTAG TGTTTAACCA TGATAATTTA     1200

CATATTAACT TCTGACTCTT TTTGCGGTGG TGGKTAAGGG                            1240

(2) INFORMATION FOR SEQ ID NO:40:

(i) SEQUENCE CHARACTERISTICS:
        (A) LENGTH: 2167 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: intron
        (B) LOCATION: 1..247

(ix) FEATURE:
        (A) NAME/KEY: exon
        (B) LOCATION: 248..367

(ix) FEATURE:
        (A) NAME/KEY: intron
        (B) LOCATION: 368..2167

(xi) SEQUENCE DESCRIPTION: SEQ ID NO:40:

CTGTGTAAGC CTGTCCCTGT CCATACAATT AAAGAGTGGG GAAAATTGGC TTTAACTACA       60

TTGTTTATGT TTAAACCTGA GTAGAATATT CTGTTGAAGG CTTTAACAAG AAAACAAAAA      120

TTATTACTAG TTTGACATTT GAAATAAGCA AGAATAAGAT TGCTCCTTTC TATTGTATTT      180

CCATTTTAAG TAAAGGCAAG GTGATATTTA AGATGTATAA GAATAACAGA TATTTGTTAT      240

TTTATAGGGT GACTGTTGGA TCTGTATGGA ACTCATGTCT ACCTCGTTTG ATAAGTTTTA      300

CAAATATGTA TATAGTGTAT TAGATGATGT TATTCCAGAA GAAATTTTAG GCAAAATCAC      360

TTTAGCAGTA AGTACCTGGT CTTTAAATTA TTCATTGTGT ATATAGTTAT ATAGAGATGC      420

TGCTGGAGTT TTGAATGCAC ATATTTGAGT GTCACTCACA GTACCTTCCT GAAAATAATT      480

CATAGTTAAT AACCAGAGAC AAAGTCACTT CTGTGGGGTA GTTAACACAA TAGGTCATAA      540
```

-continued

```
TGGTCTCGAT AAATACTGCC AATGTTCTTT CCCTTTGAAT CTCAATGAGT CATAACAGAC     600

TGTTCTGTAA ATAAAGCTAG GAAAAGCAAT TTTCTGTTCA TTTTTTCCTG TTGCTTTAAC     660

TATTTTTAAA TAGGTTATAT TACCACAGTT ATCCTGAAAT TAATCAGAAT CACAGCAGTC     720

TCCTTGAAGC CCCATAATTG AAGCCCTTGG ACAAAGTTTG TTTACTGTGA TTTAAGATTT     780

TGGTTACTCC ATAATTGAAG CCCTTGGACA AGTATGTTTT ACTGTGATTT AAGATTTTGG     840

TTATTCAGTC TAAACTATTT AAAATTTTGA CTAGCAGTTT CAGGGGCCAG TGTTACTACT     900

AAATTTGGTT AACTCACTTT TACCAGAGTA CCAAAAAAGA AAATAGCTAC TTTTTTACAT     960

ATGTGTTTAT AGTTTTGAAA GTGAATTGAT CACTTTGTTT CTTGCTCTGA ATCTTAATTT    1020

TTTTTCCTAA AGGAAAAAGA TAATTTACTT TTTATAGAGC AAAATTCATA AGATTCTTAG    1080

AAACTCCTGA GAATCTGAGC TAATGGCATG TTCTAGGTTA GTTGATATAT AAACTAAATC    1140

ATACAGGAAA TTGTAAAATA GATACTTTGG TTNGCACGTA ATTCCCTAGC TCTTCCTTAC    1200

CGGCATACTC CCCCTCCAAT GTAGTCCACC AAGATATATA CTCTTTCAAA TAATTTCATA    1260

AAAAGATTTT ATGAAATCAT TTTATTTTTA AATTTTATAA AAATAATTGT ATAAAAAGAA    1320

GCTAACTTAG ACTAGAAACT TATTATTTAG CGGGGTATAT GAAATTTTAC AATGATTAGT    1380

TTAGCCATCT CTCTCTAATA TATTAAACCC GTGTTATCTT GAAACTTACT ATTTGTAATA    1440

ATTATAATAA TAGAAAAATG ATAATAGCTA ATGGTTATTA AATGCTTATT TGCATCAAAC    1500

TATTTGTGAC ATTAAATCTT CATAGTAACT CTCTGTGGTA AATAGTGTTA CCTCATTTTT    1560

ATGAATGATA AATCTGAAGC ATAGACAGAT TAAATAATTA ATATGCTTTG AAGTGTGTAA    1620

GTGGTAAATA ATCTAAATCC AGGCAGCCTG ATCCCAGAAC CCTGCTCTTA ACCGCTGTAT    1680

AACAGGGTGA CCATGAAATT AGAAAACAGA AAATTATTTT ATCATATATT GCAATATAAA    1740

GAATATATAC TGTAAAAAAT GATTTATTCC ATATTTGCCT AAGTCAAGAC TTGGTGATCA    1800

CTTTATATAT ATTAAGCACA CATGTAAAAT ACTTTGTGTT TAGTCTCTTC TTGCTAATTA    1860

ATAAACCAGC AAACAAGCAT AGCTATTCAC AACAAATTTA TGTGTTCTAC ATTTCTTGTA    1920

CCTAGCAGCT TGACGTCAGC AAAGACGTCA CCTTACAGCA AATAGTTGGC CTGTTGTTTA    1980

GTTCTCTTTT AGTTTGAGGT TGTGTCTCTT TTCCTTCCCT TCCTGAAGAA ATGTGTAATT    2040

TTCTGATCAT GATCAGTGAC CAGGCAACAG GATAAATTCC CACAGTGGTG AACAGAGTTA    2100

CACTAGCTCT TCAAACATCA CCTTGAAGGC TTAGCATCCA ATGAGGGTNG ATGATGATGA    2160

GGAACTG                                                              2167
```

(2) INFORMATION FOR SEQ ID NO:41:

(i) SEQUENCE CHARACTERISTICS:
        (A) LENGTH: 1485 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: intron
        (B) LOCATION: 1..393

(ix) FEATURE:
        (A) NAME/KEY: exon
        (B) LOCATION: 394..445

(ix) FEATURE:
    (A) NAME/KEY: intron
    (B) LOCATION: 446..1485

(xi) SEQUENCE DESCRIPTION: SEQ ID NO:41:

```
TAGCCAGGCA TGCATCTGTA GTCCCAGCTA CTTGGCAGGC TTTGGTGGGA GCGAGACCCA      60
GTCTCAAAAT AAAAGGGAA AAAAAAAAG GAAATTTTAG GTTGGAGATA GGAAAAAAGA        120
TAAAATTTTA AATGAATTAT TAAACAAATT ATAAGTCTAA GTTACTGGGT TTTTTGTTTG      180
TTTGAGCTAT CAGGGAACAG CATATAAAGG CAACTAAGCT TTTAGATCTA AAATTATTCA      240
GTATCTTTGG TTAACAAGAA ATGACAAAAT ATTGAAATAT TAAGCTTAAA ATGTATGCAG      300
AGGACTACAC GGGATATTAC TTGTGATAAA CTGTTGTGCT GTTTGAATAA AAAGAAACAA      360
GTTGTTTATC CCATCTCTCC TTTTTCTCCC TAGACTGTGA AAGCACTAAA CCACTTAAAA      420
GAAAACTTGA AAATTATTCA CAGAGGTGGG TATGGATTGG TATTTTTTGT AATAGAAATT      480
AACTTTTTTC TCCTAATTGG TGAAACGGTT ATTGAAAATT ACAGTGTCAC TGTATAAACT      540
TTCCTAAAAT ATTTGTATTT TTAGCAAAAA ATGCTTTATG TACTTTAAAA CTCTATTACT      600
GCTATTTTTC TCTCTGGGAT TCAATAAATT TCAGTCTATC TTAGTATGTT GGACTTAGAA      660
ACTGAAATAG ATTTTGCTGC ACATTGTTAT TAGTTGAAAA ATAATTATTC ATTTGCCTGA      720
TAGATAATGT TTTTCTGCAT ACAAATAAGG CATCGAGGTG GTCCTGTGGA CATTCAAAGA      780
AGAATCTGAG GGATAGTACC CTCAAGCATT TTAAAGGCAT GCTATCCCTG TCTGTTGTTT      840
CTTCTTCACA TTGAGGATG TTTCTAAATT GAGAGAAATC TTTTAATTAG TATTATAAGT       900
TGAAATTTCT CTAAAGCATG TTGTATTTGT GTAAACAGTG ATCTTGCCTT TATTAGATAC      960
ATATTCAAAT GAAGCATTTG ATGTAGTTGA AGGCCAGACC TAGAAAAGTA GTAACCCTGT     1020
GGGAATCCTG AATTTAATCT GGCAAATAGA TGAAGTGCTT GCTTTACTTA TTACTGTGCT     1080
AGACTCAGGG TAATGAGGTG CTGGCTTTGA GGAAACACAC CGAATCACTA CCCCTCAGCA     1140
AATTTGTAAC GGAAAAACCT GACAGTAAGT GGCAGTGTGT GATTTAGCCT GACAGTAAAT     1200
AGGAAGGAAA GTAAAGGGTC AAAATGAAGA GAAGTGAAAA ATTTCTAATT CTGGGAGACA     1260
ATTTCTAGTG GTTAAAGAAA TTAGTAATTG GGCCATTTAT TTAAGTTCTT TTGTTTGTGG     1320
TTGACACTAG GCCACTGAAA TTAGTGAACC TTGAACATCA GTAAATTTTA TTTAATTTTG     1380
TTTGGCTTAA TGCTTGTTAG AAATAATATC TTTTTTTCTT TTGGCCTAAA ATTATGTAGA     1440
GTTAGGTCCC TAAACAAAAT TCTTTGTTTC TCTTGTATTT CTTCT                     1485
```

(2) INFORMATION FOR SEQ ID NO:42:

(i) SEQUENCE CHARACTERISTICS:
      (A) LENGTH: 2799 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: intron
      (B) LOCATION: 1..764

(ix) FEATURE:
      (A) NAME/KEY: exon
      (B) LOCATION: 765..892

(ix) FEATURE:

(A) NAME/KEY: intron
(B) LOCATION: 893..2799

(xi) SEQUENCE DESCRIPTION: SEQ ID NO:42:

```
AAAAAAAAAA AAAAAAAGCA TGGATGGTTA GGAATGGATG TTTGATAGGC CCACAGCTGT     60
TTCGGTCATG GTAAGAGATC TTTACTGAAT TTTTTTGTGG ATCACCTTCT GAGTTACATT    120
TAGATGTTTT CTGCATCCTA TATTTTAAAA CCTTATTTTT TATTCATTGA GCCAGGATAG    180
TGACAAGGAC ATGGATAAAA GGACTGAGCT ATGGATAGAG AATTAGTTGG CACATACTGG    240
TAGTGACTTG ATTGTCAATG AGAAAGGGAT TTGACATTCC TTATATTTTG ACTGTTATGT    300
AATGAATCTG GACTAAGTAA ATGAATTTGT AAGCCTCTTG AAAACAATTT AATGCCTAAA    360
TTTCTTGTGA AAATTTTTTT TGATATTCAG TTTTTAAGCA CTGGCATTCA GAAAATTGTT    420
TTCCTTTCTC ATTTTCAATA GAAGAAAACC ATTGTTTTTT CTGTGTTTTA TAAATATGAA    480
GATGTTAAGA GAAAAATCAA TCCCCATCTA TATCTTACAG ATTAATGTTT GTGAAATGAC    540
TTTTGCTGTT ACATTTACAC AATTATAGTT ATTAAAGCTA CATGTTTAAA ACATGAATAA    600
TTATTGTATG TGATAAATGA AGATGTTTTA CTTCTTATAT ATCTGAATTT AAGGACTTGA    660
CCACTTATGT TGTCTAAGGT TTTTCAATAT TTTTGCTTAA AGTGAAGCCT TATGTAACTT    720
AGGAAGAAGC TAATTGTATA CTGAATGATA TCTATGTCTT GCAGATATCA AACCTTCCAA    780
TATTCTTCTG GACAGAAGTG GAAATATTAA GCTCTGTGAC TTCGGCATCA GTGGACAGCT    840
TGTGGACTCT ATTGCCAAGA CAAGAGATGC TGGCTGTAGG CCATACATGG CAGTAAGTGT    900
TAAGTCCAGG CCTTCTTGCT TGATAGTCAT TGCACAGAGA GCCTGTGCTC TTTTGTGCTG    960
GCCATTAGTC ATACGGTTTT ACCATGAAAC TGCTAGAATA TTTCCCTTAC CCTAAGGCCC   1020
AAGCTCAGGT CCTAGCCTCT CCATGAAACT TGCTAAATT ATCCCAGTCA GCTCCTGTTT    1080
TCATTGTCTT GCTTTATTTC TCTTACTTGG TATTTAGCAG TTGTGGTCTT CTCTGATTAT   1140
TGTTTTTTCA TTATATTGAA CTCAACTCAT TAAACAGATG GTAACTTCTC AGAAAGTTCC   1200
CACCGTCCCT TAGTGAGACA AATGGGAAGC CTTGAGTTCA TTAGCAGAAT TCACTATGTA   1260
TTACAGAGTC TGAAGCTGCA TATTTTGAAT ATTGTTAGTC CTTTTTTTTA GGGGTAGATG   1320
AAGCACACCA ACAAATGCAA AGGTAGAGGC CTTCAGTATT TTGCAACCTG GAGCCTCTTT   1380
TCCTGCAAAG AGACAGATGT ACACTATCCA TCCATAGATA TCAAACTCAT CTTACCCCAG   1440
TATATTTGCA TACAGTGTTC CTACAGCCTG GATTTTGATC TGTATTTGAA TGAAAATGTA   1500
GTGTCTGTAT TTCAGACATT TCCCTAGGTG TTAATGTCTT TCTTCAATGT TGCCATGGTT   1560
CTTTGGGGAC CAGCACACTA CTAAATGTGA CACATAAGGT TTTGTGGTTG TTTCTTGAGG   1620
CCTCCCTGCC AGCAGCATTT CTTTCCATCT TTGTAGACTC TTTTAAACTA AAGATAAGCT   1680
TAGAATTGNA TNAAAATTGT TCTTTCTTGG TTTCCTCCTT GATATATATG TTTTCAAACC   1740
TAGTGCTATA ATAATAAAA AAGTAAGAGT CACAGGCTAG ATATTATAGG TGTTCTAGAT    1800
TATTTATGAA TGGATAGGCT TAGTGCTACT ACAAATTCAA CTTACTGCAT TTTTCAATCC   1860
TCTTTTGGTT TTGTTATATC TTCCCATATC ACTTTTTCTT CAGATGAACA TGTAAAAGCG   1920
GTGTGTGTGT GTGTGTAGAC ACCTAACCTG TGTGGTAAGA CCTTTTAAAC TTTTGGTTTT   1980
GTGGATGTTG ACTGGCTGGG CAGATTTCTT GACTCAGTTT GGAAGATCAT TGTTTATCG    2040
TGATAACTAG GGATAAATGG CACAATAGTT TCAAAGGCAA GAAATAAAAA AAATTAGACA   2100
TGGAGTATTT GGGAAATGTG ATTTACATAT TTATTAAGGA TACCCGAGA ATGAACTGAA    2160
ATTGTTATTT ACAGTTTTAG GGCTTGTCTC GATACTAACA GTGACTAAAT GTTTTTGTTG   2220
TGTGACACTG ACTAAGAATT ATATTTGATT GAAGCAGGCT TTGAAAATGC AATTGCAGCC   2280
```

```
CAGATAAAGT AGAATATTTT GAATTCAGCT TTCTAAGAAA GACTCAGACT TTCTTTAAAA    2340

CAGACTTTCG TCATTCTTGT GCAGAGATAT GCTTTGCAGG CCCAGGAGAT GTAAGACTTC    2400

TGTTTTCTTG CTGACCTTCA TCTGTGGAAC ACAAAGGCTG ATAAACTCTT GGCCTCTAAT    2460

CTTTACTGGA CCAGATGAAA TTCTTCTGTC CATTCTCATC TTTCAAAGCC TGTTATAGAT    2520

AGACAAGAAC TCAATCAATG TTAATTTTAA AAGGCTTCAA GTGGTTTGAC TTTTCTTCAA    2580

ATATTGACAA AACCTATTGG AGGTATATCA TTTTATTTGA GATTTATAGT TGTCTTTAGT    2640

CTACAGGACT TAGGATTACT CATTAGATTG TGCAACATAA AAAAGTAAAT AAAATGTAGA    2700

GTTTACACAT AAATTTTCCT GTAAACCGAT TTCTTGTAAA CATTTTCCCA ACTCCATACC    2760

CTCATGTAGG TACACAGTCT TATGTTGCTT AACCGTGGG                           2799
```

(2) INFORMATION FOR SEQ ID NO:43:

(i) SEQUENCE CHARACTERISTICS:
        (A) LENGTH: 704 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: intron
        (B) LOCATION: 1..110

(ix) FEATURE:
        (A) NAME/KEY: exon
        (B) LOCATION: 111..188

(ix) FEATURE:
        (A) NAME/KEY: intron
        (B) LOCATION: 189..704

(xi) SEQUENCE DESCRIPTION: SEQ ID NO:43:

```
TTCCTCTAGG AATATACTGG CATTTTGGCT GTCTACCCAG CTGTTGCTTC CATTTGCCTA     60

TTCCTTGAGT GTAAGGCAAT TAATAACTTA CACTTGTCTT TATGTTCCAG CCTGAAAGAA    120

TAGACCCAAG CGCATCACGA CAAGGATATG ATGTCCGCTC TGATGTCTGG AGTTTGGGGA    180

TCACATTGGT ATGTTTATGC TGATTCAACC TTGCCACAGT AGCGTAACAA TAAGAAATTT    240

AGAAGTGAAA GAAAACTTAA TCAGACTTCC CCGTTCGTTA AGAACTATAA TCACAGACAC    300

TATGGTTTTA AGTTGCTGAA AAAAAAAAG TATGTATTTA TTTACTTTAA AAATCAAATC     360

AGACTTGATT ATTTCCCTTG AAGTTATGTG AAGTGTCTAG AGCCCTTTAA TGTTTTAACT    420

GGATCTCTTG GCCACAGATA ATAGGAGTCA ACTATTATCT GCAACTGCAC TAAGAATGGG    480

AACAGGACAA GCCAGCTTAC CTGCAGTCAA TTCATTGATG AAGGCACATA GGCTTCTCCC    540

ATCTCAGGCA AGGTGTAGTA TGTCCAGTAA TACTGTATAT AGTGGGTATA TTAAGTATAC    600

GTATTTTAT ATGTGGAAAA TAGTTTCTAC TTGCAATATT CTATTCACTG AATAGTAAAA    660

TCACAAGTGA ATGAGCTGAA AGTAATTCAG TTTTTGAGGG ACAA                     704
```

(2) INFORMATION FOR SEQ ID NO:44:

(i) SEQUENCE CHARACTERISTICS:
        (A) LENGTH: 2892 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
   (A) NAME/KEY: intron
   (B) LOCATION: 1..1030

(ix) FEATURE:
   (A) NAME/KEY: exon
   (B) LOCATION: 1031..1179

(ix) FEATURE:
   (A) NAME/KEY: intron
   (B) LOCATION: 1180..2892

(xi) SEQUENCE DESCRIPTION: SEQ ID NO:44:

```
GGTCCTGTCC CCCAGGCTGG AGTGCAGTGG CGCAATCTCG GCTCACTGCA AACTCCGCCT      60
CCTGGGTTCA TGCCATTCCC CTGCCTCAGC CTCCTGAATA GCTGGGACTA CAGGCGCCTG     120
CCACCACGCC CGGCTAATTT TTTGTATTTT TAGTAGAGAT GGGGTTTCAC CGTGTTAGAC     180
AGGATGGTGT CCATCTCCTG ACCTCCTGAT CCACCCGCCT CGGCATCCCA AAGTGGTGGG     240
ATTACAGGCG TGACACTGTG CCCGGCCTAA TTGGTAGGTT TTCATTATTT TTCAGAACAG     300
AAAGGGAGAT AGATGAGAAT ACGATTCACT GGTTATTAGA GAATATTTTT TTTTTGGACC     360
CTTGATAGGA TTGGGACATA CGTAAGACTC TTCAGATCTC TTCTGGTGTG GCTTAGAGGT     420
ACTGTCCTGA GCCCTTTATT GGGGCTTCAG GATGCAGGGT TTGACCCTGA CTTGATTTCT     480
TCACTACTTG TAAAAATCNC GTTGTGGTTG AAATTGTAGT ATCTGCAGAA TAGCTGTAGA     540
GCAGGATTTG CACATTGTGT CCTCCAAGCT CAGATTAGGC TTTTGTTTGT TGGATGTTCT     600
TTTGCCTTAA AAAGGAGTCT AACCACGATT ATGGACCAAG GCCTTCCTCT AAGATGGCTA     660
CAAATTGTGC GTATTCTATA GTAAAATAGT TCTAAAACCA GTCTTCCAGA CTTTCTTATA     720
AAGAAGTCAG AACCACAGGC TGCCCTGGAG CATGCATTGT AGGGACATTG TCTAGGCTTA     780
AGTTTTGTGT TCCCATGTAT TCCAAGTCCT TGAATTTGGT TGATTCAGAA TTCTCTATAT     840
TATTTTGATT TCTAAATATA ACTTCTACTT AGCCTTTATG ATTCTGAAGA TTCCTCCCCA     900
AGCTAACCTG TGTTTAATTC AAGGCTTTAC TAGAGTTTTG CTTGTAGTTT AGATTTTTTT     960
GTGGCCCTTC CAGTGGGGAG TAGTAAATGA TGCCTGGTGT ATTTTGCTCT TTCCTCTTTG    1020
TTCTCTTTAG TATGAGTTGG CCACAGGCCG ATTTCCTTAT CCAAAGTGGA ATAGTGTATT    1080
TGATCAACTA ACACAAGTCG TGAAAGGAGA TCCTCCGCAG CTGAGTAATT CTGAGGAAAG    1140
GGAATTCTCC CCGAGTTTCA TCAACTTTGT CAACTTGTGG TGAGTACCTG ATTTATGAAT    1200
GGTCGAACAC GCATGGCGAG AATAGTGAGA TTTACTTGGT CTTAGCAGCA TTGGTACTTT    1260
ACATGGAGGA AGGGACCCT TGGTCACATC ACCCTACTTT TCAAGCTGGG ACTCTGGATC    1320
ACTGTGGCTG TATGGAAGGT TACAGCTAGC TGGGAGAGGC ATCACCTTCT TATTCTGCTA    1380
CTCAGGTATT GGTGAAAAAC AGCCATGAGT GGTGGAGAGG CTGCTGTCTC CAGACTTCCA    1440
GTACCTGGTA CAAGAAATAC CAGGTTAAAC TTCTAGGTGA GACTGATCAT CTTACTCTAA    1500
TGTGGTTCTC ACAATGCAGT TGCACCAAAA TCACCTGGAA GCATTTACTG AATCAAGAGC    1560
TTGCCAGATC AGACTTTCAG GGTTGGATCT CTGTTCTGAC ATAACATAGA AAACAGTTGG    1620
TTATATGTAG TAGGGTCACA TCCACACGCA AAGTGTAGTT GGTAGAACTG TATATCTTTG    1680
CTCTCTGAAA CCTTACTCCA AGGAAGATGT GAACCCCACA CCTGTTGTTG TTTGTCTACC    1740
TTTTTAATAG TTTGTTGTGT GTTTGTGTAT ATGTAGCACC TAAGAATAAA CATATGCAGA    1800
```

```
TATGGCAGTA ATATAATCAT GCTTTATACT GTTTTAGGCT CTTTTAAATA AAATCTTTTT      1860

GTGTTATCAT TTGGATATTT TTGACATTTA TTTTGTTTAT CCAACATGAT TTAAATATAA      1920

GACAGACCAT GAACAAAAAG CCTCAGAGCA TTTTGTGTAT CTTCTGTTTA TTCCTGAAAA      1980

TACCTTTTGG TTTCTCATAA TTTTTTCCTG CTAAGAATGC GGTTTCTCCT CATTTTAGGT      2040

CTTATAGACT TAAATCAGGG TCTAACATTG CCCTCCTTTG TATGAAAAAT TTAAAAATAT      2100

TTGTTTGACT ATAGTTTTTA AGTCTCTTTC ATCTTCTGTA ACCAAATTCT ACTTTTGTGT      2160

TGGTTTTTCA GAGGGGAGAG GAATACTTCA AGATTTTCTA GGTAGAAGAA GGACATAAGG      2220

ATGACTCAAA TTGGCTGCTT CCTCCTTTTA AAAACAATC AATTCTGTAC TAATTTGCAC       2280

ACAGTATGGA TAGTTTATAT AATTGCATAA ATGTGATCAT TTTATGTATT TCATTTTTTA      2340

TGACATATTT GCTTAAAATG ATCTGTGTAA GTCATAGGGT ATAATATCTA AAATGATCAC      2400

CTGTGAACCT TCCATCAGGG TTTCTTTTTA ACTCCTTGAT CTCTTTATTG GTTTTGTTCT      2460

GTATGTGTTG GTACTTGTAC ATGTTTAATT TCTGTTTCCC TTGATGCCAT AATAGAGTGA      2520

CAGTTTTAGA CATTGGAGTC CCATTGTTTT CCCTGAGTAG GTTCATAGTT CCATGTCATT      2580

GCAAATCATT AAGGTCTACA TTGAAGTGTA CTTATGTTCA TAATATGCTC ATATTAGCTC      2640

TCCACATTTG TCCATTCTTT CTGCCACTCT TTGTCTTGGA CATTGCCTGT AATCTCTAAC      2700

CTGGATCATT CAGATTTCTC ATAATCCAAT ATTGATTTTC TTATAATCCA ATATTGTCTT      2760

GTTCCAAATT ATTCCCCTTT TTATTAGAGT TGTATTTTTT ATGATGTATA TCTGATCATG      2820

TTACTTCTCT ATCTAAAGTA TGCATTCTTA GCAGGGTGAT ATTGACCCTA AGGAGGCAAA      2880

AATTGATTTT GG                                                          2892

(2) INFORMATION FOR SEQ ID NO:45:

(i) SEQUENCE CHARACTERISTICS:
        (A) LENGTH: 628 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: intron
        (B) LOCATION: 1..381

(ix) FEATURE:
        (A) NAME/KEY: exon
        (B) LOCATION: 382..427

(ix) FEATURE:
        (A) NAME/KEY: intron
        (B) LOCATION: 428..628

(xi) SEQUENCE DESCRIPTION: SEQ ID NO:45:

CATAAATATC TGTCTACTTA TTTATTTACA TTTAGAAAAG CATATATGTA CACAAATAAT        60

TTTATACTTA TAAAAACATT TATATATTTA ACTGTAGTAT TCTGTGTAGC TATGCCATAA       120

TTTAGTCAAT TTTCAAGAAT TAATATTTTT TCTAATTTTA AACTAATCAT CCTACACTGA       180

CTATCCTAGA GATAAATCTT CAGATTATAG ACTCACAATT TTTTGTATGT GCTTTTACTG       240

TGTTTAGCAG GCTGTCTGCG TTGTTACTTT GGATCTGAAG GAAAGAACTA TTTCATTATT       300

TGTAATATTT CATCTGTGAA AAGAAAAATA CTTAGGCAAA TGAATCTACA TTTTAATAAT       360
```

| | |
|---|---:|
| GTTATTTTTA TGTTATTTTA GCCTTACGAA GGATGAATCC AAAAGGCCAA AGTATAAAGA | 420 |
| GCTTCTGGTG AGTGTGGGAC TGTGGGGATT GTAGGTACAT CCTAACCCCG GAACTCTCTT | 480 |
| AACATGCTGG TTCACTAAGC AAGCAGTGGG CCTCTCTGTC ATAAACAAAC ATCTCAAATT | 540 |
| TATTGAGTGT TTTTTGTTAA TGTTTTTACA CAAAGATTTG GAAAGAGAAA ATTTGCAGTT | 600 |
| ATANTTTTTC TACTAATACT AGCTAAAT | 628 |

(2) INFORMATION FOR SEQ ID NO:46:

(i) SEQUENCE CHARACTERISTICS:
        (A) LENGTH: 5224 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: intron
        (B) LOCATION: 1..1072

(ix) FEATURE:
        (A) NAME/KEY: exon
        (B) LOCATION: 1073..3553

(xi) SEQUENCE DESCRIPTION: SEQ ID NO:46:

| | |
|---|---:|
| CTAGCTAAAT TCTCATGGAA AATTTTGGTC TTAACATGTT ATAAAAATTA CCCCCAAAGA | 60 |
| ATTCTGACTT TAAGAAGCCA TTTTCCACTG CATAGTCTAT TTATATGGGA TGCAGCCATA | 120 |
| AGAAAAAAAT TAGTGAAAAG TTTGTGTTTA TTCTGCCTTT ATAAAATTCA TGCAAATTTA | 180 |
| CATCATATAG CCTATTCCCA TTTCTTTGAA AGTTCTCATT CATCCCATGG AACTTGGGTG | 240 |
| TTTTAAGCAG TCTACTGGGT ATGGCATTGG TGGGGCAGGG AGAAAGTGTT GTGATCTAAT | 300 |
| AATGTGGGAA TATTTTAAGA AAAGATCCAT TTGTTTGTCA CATTTAACTA CTAGCTCTTC | 360 |
| AAGGATGTTG TGACAAACTT ATATCGCAGT CCACCAATGA CTGTAAAAAT ATCTAGTCAA | 420 |
| CATACTTAGT CTGTAAAAGA AAACTGTTGC TAGAGATGGA GTTTTAAAAG GTGGGTTAGT | 480 |
| GAAGCAGATA CTGGGACCCT GGCTCTGGAG AGTACAGGGA AGAAGCTCCT GGGGCAAATT | 540 |
| TCTCTTGGGC CTCTTTTGGT CAAAAGAATT ACAGCCTTTT TGTTAAAAGG TCAAAAGAAG | 600 |
| AGGTCAAAAG GATTGCGACC TTTTTGTAAA AAGGTCCTCC TGTTGTATAT AGGAGAAATG | 660 |
| GAGGTTGAGA TTTATATTGG TGTCCCAAGA GGAATAGTGA CTGGCATTTG CGTCATTCTT | 720 |
| CTTAGCTCTT AGATGGTGTG GTGGAGGCTC CAGCTATGTT TTGTGCTGAG TGACAACTTG | 780 |
| GCTGTCTTCC TCAACAAACA CTCCCTGGTA TACAGATGAG TTTCCAGACC TCACTGCCAA | 840 |
| GGTGGCACCT TCAGATCATT ACCACGTATC CTCTCTCTAG GCATGCCCAT GCCCATTAGC | 900 |
| ATATCTGCAT GGAATAAAGG CTGTACTCGC CTCTCTGAAC TTGTAGTGTT GCGGTATTTC | 960 |
| ATAGCTATGT GTGGTTGGGA GCCTGGAGTT CTATGTTCTA TAGAAATTGG AAAATGTTCA | 1020 |
| GTTTGGGCTG TCATACAAAC TTTTGACTTT TTTGTTTTCA ATTTTCTTGC AGAAACATCC | 1080 |
| CTTTATTTTG ATGTATGAAG AACGTGCCGT TGAGGTCGCA TGCTATGTTT GTAAAATCCT | 1140 |
| GGATCAAATG CCAGCTACTC CCAGCTCTCC CATGTATGTC GATTGATATC GCTGCTACAT | 1200 |
| CAGACTCTAG AAAAAAGGGC TGAGAGGAAG CAAGACGTAA AGAATTTTCA TCCCGTATCA | 1260 |
| CAGTGTTTTT ATTGCTCGCC CAGACACCAT GTGCAATAAG ATTGGTGTTC GTTTCCATCA | 1320 |
| TGTCTGTATA CTCCTGTCAC CTAGAACGTG CATCCTTGTA ATACCTGATT GATCACACAG | 1380 |

-continued

| | | | | | |
|---|---|---|---|---|---|
|TGTTAGTGCT|GGTCAGAGAG|ACCTCATCCT|GCTCTTTTGT|GATGAACATA|TTCATGAAAT|1440|
|GTGGAAGTCA|GTACGATCAA|GTTGTTGACT|GTGATTAGAT|CACATCTTAA|ATTCATTTCT|1500|
|AGACTCAAAA|CCTGGAGATG|CAGCTACTGG|AATGGTGTTT|TGTCAGACTT|CCAAATCCTG|1560|
|GAAGGACACA|GTGATGAATG|TACTATATCT|GAACATAGAA|ACTCGGGCTT|GAGTGAGAAG|1620|
|AGCTTGCACA|GCCAACGAGA|CACATTGCCT|TCTGGAGCTG|GGAGACAAAG|GAGGAATTTA|1680|
|CTTTCTTCAC|CAAGTGCAAT|AGATTACTGA|TGTGATATTC|TGTTGCTTTA|CAGTTACAGT|1740|
|TGATGTTTGG|GGATCGATGT|GCTCAGCCAA|ATTTCCTGTT|TGAAATATCA|TGTTAAATTA|1800|
|GAATGAATTT|ATCTTTACCA|AAAACCATGT|TGCGTTCAAA|GAGGTGAACA|TTAAAATATA|1860|
|GAGACAGGAC|AGAATGTGTT|CTTTTCTCCT|CTACCAGTCC|TATTTTTCAA|TGGGAAGACT|1920|
|CAGGAGTCTG|CCACTTGTCA|AGAAGGTGC|TGATCCTAAG|AATTTTTCAT|TCTCAGAATT|1980|
|CGGTGTGCTG|CCAACTTGAT|GTTCCACCTG|CCACAAACCA|CCAGGACTGA|AGAAGAAAA|2040|
|CAGTACAGAA|GGCAAAGTTT|ACAGATGTTT|TTAATTCTAG|TATTTTATCT|GGAACAACTT|2100|
|GTAGCAGCTA|TATATTTCCC|CTTGGTCCCA|AGCCTGATCA|TTTAGCCATC|ATAACTCACT|2160|
|AACAGGGAGA|AGTAGCTAGT|AGCAATGTGC|CTTGATTGAT|TAGATAAAGA|TTTCTAGTAG|2220|
|GCAGCAAAAG|ACCAAATCTC|AGTTGTTTGC|TTCTTGCCAT|CACTGGTCCA|GGTCTTCAGT|2280|
|TTCCGAATCT|CTTTCCCTTC|CCCTGTGGTC|TATTGTCGCT|ATGTGACTTG|CGCTTAATCC|2340|
|AATATTTTGC|CTTTTTTCTA|TATCAAAAA|CCTTTACAGT|TAGCAGGGAT|GTTCCTTACC|2400|
|GAGGATTTTT|AACCCCCAAT|CTCTCATAAT|CGCTAGTGTT|TAAAAGGCTA|AGAATAGTGG|2460|
|GGCCCAACCG|ATGTGGTAGG|TGATAAAGAG|GCATCTTTTC|TAGAGACACA|TTGGACCAGA|2520|
|TGAGGATCCG|AAACGGCAGC|CTTTACGTTC|ATCACCTGCT|AGAACCTCTC|GTAGTCCATC|2580|
|ACCATTTCTT|GGCATTGGAA|TTCTACTGGA|AAAAAATACA|AAAAGCAAAA|CAAAACCCTC|2640|
|AGCACTGTTA|CAAGAGGCCA|TTTAAGTATC|TTGTGCTTCT|TCACTTACCC|ATTAGCCAGG|2700|
|TTCTCATTAG|GTTTTGCTTG|GGCCTCCCTG|GCACTGAACC|TTAGGCTTTG|TATGACAGTG|2760|
|AAGCAGCACT|GTGAGTGGTT|CAAGCACACT|GGAATATAAA|ACAGTCATGG|CCTGAGATGC|2820|
|AGGTGATGCC|ATTACAGAAC|CAAATCGTGG|CACGTATTGC|TGTGTCTCCT|CTCAGAGTGA|2880|
|CAGTCATAAA|TACTGTCAAA|CAATAAAGGG|AGAATGGTGC|TGTTTAAAGT|CACATCCCTG|2940|
|TAAATTGCAG|AATTCAAAAG|TGATTATCTC|TTTGATCTAC|TTGCCTCATT|TCCCTATCTT|3000|
|CTCCCCCACG|GTATCCTAAA|CTTTAGACTT|CCCACTGTTC|TGAAAGGAGA|CATTGCTCTA|3060|
|TGTCTGCCTT|CGACCACAGC|AAGCCATCAT|CCTCCATTGC|TCCCGGGGAC|TCAAGAGGAA|3120|
|TCTGTTTCTC|TGCTGTCAAC|TTCCCATCTG|GCTCAGCATA|GGGTCACTTT|GCCATTATGC|3180|
|AAATGGAGAT|AAAAGCAATT|CTGGCTGTCC|AGGAGCTAAT|CTGACCGTTC|TATTGTGTGG|3240|
|ATGACCACAT|AAGAAGGCAA|TTTTAGTGTA|TTAATCATAG|ATTATTATAA|ACTATAAACT|3300|
|TAAGGGCAAG|GAGTTTATTA|CAATGTATCT|TTATTAAAAC|AAAAGGGTGT|ATAGTGTTCA|3360|
|CAAACTGTGA|AAATAGTGTA|AGAACTGTAC|ATTGTGAGCT|CTGGTTATTT|TTCTCTTGTA|3420|
|CCATAGAAAA|ATGTATAAAA|ATTATCAAAA|AGCTAATGTG|CAGGGATATT|GCCTTATTTG|3480|
|TCTGTAAAAA|ATGGAGCTCA|GTAACATAAC|TGCTTCTTGG|AGCTTTGGAA|TATTTTATCC|3540|
|TGTATTCTTG|TTTGAATTCC|TCCTCTATTT|AAGATATATA|CATGGAATCG|AAGTGTTTAT|3600|
|GTAATAGTTC|TATCCTTTTG|CCTGCAGGTC|AGTTGTAATA|AATCTAGGAT|GTGATGATGA|3660|
|CTTTGTAATT|TGATTTTCTG|AAATCAGACC|CTGAGAGGGG|AAAATCTTAA|AGTAAATTAC|3720|
|ATTAAATTAT|CTGTGCATTT|CACACCAGGG|AAAATGACCT|CCTTTTGGAA|GTGTTTTATG|3780|

```
GCTGCTTTCT TTTTCTTCTT CCTTCCCATG GCTACCCTTT TTGCTTATCC TTCTTGAAAC      3840

CACAGATGTA TCTGTTAAGC ATAGCTTTGC TTGAACAGGT GTCACAGTCT CTTGAGTTTC      3900

TTTGTTTGTT GTCCTGACCT GCCCCAGCAT TCTTAATGCT AAAGGAAGTG GGTACAGTTC      3960

TTCAACCTGT GTCATGGTGG AGAGGTACAA CTTATAAGTC TATCTGGGCC CCGTGTATGG      4020

TTTCCAGCCA TGCTCTCCGC TCTTGGTGCT TCAGCTGCCA GGTGAGCATT AGATGTCAGG      4080

TTAGATACTG GGTTGGAATC ACTCACTGTT ACCTTAGAAG GGTAGGGAGG ATTGTGGGTA      4140

GAAGACGTCT GGAGGTCAGA CATGGGAGGT TTATGGATGA GAGGACAATG GAAGTGAACA      4200

AAAAGCCATG GGAGCCTGAA AACTGTTGGA GAAAAGCACT TTGCGGCTCC AGCACTGAAT      4260

GTATCTGCTG TACTCTACCT CCTACCAGTG ATTGATCAGA TAACAGATTC ATTGATATTA      4320

TGGTGATTCA GCACCTTGCC CTTGTGCCTG CTCCTAACTG TACCTGAGAT ACTATTACAC      4380

AGCCAGATGT GGTATCAAAC ATTCCCCTGA GAGGGGTGTG AAAGCAGGAA TTCTGGCCTC      4440

TCCAGCTAAC CTCAGCTGCT AAGGGAAAGG GTACCCATTG GGTTTCAATA CTGGCATGAG      4500

AGATAGACTA CACACTCCAT GTTTCATAGG ACACTGCCTT GTATTTGTTC ATCTCATTTG      4560

ATTCCAAATG CATCCCACTA AAATCAAGTG GCTGTATCCC CTTTTAGATA CAAGAAAACC      4620

AAGGTCCGAA GAGTGAAGTT CTGGCTCAAA TAACAGTAGG GAGCAGAGCT GAGATTCAAA      4680

TTCAAGGCCG TAACACGTAC CCTAAGAAGT TACATTAATT TTAAAACACT GCTATTAAAG      4740

AAGTGTTGTG GAGTTGAGAA GTGGAAGAAT GAATATAGTT GAGGATACTC TGTTCATAAA      4800

CCTGACCAGG GCCTGCTTTG TTGTTTTGGA AATGAGTTGA AGGCAGAGGT TCTGGGGGCC      4860

ACAGTGGGGC TTAACATACA AAGCGATCCA TACAAAGGCA ACTGTGTAAT TACCTTAGAA      4920

TTAACTAGAG GAACTCTAGG TTGTAATTCT TCAGTGCAAA CACCTGAGAA TTCAGTGTCA      4980

TGGACTGAAC GTCTCCATTA GCATGATAAT GTGGCAATCA CTGAGAATGA GTAAAGTGCC      5040

CTTTCATTTA TTTTATTTAT TTTTTATTTT TTGAGACAGT TTTGCTCTTG TTGCCCAGGC      5100

TGGAATGCAA TGATGTGATC TTGGCTCTGC AACCTCTGCC TCCGGAGTTC AAGCAATTCT      5160

GCCTCAGCCT CCCGAGTAGC TGGGATTGCA GGTGCACACN GCTAAGNATA GTGGGGCCAG      5220

CGAT                                                                  5224

(2) INFORMATION FOR SEQ ID NO:47:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:47:

GCTGTCTGCT TCACAGGTCG C                                                21

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:48:
```

CGGGGAGGGA GAGAGGGAGA                                                    20

(2) INFORMATION FOR SEQ ID NO:49:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Primer."

(xi) SEQUENCE DESCRIPTION: SEQ ID NO:49:

GTTTTCCCAG TCACGACGCG GTTCTGCAGC TCAGCATCT                                39

(2) INFORMATION FOR SEQ ID NO:50:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Primer."

(xi) SEQUENCE DESCRIPTION: SEQ ID NO:50:

AGGAAACAGC TATGACCATC GGCTGCCGTG GCTTCCTCA                                39

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Primer."

(xi) SEQUENCE DESCRIPTION: SEQ ID NO:51:

TTGAGAAATT CCTCATTGCC                                                    20

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Primer."

(xi) SEQUENCE DESCRIPTION: SEQ ID NO:52:

CAATATTCCC AGAGAGTTTA                                                    20

(2) INFORMATION FOR SEQ ID NO:53:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "Primer."

(xi) SEQUENCE DESCRIPTION: SEQ ID NO:53:

```
GTTTTCCCAG TCACGACGTT GCCTTTTGGT GTGACTTT                                    38

(2) INFORMATION FOR SEQ ID NO:54:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer."

(xi) SEQUENCE DESCRIPTION: SEQ ID NO:54:

AGGAAACAGC TATGACCATA CTGACATCTC ATAATTGGA                                   39

(2) INFORMATION FOR SEQ ID NO:55:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer."

(xi) SEQUENCE DESCRIPTION: SEQ ID NO:55:

CCTGGAGGTC AGACTATTTT                                                        20

(2) INFORMATION FOR SEQ ID NO:56:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer."

(xi) SEQUENCE DESCRIPTION: SEQ ID NO:56:

AAAGGAGTTG GAGAAACAAT                                                        20

(2) INFORMATION FOR SEQ ID NO:57:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer."

(xi) SEQUENCE DESCRIPTION: SEQ ID NO:57:

GTTTTCCCAG TCACGACGAA CATTTTTCCC ACACATTA                                    38

(2) INFORMATION FOR SEQ ID NO:58:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer."

(xi) SEQUENCE DESCRIPTION: SEQ ID NO:58:
```

AGGAAACAGC TATGACCATA GGAACACAAC AACAGTGGT    39

(2) INFORMATION FOR SEQ ID NO:59:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:59:

CTTGTGAAGT ATAAGGAAAG ATG    23

(2) INFORMATION FOR SEQ ID NO:60:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:60:

TGGTTAAACA CTAAGATACT GAG    23

(2) INFORMATION FOR SEQ ID NO:61:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:61:

GTTTTCCCAG TCACGACGTC GTAACGGTTT TTCTCTACCA    40

(2) INFORMATION FOR SEQ ID NO:62:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:62:

AGGAAACAGC TATGACCATA AGAATAGAAT CGAATCCTGC C    41

(2) INFORMATION FOR SEQ ID NO:63:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:63:

TGGGGAAAAT TGGCTTTAAC TAC                                              23

(2) INFORMATION FOR SEQ ID NO:64:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:64:

CGAGACCATT ATGACCTATT GTG                                              23

(2) INFORMATION FOR SEQ ID NO:65:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:65:

GTTTTCCCAG TCACGACGCT AGTTTGACAT TTGAAATAAG CA                         42

(2) INFORMATION FOR SEQ ID NO:66:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:66:

AGGAAACAGC TATGACCATC AGAAGTGACT TTGTCTCTGG T                          41

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:67:

GCTTAAAATG TATGCAGAGG                                                  20

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:68:

CCAGAGAGAA AAATAGCAGT                                                    20

(2) INFORMATION FOR SEQ ID NO:69:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:69:

GTTTTCCCAG TCACGACGCT TGTGATAAAC TGTTGTGC                                 38

(2) INFORMATION FOR SEQ ID NO:70:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:70:

AGGAAACAGC TATGACCATC ACTGTAATTT TCAATAACC                                39

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:71:

TCTGAATTTA AGGACTTGAC                                                    20

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:72:

AGCAAAGTTT CATGGAGAGG                                                    20

(2) INFORMATION FOR SEQ ID NO:73:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:73:

GTTTTCCCAG TCACGACGCT TAAAGTGAAG CCTTATGT    38

(2) INFORMATION FOR SEQ ID NO:74:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:74:

AGGAAACAGC TATGACCATG GTAAAACCGT ATGACTAATG    40

(2) INFORMATION FOR SEQ ID NO:75:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:75:

AGGAATATAC TGGCATTTTG G    21

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:76:

AGCAACTTAA AACCATAGTG    20

(2) INFORMATION FOR SEQ ID NO:77:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:77:

GTTTTCCCAG TCACGACGGT TGCTTCCATT TGCCTATT    38

(2) INFORMATION FOR SEQ ID NO:78:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:78:

AGGAAACAGC TATGACCATC GAACGGGGAA GTCTGATTA          39

(2) INFORMATION FOR SEQ ID NO:79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:79:

ACTTAGCCTT TATGATTCTG                              20

(2) INFORMATION FOR SEQ ID NO:80:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:80:

GCTTGAAAAG TAGGGTGATG                              20

(2) INFORMATION FOR SEQ ID NO:81:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:81:

GTTTTCCCAG TCACGACGTT TTGCTTGTAG TTTAGATTT         39

(2) INFORMATION FOR SEQ ID NO:82:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:82:

AGGAAACAGC TATGACCATT CCTCCATGTA AAGTACCAA         39

(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:83:

GGCTGTCTGC GTTGTTACTT                                           20

(2) INFORMATION FOR SEQ ID NO:84:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:84:

TAACAAAAAA CACTCAATAA A                                         21

(2) INFORMATION FOR SEQ ID NO:85:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:85:

GTTTTCCCAG TCACGACGTG TGAAAAGAAA AATACTTAGG                      40

(2) INFORMATION FOR SEQ ID NO:86:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:86:

AGGAAACAGC TATGACCATG TTTGTTTATG ACAGAGAGG                       39

(2) INFORMATION FOR SEQ ID NO:87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:87:

TGGGAGCCTG GAGTTCTATG                                           20

(2) INFORMATION FOR SEQ ID NO:88:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer."

(xi) SEQUENCE DESCRIPTION: SEQ ID NO:88:

```
GGGAAGGGAA AGAGATTCGG                                          20

(2) INFORMATION FOR SEQ ID NO:89:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer."

(xi) SEQUENCE DESCRIPTION: SEQ ID NO:89:

GTTTTCCCAG TCACGACGTT GGAAAATGTT CAGTTTGG                      38

(2) INFORMATION FOR SEQ ID NO:90:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer."

(xi) SEQUENCE DESCRIPTION: SEQ ID NO:90:

AGGAAACAGC TATGACCATC GTTCTAGGTG ACAGGAGTA                     39

(2) INFORMATION FOR SEQ ID NO:91:

(i) SEQUENCE CHARACTERISTICS:
         (A) LENGTH: 3587 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (ix) FEATURE:
         (A) NAME/KEY: CDS
         (B) LOCATION: 21..1217

(xi) SEQUENCE DESCRIPTION: SEQ ID NO:91:

TGGGCTCTTC ACTCCCAACA ATG GCG GCT CCG AGC CCG AGC GGC GGC GGC      50
                      Met Ala Ala Pro Ser Pro Ser Gly Gly Gly
                       1               5                  10

GGC TCC GGG GGC GGC AGC GGC AGC GGC ACC CCC GGC CCC GTA GGG TCC   98
Gly Ser Gly Gly Gly Ser Gly Ser Gly Thr Pro Gly Pro Val Gly Ser
             15                  20                  25

CCG GCG CCA GGC CAC CCG GCC GTC AGC AGC ATG CAG GGT AAA CGC AAA  146
Pro Ala Pro Gly His Pro Ala Val Ser Ser Met Gln Gly Lys Arg Lys
         30                  35                  40

GCA CTG AAG TTG AAT TTT GCA AAT CCA CCT TTC AAA TCT ACA GCA AGG  194
Ala Leu Lys Leu Asn Phe Ala Asn Pro Pro Phe Lys Ser Thr Ala Arg
     45                  50                  55

TTT ACT CTG AAT CCC AAT CCT ACA GGA GTT CAA AAC CCA CAC ATA GAG  242
Phe Thr Leu Asn Pro Asn Pro Thr Gly Val Gln Asn Pro His Ile Glu
 60                  65                  70

AGA CTG AGA ACA CAC AGC ATT GAG TCA TCA GGA AAA CTG AAG ATC TCC  290
Arg Leu Arg Thr His Ser Ile Glu Ser Ser Gly Lys Leu Lys Ile Ser
 75                  80                  85                  90
```

```
CCT GAA CAA CAC TGG GAT TTC ACT GCA GAG GAC TTG AAA GAC CTT GGA      338
Pro Glu Gln His Trp Asp Phe Thr Ala Glu Asp Leu Lys Asp Leu Gly
             95                 100                 105

GAA ATT GGA CGA GGA GCT TAT GGT TCT GTC AAC AAA ATG GTC CAC AAA      386
Glu Ile Gly Arg Gly Ala Tyr Gly Ser Val Asn Lys Met Val His Lys
        110                 115                 120

CCA AGT GGG CAA ATA ATG GCA GTT AAA AGA ATT CGG TCA ACA GTG GAT      434
Pro Ser Gly Gln Ile Met Ala Val Lys Arg Ile Arg Ser Thr Val Asp
        125                 130                 135

GAA AAA GAA CAA AAA CAA CTT CTT ATG GAT TTG GAT GTA GTA ATG CGG      482
Glu Lys Glu Gln Lys Gln Leu Leu Met Asp Leu Asp Val Val Met Arg
        140                 145                 150

AGT AGT GAT TGC CCA TAC ATT GTT CAG TTT TAT GGT GCA CTC TTC AGA      530
Ser Ser Asp Cys Pro Tyr Ile Val Gln Phe Tyr Gly Ala Leu Phe Arg
155                 160                 165                 170

GAG GGT GAC TGT TGG ATC TGT ATG GAA CTC ATG TCT ACC TCG TTT GAT      578
Glu Gly Asp Cys Trp Ile Cys Met Glu Leu Met Ser Thr Ser Phe Asp
                175                 180                 185

AAG TTT TAC AAA TAT GTA TAT AGT GTA TTA GAT GAT GTT ATT CCA GAA      626
Lys Phe Tyr Lys Tyr Val Tyr Ser Val Leu Asp Asp Val Ile Pro Glu
            190                 195                 200

GAA ATT TTA GGC AAA ATC ACT TTA GCA ACT GTG AAA GCA CTA AAC CAC      674
Glu Ile Leu Gly Lys Ile Thr Leu Ala Thr Val Lys Ala Leu Asn His
        205                 210                 215

TTA AAA GAA AAC TTG AAA ATT ATT CAC AGA GAT ATC AAA CCT TCC AAT      722
Leu Lys Glu Asn Leu Lys Ile Ile His Arg Asp Ile Lys Pro Ser Asn
        220                 225                 230

ATT CTT CTG GAC AGA AGT GGA AAT ATT AAG CTC TGT GAC TTC GGC ATC      770
Ile Leu Leu Asp Arg Ser Gly Asn Ile Lys Leu Cys Asp Phe Gly Ile
235                 240                 245                 250

AGT GGA CAG CTT GTG GAC TCT ATT GCC AAG ACA AGA GAT GCT GGC TGT      818
Ser Gly Gln Leu Val Asp Ser Ile Ala Lys Thr Arg Asp Ala Gly Cys
                255                 260                 265

AGG CCA TAC ATG GCA CCT GAA AGA ATA GAC CCA AGC GCA TCA CGA CAA      866
Arg Pro Tyr Met Ala Pro Glu Arg Ile Asp Pro Ser Ala Ser Arg Gln
            270                 275                 280

GGA TAT GAT GTC CGC TCT GAT GTC TGG AGT TTG GGG ATC ACA TTG TAT      914
Gly Tyr Asp Val Arg Ser Asp Val Trp Ser Leu Gly Ile Thr Leu Tyr
        285                 290                 295

GAG TTG GCC ACA GGC CGA TTT CCT TAT CCA AAG TGG AAT AGT GTA TTT      962
Glu Leu Ala Thr Gly Arg Phe Pro Tyr Pro Lys Trp Asn Ser Val Phe
300                 305                 310

GAT CAA CTA ACA CAA GTC GTG AAA GGA GAT CCT CCG CAG CTG AGT AAT      1010
Asp Gln Leu Thr Gln Val Val Lys Gly Asp Pro Pro Gln Leu Ser Asn
315                 320                 325                 330

TCT GAG GAA AGG GAA TTC TCC CCG AGT TTC ATC AAC TTT GTC AAC TTG      1058
Ser Glu Glu Arg Glu Phe Ser Pro Ser Phe Ile Asn Phe Val Asn Leu
                335                 340                 345

TGC CTT ACG AAG GAT GAA TCC AAA AGG CCA AAG TAT AAA GAG CTT CTG      1106
Cys Leu Thr Lys Asp Glu Ser Lys Arg Pro Lys Tyr Lys Glu Leu Leu
            350                 355                 360

AAA CAT CCC TTT ATT TTG ATG TAT GAA GAA CGT GCC GTT GAG GTC GCA      1154
Lys His Pro Phe Ile Leu Met Tyr Glu Glu Arg Ala Val Glu Val Ala
        365                 370                 375

TGC TAT GTT TGT AAA ATC CTG GAT CAA ATG CCA GCT ACT CCC AGC TCT      1202
Cys Tyr Val Cys Lys Ile Leu Asp Gln Met Pro Ala Thr Pro Ser Ser
380                 385                 390

CCC ATG TAT GTC GAT TGATATCGCT GCTACATCAG ACTCTAGAAA AAAGGGCTGA      1257
Pro Met Tyr Val Asp
395
```

```
GAGGAAGCAA GACGTAAAGA ATTTTCATCC CGTATCACAG TGTTTTTATT GCTCGCCCAG      1317

ACACCATGTG CAATAAGATT GGTGTTCGTT TCCATCATGT CTGTATACTC CTGTCACCTA      1377

GAACGTGCAT CCTTGTAATA CCTGATTGAT CACACAGTGT TAGTGCTGGT CAGAGAGACC      1437

TCATCCTGCT CTTTTGTGAT GAACATATTC ATGAAATGTG GAAGTCAGTA CGATCAAGTT      1497

GTTGACTGTG ATTAGATCAC ATCTTAAATT CATTTCTAGA CTCAAAACCT GGAGATGCAG      1557

CTACTGGAAT GGTGTTTTGT CAGACTTCCA AATCCTGGAA GGACACAGTG ATGAATGTAC      1617

TATATCTGAA CATAGAAACT CGGGCTTGAG TGAGAAGAGC TTGCACAGCC AACGAGACAC      1677

ATTGCCTTCT GGAGCTGGGA GACAAAGGAG GAATTTACTT TCTTCACCAA GTGCAATAGA      1737

TTACTGATGT GATATTCTGT TGCTTTACAG TTACAGTTGA TGTTTGGGGA TCGATGTGCT      1797

CAGCCAAATT TCCTGTTTGA AATATCATGT TAAATTAGAA TGAATTTATC TTTACCAAAA      1857

ACCATGTTGC GTTCAAAGAG GTGAACATTA AAATATAGAG ACAGGACAGA ATGTGTTCTT      1917

TTCTCCTCTA CCAGTCCTAT TTTTCAATGG GAAGACTCAG GAGTCTGCCA CTTGTCAAAG      1977

AAGGTGCTGA TCCTAAGAAT TTTTCATTCT CAGAATTCGG TGTGCTGCCA ACTTGATGTT      2037

CCACCTGCCA CAAACCACCA GGACTGAAAG AAGAAAACAG TACAGAAGGC AAAGTTTACA      2097

GATGTTTTTA ATTCTAGTAT TTTATCTGGA ACAACTTGTA GCAGCTATAT ATTTCCCCTT      2157

GGTCCCAAGC CTGATACTTT AGCCATCATA ACTCACTAAC AGGGAGAAGT AGCTAGTAGC      2217

AATGTGCCTT GATTGATTAG ATAAAGATTT CTAGTAGGCA GCAAAAGACC AAATCTCAGT      2277

TGTTTGCTTC TTGCCATCAC TGGTCCAGGT CTTCAGTTTC CGAATCTCTT TCCCTTCCCC      2337

TGTGGTCTAT TGTCGCTATG TGACTTGCGC TTAATCCAAT ATTTTGCCTT TTTTCTATAT      2397

CAAAAAACCT TTACAGTTAG CAGGGATGTT CCTTACCGAG GATTTTTAAC CCCCAATCTC      2457

TCATAATCGC TAGTGTTTAA AAGGCTAAGA ATAGTGGGGC CCAACCGATG TGGTAGGTGA      2517

TAAAGAGGCA TCTTTTCTAG AGACACATTG GACCAGATGA GGATCCGAAA CGGCAGCCTT      2577

TACGTTCATC ACCTGCTAGA ACCTCTCGTA GTCCATCACC ATTTCTTGGC ATTGGAATTC      2637

TACTGGAAAA AAATACAAAA AGCAAAACAA AACCCTCAGC ACTGTTACAA GAGGCCATTT      2697

AAGTATCTTG TGCTTCTTCA CTTACCCATT AGCCAGGTTC TCATTAGGTT TTGCTTGGGC      2757

CTCCCTGGCA CTGAACCTTA GGCTTTGTAT GACAGTGAAG CAGCACTGTG AGTGGTTCAA      2817

GCACACTGGA ATATAAAACA GTCATGGCCT GAGATGCAGG TGATGCCATT ACAGAACCAA      2877

ATCGTGGCAC GTATTGCTGT GTCTCCTCTC AGAGTGACAG TCATAAATAC TGTCAAACAA      2937

TAAAGGGAGA ATGGTGCTGT TTAAAGTCAC ATCCCTGTAA ATTGCAGAAT TCAAAAGTGA      2997

TTATCTCTTT GATCTACTTG CCTCATTTCC CTATCTTCTC CCCCACGGTA TCCTAAACTT      3057

TAGACTTCCC ACTGTTCTGA AAGGAGACAT TGCTCTATGT CTGCCTTCGA CCACAGCAAG      3117

CCATCATCCT CCATTGCTCC CGGGGACTCA AGAGGAATCT GTTTCTCTGC TGTCAACTTC      3177

CCATCTGGCT CAGCATAGGG TCACTTTGCC ATTATGCAAA TGGAGATAAA AGCAATTCTG      3237

GCTGTCCAGG AGCTAATCTG ACCGTTCTAT TGTGTGGATG ACCACATAAG AAGGCAATTT      3297

TAGTGTATTA ATCATAGATT ATTATAAACT ATAAACTTAA GGGCAAGGAG TTTATTACAA      3357

TGTATCTTTA TTAAAACAAA AGGGTGTATA GTGTTCACAA ACTGTGAAAA TAGTGTAAGA      3417

ACTGTACATT GTGAGCTCTG GTTATTTTTC TCTTGTACCA TAGAAAAATG TATAAAAATT      3477

ATCAAAAAGC TAATGTGCAG GGATATTGCC TTATTTGTCT GTAAAAAATG GAGCTCAGTA      3537

ACATAACTGC TTCTTGGAGC TTTGGAATAT TTTATCCTGT ATTCTTGTTT                 3587

(2) INFORMATION FOR SEQ ID NO:92:
```

(i) SEQUENCE CHARACTERISTICS:
    (A) LENGTH: 399 amino acids
    (B) TYPE: amino acid
    (D) TOPOLOGY: linear (ii) MOLECULE TYPE: protein (xi) SEQUENCE DESCRIPTION: SEQ ID NO:92:

```
Met Ala Ala Pro Ser Pro Ser Gly Gly Gly Ser Gly Gly Gly Ser
 1               5                  10                  15

Gly Ser Gly Thr Pro Gly Pro Val Gly Ser Pro Ala Pro Gly His Pro
            20                  25                  30

Ala Val Ser Ser Met Gln Gly Lys Arg Lys Ala Leu Lys Leu Asn Phe
         35                  40                  45

Ala Asn Pro Pro Phe Lys Ser Thr Ala Arg Phe Thr Leu Asn Pro Asn
     50                  55                  60

Pro Thr Gly Val Gln Asn Pro His Ile Glu Arg Leu Arg Thr His Ser
 65                  70                  75                  80

Ile Glu Ser Ser Gly Lys Leu Lys Ile Ser Pro Glu Gln His Trp Asp
                 85                  90                  95

Phe Thr Ala Glu Asp Leu Lys Asp Leu Gly Glu Ile Gly Arg Gly Ala
            100                 105                 110

Tyr Gly Ser Val Asn Lys Met Val His Lys Pro Ser Gly Gln Ile Met
        115                 120                 125

Ala Val Lys Arg Ile Arg Ser Thr Val Asp Glu Lys Glu Gln Lys Gln
    130                 135                 140

Leu Leu Met Asp Leu Asp Val Val Met Arg Ser Ser Asp Cys Pro Tyr
145                 150                 155                 160

Ile Val Gln Phe Tyr Gly Ala Leu Phe Arg Glu Gly Asp Cys Trp Ile
                165                 170                 175

Cys Met Glu Leu Met Ser Thr Ser Phe Asp Lys Phe Tyr Lys Tyr Val
            180                 185                 190

Tyr Ser Val Leu Asp Asp Val Ile Pro Glu Glu Ile Leu Gly Lys Ile
        195                 200                 205

Thr Leu Ala Thr Val Lys Ala Leu Asn His Leu Lys Glu Asn Leu Lys
    210                 215                 220

Ile Ile His Arg Asp Ile Lys Pro Ser Asn Ile Leu Leu Asp Arg Ser
225                 230                 235                 240

Gly Asn Ile Lys Leu Cys Asp Phe Gly Ile Ser Gly Gln Leu Val Asp
                245                 250                 255

Ser Ile Ala Lys Thr Arg Asp Ala Gly Cys Arg Pro Tyr Met Ala Pro
            260                 265                 270

Glu Arg Ile Asp Pro Ser Ala Ser Arg Gln Gly Tyr Asp Val Arg Ser
        275                 280                 285

Asp Val Trp Ser Leu Gly Ile Thr Leu Tyr Glu Leu Ala Thr Gly Arg
    290                 295                 300

Phe Pro Tyr Pro Lys Trp Asn Ser Val Phe Asp Gln Leu Thr Gln Val
305                 310                 315                 320

Val Lys Gly Asp Pro Pro Gln Leu Ser Asn Ser Glu Glu Arg Glu Phe
                325                 330                 335

Ser Pro Ser Phe Ile Asn Phe Val Asn Leu Cys Leu Thr Lys Asp Glu
            340                 345                 350

Ser Lys Arg Pro Lys Tyr Lys Glu Leu Leu Lys His Pro Phe Ile Leu
        355                 360                 365

Met Tyr Glu Glu Arg Ala Val Glu Val Ala Cys Tyr Val Cys Lys Ile
```

```
      370              375              380
Leu Asp Gln Met Pro Ala Thr Pro Ser Ser Pro Met Tyr Val Asp
385                 390                 395
```

(2) INFORMATION FOR SEQ ID NO:93:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:93:

GAGCCTCAAT TCCAGTTTTC C                         21

(2) INFORMATION FOR SEQ ID NO:94:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:94:

TATGATGCAG CACTGCAGTT                           20

(2) INFORMATION FOR SEQ ID NO:95:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:95:

AAGCTTCCGC GGGCCACCAT GTATCCATAC GATGTTCCAG ATTACGCAGC GGCTCCGAGC     60

CCGA                                                                       64

(2) INFORMATION FOR SEQ ID NO:96:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:96:

TTCTTTACGT CTTGCTTCCT CTC                        23